United States Patent [19]
Yan et al.

[11] Patent Number: 5,830,539
[45] Date of Patent: Nov. 3, 1998

[54] METHODS FOR FUNCTIONALIZING AND COATING SUBSTRATES AND DEVICES MADE ACCORDING TO THE METHODS

[75] Inventors: Mingdi Yan, Portland; John F. W. Keana, Eugene; Goran Karapetrov, Milwaukie, all of Oreg.; Christopher J-P Sevrain, Ridgefield, Wash.; Martin N. Wybourne, Eugene, Oreg.

[73] Assignee: The State of Oregon Acting by and through the State Board of Higher Education on Behalf of the University of Oregon, Eugene, Oreg.

[21] Appl. No.: 565,199

[22] Filed: Nov. 17, 1995

[51] Int. Cl.$^6$ .............................. B05D 7/14; B05D 3/06; B05D 3/10
[52] U.S. Cl. ..................... 427/551; 427/2.13; 427/2.24; 427/387; 427/388.1; 427/552; 427/596; 427/337
[58] Field of Search ..................... 435/176, 177; 427/512, 387, 2.13, 2.24, 551, 552, 596, 388.1, 337, 338

[56] References Cited

U.S. PATENT DOCUMENTS

| | | | |
|---|---|---|---|
| 3,205,206 | 9/1965 | Marcantonio | 522/126 |
| 3,211,713 | 10/1965 | Breslow | 522/126 |
| 3,284,421 | 11/1966 | Breslow | 522/126 |
| 3,888,833 | 6/1975 | Lednicer et al. | 525/351 |
| 4,007,089 | 2/1977 | Smith, III | 435/181 |
| 4,309,453 | 1/1982 | Reiner et al. | 427/520 |
| 4,562,157 | 12/1985 | Lowe et al. | 435/176 |
| 4,654,292 | 3/1987 | Oie et al. | 430/197 |
| 4,716,122 | 12/1987 | Scheefers | 436/532 |
| 4,767,814 | 8/1988 | Bae et al. | 524/284 |
| 4,798,585 | 1/1989 | Inoue et al. | 604/93 |
| 4,835,258 | 5/1989 | Hollenberg et al. | 435/177 |
| 4,898,951 | 2/1990 | Symons | 548/303 |
| 5,002,582 | 3/1991 | Guire et al. | 623/66 |

(List continued on next page.)

OTHER PUBLICATIONS

Y. Imanishi, "Polymeric Biomaterials," *Materials Science and Engineering*, C1, pp. 143–147 (1994)(no month available).

Ishihara, et al., "Designing Biocompatible Materials," *Chemtech*, pp. 19–25 (Oct. 1993).

D. Williams, "Advanced Applications for Materials Implanted Within the Human Body," *Materials Science and Technology*, vol. 3, pp. 797–806 (Oct. 1987).

Legeay, et al., "Surface Treatment and Biomaterial," *Le Vide, les Couches Minces* No. 267—Mai–Juin–Juillet, pp. 161–170 (1993).

"A Coat of Many Lipids—In the Clinic," *Chemistry in Britain*, pp. 253–257 (Mar. 1992).

(List continued on next page.)

*Primary Examiner*—Diana Dudash
*Attorney, Agent, or Firm*—Klarquist Sparkman Campbell Leigh & Whinston, LLP.

[57] ABSTRACT

Methods for coating substrates are described. The methods comprise coating at least a portion of a substrate with particular coating materials. The coating materials can be crosslinked and coated onto a substrate. Alternatively, the coating materials may be covalently bonded to the substrates. The coating materials might themselves functionalize the substrate, or provide a biocompatible coating on the substrate. The coating materials might also include electrophilic or nucleophilic groups that allow for the subsequent reaction of the coating materials with additional reagents. The present invention also provides coated workpieces, particularly medical workpieces having a surface for contacting tissue or blood. These workpieces comprise a first layer and a second layer. The first layer comprises a molecular tether covalently bonded to the surface. The second layer is bonded to the article by the first layer and comprises a bioactive agent selected from the group consisting of biocompatible polymers, antibiotics, antimicrobials and anticoagulants.

32 Claims, 12 Drawing Sheets

U.S. PATENT DOCUMENTS

| | | |
|---|---|---|
| 5,024,742 | 6/1991 | Nesburn et al. .................. 204/157.68 |
| 5,240,747 | 8/1993 | Matsuda et al. .......................... 427/512 |
| 5,336,518 | 8/1994 | Narayanan et al. ......................... 623/1 |
| 5,344,455 | 9/1994 | Keogh et al. ............................. 623/11 |
| 5,372,888 | 12/1994 | Ogawa et al. ........................... 428/422 |
| 5,405,766 | 4/1995 | Kallury et al. ........................... 435/176 |
| 5,412,087 | 5/1995 | McGall et al. ......................... 536/24.3 |
| 5,547,711 | 8/1996 | Kirchmayer et al. ................... 427/387 |
| 5,580,697 | 12/1996 | Keana et al. ............................ 430/296 |

OTHER PUBLICATIONS

Eberhart, et al., "Platelets, Catheters, and the Vessel Wall—Catheter Coatings, Blood Flow, and Biocompatibility," *Seminars in Hematology*, vol. 28, No. 4, Suppl. 7, pp. 42–48 (Oct. 1991).

D. Chapman, "Biocompatible Surfaces Based Upon the Phospholipid Asymmetry of Biomembranes," *Biochemical Society Transactions*, pp. 258–262 1993 (no month available).

Sanchez, et al., "Synthesis of Hemocompatible Materials. Part 1: Surface Modification of Polyurethanes Based on Poly (chloroalkylvinylether) s by RGD Fragments," *Clinical Materials 15*, pp. 253–258 (1994). no month available.

Moussy, et al., "Prevention of the Rapid Degradation of Subcutganeously Implanted Ag/AgC1 Reference Electrodes Using Polymer Coatings," *Anal. Chem.*, v.66, pp. 674–679 (1994) Mar.

Osteraass, et al., "Modification of Polyethylene Surfaces with Carbethoxy Substituted Carbenes and Nitrenes,," *J. Appl. Polym. Sci.*, 13:1537–1544 (1969)(no month available).

Osteraas, et al., "Incorporation of Functional Groups Onto the Surface of Polyethylene," *Nature*, 221:1140–1141 (1969) Mar.

Abbott, et al., "Manipulation of the Wettability of Surfaces on the 0.1– to 1–Micrometer Scale Through Micromachining and Molecular Self–Assembly," *Science*, 257:1380–1381(1992) Sep.

Stenger, et al., "Coplanar Molecular Assemblies of Amino and Perfluorinated Alkylsilanes: Characterization and Geometric Definition of Mammalian Cell Adhesion and Browth," *J. Am. Chem. Soc.*, 114:8435–8442 (1992)(no month).

Wring, et al., "Chemically Modified, Carbon–based Electrodes and Their Application as Electrochemical Sensors for the Analysis of Biologically Important Compounds—A Review," *Analyst*, 117:1215–1229 (1992) Aug.

Yokohama, et al., "Synthesis of Poly (ethylene oxide) with Heterobifunctional Reactive Groups at Its Terminals by an Anionic Initiator," *Bioconjugate Chem.*, 3:275–276 (1992) no month.

Braybrook, et al., "Organic Polymer Surfaces for Use in Medicine: Their Formation, Modification, Characterisation and Application," *Prog. Polym. Sci.*, 15:715–734 (1990) no month.

Carlsson, et al., "Plasma Modification and Its Effect on Polymer–Polymer and Polymer–Metal Adhesion," *Polymer Materials Science and Engineering*, Fall Meeting 1992, Washington, D.C. vol. 67, pp. 21–23 (1992) (no month available).

Cai, et al., "Introduction of Functional Groups into Polymer Films via Deep–UV Photolysis of Electron–Beam Lithography: Modification of Ploystyrene and Poly (3–octylthiophene) by a Fucntionalized Perfluorophenyl Azide," *Chem. Mater.*,4:879–884 (1992)(no month available).

METHODS FOR FUNCTIONALIZING AND COATING SUBSTRATES AND DEVICES MADE ACCORDING TO THE METHODS

FIELD OF THE INVENTION

This invention concerns methods for chemically functionalizing and/or coating materials and devices made according to the methods, such as implantable medical devices having biocompatible materials attached thereto.

BACKGROUND OF THE INVENTION

Chemical modification of various materials, such as polymers and polymer surfaces, has been the subject of intensive research. Methods for functionalizing polymers and the products made by such methods have been studied extensively due to their wide potential application in biology, chemistry, medicine, and in techniques involving ion-exchange resins, immobilized biological macromolecules, and electrically conductive polymers. Akelah et al., *Functionalized Polymers and Their Applications*, Chapman and Hall, London (1990).

Chemical modification of polymer films or film surfaces with concomitant introduction of functional groups is important for the development of new materials such as novel composites, Baum et al., *Chem. Mater.* 3:714–720 (1991); resist materials, MacDonald et al., *Chem. Mater.* 3:435–442 (1991); biosensors, Pantano et al., *J. Am. Chem. Soc.* 113:1832–1833 (1991); and biomaterials, Allcock et al., *Chem. Mater.* 3:450–454 (1991). Examples of existing methods for modifying polymer films include sulfonation of polystyrene, Gibson et al., *Macromolecules* 13:34 (1980); sulfonation of poly(aryloxy)phosphazenes, Allcock et al., *Chem. Mater.* 3:1120 (1991); plasma treatment of polyester, Porta et al., *Chem. Mater.* 3:293 (1991); base hydrolysis of polyimide, Lee et al., *Macromolecules* 23:2097 (1990); base hydrolysis of polyphosphazenes, Allcock et al., *Chem. Mater.* 3:1441 (1991); and base treatment of poly(vinylidene fluoride), Dias et al., *Macromolecules* 17:2529 (1984).

Another conventional method for modifying polymers comprises exposing the surface of a hydrocarbon polymer, such as polyethylene, with nitrene or carbene intermediates generated in the gas phase. Breslow, in Scriven (ed.), *Azides and Nitrenes*, chapter 10, Academic Press, NY (1984). Also, difluorocarbene generated in solution has been reported to modify 1,4-polybutadienes. Siddiqui et al., *Macromolecules* 19:595 (1986).

Functionalization of material surfaces also has been studied. Examples include Braybrook et al., *Prog. Polym. Sci.* 15:715–734 (1990); metals, Stratmann, *Adv. Mater.* 2:191–195 (1990); silica, Bhatia et al., *J. Am. Chem. Soc.* 114:4432–4433 (1992); and graphite, Delamar, *J. Am. Chem. Soc.* 114:5883–5884 (1992). This research has been principally directed toward the development of novel composites, Baum et al., *Chem. Mater.* 3:714–720 (1991); resist materials, MacDonald et al., *Chem. Mater.* 3:435–442 (1991); biosensors, Pantano et al., *J. Am. Chem. Soc.* 113:1832–1833 (1991); and biomaterials, Allcock et al., *Chem. Mater.* 3:450–454 (1991).

Recently, surface modification has been combined with photolithography to spatially direct the synthesis of peptides or oligonucleotides, Fodor et al., *Science* 251:767–773 (1991) and Kiederowski, *Angew. Chem. Int. Ed. Eng.* 30:822–823 (1991); and immobilization of biopolymers. Rozsnyai et al., *Angew. Chem. Int. Ed. Eng.* 31:759–761 (1992). Most of the surface modification processes known in the art involve sequential treatment of surfaces with chemical reagents. Id. Only a few such studies have involved the use of azides as surface-modification reagents. Breslow, in Scriven (ed.) *Azides and Nitrenes*, chapter 10, Academic Press, NY (1984); Harmer, *Langmuir* 7:2010–2012 (1991).

Examples of existing methods for modifying polymer films include sulfonation of polystyrene, Gibson et al., *Macromolecules* 13:34 (1980); sulfonation of poly(aryloxy) phosphazenes, Allcock et al., *Chem. Mater.* 3:1120 (1991); plasma treatment of polyester, Porta et al., *Chem. Mater.* 3:293 (1991); base hydrolysis of polyimide, Lee et al., *Macromolecules* 23:2097 (1990); base hydrolysis of polyphosphazenes, Allcock et al., *Chem. Mater.* 3:1441 (1991); and base treatment of poly(vinylidene fluoride), Dias et al., *Macromolecules* 17:2529 (1984).

Another conventional method for modifying polymers comprises exposing the surface of a hydrocarbon polymer such as polyethylene with nitrene or carbene intermediates generated in the gas phase. Breslow, in Scriven (ed.), *Azides and Nitrenes*, chapter 10, Academic Press, NY (1984). Also, difluorocarbene generated in solution has been reported to modify 1,4-polybutadienes. Siddiqui et al., *Macromolecules* 19:595 (1986).

Perfluorophenyl azides (PFPAs) have been shown to exhibit improved CH-insertion efficiency over their nonfluorinated analogues when the PFPAs were photolyzed in hydrocarbon solvents such as cyclohexane or toluene. Keana et al., *Fluorine Chem.* 43:151 (1989); Keana et al., *J. Org. Chem.* 55:3640 (1990); Leyva et al., *J. Org. Chem.* 54:5938 (1989); and Soundararajan et al., *J. Org. Chem.* 55:2034 (1990). PFPAs were initially developed as efficient photolabeling reagents. Cai et al., *Bioconjugate Chem.* 2:38 (1991); Pinney et al., *J. Org. Chem.* 56:3125 (1991); and Crocker et al., *Bioconjugate Chem.* 1:419 (1990). Recently, bis-(PFPA)s have been shown to be efficient cross-linking agents for polystyrene, Cai et al., *Chem. Mater.* 2:631 (1990); and poly(3-octylthiophene), Cai et al., *J. Molec. Electron.* 7:63 (1991).

Potentiating the biocompatibility of materials generally used as structural materials for the formation of medical and veterinary devices also has received attention. A number of medical devices have been developed that must contact tissue and/or blood. A partial list of such devices would include angioplasty devices, pacemakers, arterial grafts, heart valves, artificial hearts, heart pumps, protheses, heart-lung machines, catheters, electrodes, and kidney dialysis machines. The materials used to make these devices generally are foreign to animal and human bodies. This leads to many problems associated with bioincompatibility, such as cellular destruction and thrombogenesis (coagulation of blood to form clots). The process of implanting devices in animals or humans also subjects the animal or human to infection, such as infection by Staph. epidermidis and Staph. aureus. Such pathogens tend to attack the site at which the device or material is implanted.

This problem can be addressed by attaching to the surface of a substrate a material that potentiates the biocompatibility or pathogenic resistance of the neighboring tissue. For instance, a partial list of materials that can be attached to surfaces includes biocompatible polymeric materials, such as cellulose, chitosan and PEEK, antibacterial or antimicrobial agents, anticoagulants, enzymes, catalysts, hormones, growth factors, lectin drugs, vitamins, antibodies, antigens, nucleic acids, dyes, DNA or RNA segments, proteins and peptides.

In view of the present state of the art in chemical modification and coating of substrates and substrate surfaces, there remains a need for other methods for chemically functionalizing and coating substrates and substrate surfaces, particularly in a single step.

There is also an ongoing need for new types of chemically modified or coated molecules, particularly functionalized polymers, for use in any of a wide variety of applications.

SUMMARY OF THE INVENTION

The foregoing needs are met by the present invention which provides methods for covalently modifying (i.e., functionalizing) materials, including the surfaces thereof, and provides various functionalized substrates and substrate surfaces.

Polymeric substances that can be functionalized according to the present invention include any of various substances comprising synthetic and/or natural polymer molecules having chemical moieties each capable of undergoing an addition reaction with a nitrene. A polymeric substance is functionalized according to the method of the present invention by adding to the polymeric substance a functionalizing reagent. The functionalizing reagent comprises molecules each having a nitrenogenic group and a functionalizing group. The molecules of the functionalizing reagent are brought into reactive proximity to the polymer molecules such as by, but not limited to, forming a solution of the functionalizing reagent and the polymer molecules. The solution can be formed into a film or other suitable shape, then dried.

While the molecules of the functionalizing reagent and the polymer molecules are in reactive proximity, the molecules are exposed to a reaction-energy source such as photons, electrons, or heat. In the presence of the reaction-energy source, the nitrenogenic groups on molecules of the functionalizing reagent form nitrene intermediates that covalently react with —CH, —NH, —OH, —C=C—, C—C and other groups on the polymer molecules so as to cause "nitrene addition" or "nitrene insertion" of the functionalizing groups to the polymer molecules. The nitrene addition or nitrene insertion results in the functional groups becoming covalently bonded to the polymer molecules.

Substrates that can be functionalized according to the present invention include, but are not limited to, a wide variety of polymeric materials, as well as various allotrophic forms of elemental carbon (e.g., graphite, "carbon electrodes," diamond and diamond films, and fullerenes such as $C_{60}$ and $C_{70}$), siliceous materials, and any of various metals. The substrate also can be a semiconductor material such as silicon, gallium arsenide, and other semiconducting materials (doped or not doped).

Substrate surfaces are functionalized according to the method of the present invention by exposing the surface to a nitrenogenic functionalizing reagent in the presence of a reaction-energy source such as photons, electrons, or heat. In the presence of the reaction-energy source, the functionalizing reagent forms a nitrene intermediate that covalently reacts with —CH, —NH, —OH, —C=C—, —C—C— and other groups on the substrate surface so as to cause "nitrene addition" or "nitrene insertion" of the functionalizing reagent to the substrate surface. In order to form nitrene intermediates, the functionalizing reagent must terminate with an azide group or analogous chemical group capable of forming a reactive nitrene when exposed to a reaction-energy source.

According to the present invention, the substrate and/or substrate surface is functionalized via either a single-stage or a multi-stage process. In a multi-stage process, each stage typically involves different functionalizing reagents. In both single- and multi-stage processes, at least one stage involves a nitrenogenic functionalizing reagent.

In a single-stage process, each molecule of the functionalizing agent comprises, in addition to the nitrenogenic group, a functionalizing group covalently coupled to the nitrenogenic group. The functionalizing group can be virtually any desired chemical group that does not cross-react with the nitrene intermediate or otherwise significantly interfere with the nitrene addition reaction of the functionalizing agent with the substrate surface. For example, the functionalizing group can be selected from, but is not necessarily limited to, radioactive labels, fluorescent labels, enzymes, pharmacologically active groups, diagnostically active groups, antibodies, nucleic acids, surfactants, and any of a wide variety of other groups.

Functionalizing reagents adapted to functionalize substrates in multi-stage reactions can be configured in several ways. According to one method, a first functionalizing reagent is reacted with the substrate so as to achieve covalent attachment of the first functionalizing-reagent molecules to the substrate surface or throughout the cross-section of the substrate; afterward, a second functionalizing reagent is added so as to react with, and therefore covalently bond to, the attached first functionalizing-reagent molecules. In such a method, the first functionalizing reagent comprises molecules each comprising, in addition to the nitrenogenic group, a first functionalizing group adapted to participate in subsequent chemistry after the first functionalizing reagent has been covalently bonded to the substrate via nitrene addition. For example, the first functionalizing group can be an active ester that is reactive with —NH groups, —OH groups, or other nucleophilic groups on molecules of a second functionalizing reagent. The second functionalizing reagent can then provide a second functionalizing group ultimately desired to be attached to the substrate, such as an enzyme, antibody, diagnostic agent, or therapeutic agent.

An alternative multi-stage process comprises first reacting the second functionalizing reagent (comprising the second, or ultimately desired, functionalizing group) with the first functionalizing reagent (including a nitrenogenic group). Then the product of the first reaction is reacted with the substrate in the presence of a reaction-energy source so as to covalently attach the product of the first reaction to the substrate via nitrene addition.

A class of preferred functionalizing reagents for single- and multi-stage processes according to the present invention consists of N-hydroxysuccinimide active ester-functionalized perfluorophenyl azides (NHS-PFPAs). The NHS active ester groups become covalently attached to the substrate via generation during the reaction of highly reactive nitrene intermediates derived from the PFPA portion of the reagent molecules. (The reactive nitrene portion of the intermediates are preferably constrained structurally such that the nitrene portion cannot react intramolecularly with the NHS active ester portion.) Thus, the substrate, either the surface thereof or throughout the substrate cross-section, becomes "modified" (i.e., "functionalized". Afterward, the active esters can participate in further reactions with a variety of nucleophilic reagents, such as reagents containing primary amines or hydroxyls (such as biomolecules) by way of amide or ester formation, respectively.

According to another aspect of the present invention, a nitrene-forming functionalizing reagent can be applied, such as in the form of a film, to the substrate surface. Alternatively, a mixture comprising molecules of a nitrene-forming functionalizing reagent and polymer molecules can be applied, such as in the form of a film, to the surface of a substrate. Then, the coating, film or coated surface is exposed to a reaction-energy source (such as photons or a beam of particles such as an electron beam) in a spatially selective way to functionalize certain regions of the surface and not others, thereby creating a functionalized pattern on the surface. Such patterns can have dimensions measured in micrometers and smaller, due to the highly resolved manner in which the coated surface can be exposed to the reaction-energy source. Thus, the present invention has wide applicability in microelectronics and in the construction of novel micron-scale biosensors.

Another aspect of the present invention provides methods for coating substrates comprising coating at least a portion of a substrate with a coating material that, prior to the coating, satisfies the formula

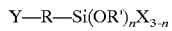

wherein n is 0–3, R is an aromatic group or an alkyl chain having 1–20 carbon atoms, R' is an alkyl chain having 1–10 carbon atoms, X is a halogen, and Y is selected from the group consisting of H, —OH, —$NH_2$ and —SH. If Y is H, the method may further comprise bringing the coated substrate into reactive proximity with a perhalophenyl azide (PHPA). The substrate and the PHPA are then exposed to a reaction energy source to couple the PHPA to the substrate. The step of exposing often comprises exposing only preselected portions of the substrate to the reaction energy source. This allows the formation of arrays of coating materials on the substrate, or allows for the formation of substrates having coating materials coupled to only certain, preselected portions of the substrate.

A particularly suitable PHPA is an N-hydroxysuccinimide active ester-functionalized perfluorophenyl azide (NHS-PFPAs). The NHS-PFPA provides an activated ester (i.e., an ester that is more reactive to nucleophilic attack than an alkyl ester or a carboxylic acid) that can be reacted with a nucleophile to couple the nucleophile to the substrate. Virtually any nucleophile could be reacted in this manner; however, by way of example only and without limitation, the nucleophile may be selected from the group consisting of peptides, nucleotides, cells and antibodies.

Y also can be a nucleophilic species, such as —OH, —SH and —$NH_2$. Thus, Y can be selected to provide a nucleophile that can be subsequently reacted with an electrophilic species, one example of which is an electrophilic PHPA. Once the electrophilic PHPA is coupled to the substrate, the method may further comprise bringing the substrate with attached PHPA into reactive proximity with a material having chemical moieties each capable of undergoing an insertion and/or addition reaction with a nitrene. The substrate and the PHPA are exposed to a reaction energy source to form nitrenes that undergo insertion and/or addition reactions with the chemical moieties capable of undergoing insertion and/or addition reactions with nitrenes. The step of exposing may comprise exposing only preselected portions of the substrate to the reaction energy source. Examples, without limitation, of materials having chemical moieties each capable of undergoing an insertion and/or addition reaction with nitrenes are polymeric materials, such as biocompatible polymers. If the substrate is an implantable medical device or comes into contact with blood or tissue, then the material having chemical moieties each capable of undergoing an insertion and/or addition reaction with nitrenes likely, but not necessarily, is a biocompatible polymer.

Still another method according to the present invention comprises coating at least a portion of a substrate or workpiece with a material that, prior to the coating, satisfies the formula

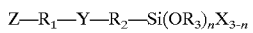

wherein n is 3 or less, $R_1$ is an aromatic group or an alkyl, alkenyl or an alkynyl chain having 1–20 carbon atoms, $R_2$ is an aromatic group or an alkyl, alkenyl or an alkynyl chain having 1–20 carbon atoms, $R_3$ is an alkyl chain having 1–10 carbon atoms, X is a halogen, Y is NH, COO—, CON— or COS—, and Z is a methyl group, —$N_3$, —$NH_2$, —OH or —SH. $R_1$ may be a PHPA. If Z is a nucleophilic species, such as —$NH_2$, —OH or —SH, the nucleophilic species can be reacted with an electrophile, such as an electrophilic PHPA. If Z is $N_3$, the substrate can be reacted with a material having chemical moieties each capable of undergoing an insertion and/or addition reaction with a nitrene. As used herein, workpiece includes, but is not limited to:

(a) devices made from materials such as silica, quartz, glass and mica;
(b) devices made from graphite;
(c) devices made from metals, particularly gold, aluminum, platinum, silver, copper and iron, and alloys containing these metals, such as steel;
(d) devices made from semiconductors, such as gallium arsenide and cadmium sulfide;
(e) devices made from polymeric materials, such as polyoctyl-3-thiophene, polystyrene, polypropylene, polyethylene, polyphenol, polyimide, PMMA, and $C_{60}$; and
(f) particular devices, such as medical instruments, silicon wells, carbon electrodes and angioplasty balloons.

Still another method according to the present invention comprises potentiating the biocompatibility of a workpiece. The method comprises applying a reagent comprising molecules each having a nitrenogenic group and a functional group to a workpiece. The workpiece is then exposed to a reaction energy source so as to convert the nitrenogenic groups to nitrenes that undergo addition and/or insertion reactions with chemical moieties on the workpiece, thereby attaching the reagent to the workpiece. A biocompatible material is then coupled to the functional group. For instance, a partial list of materials that can be attached to surfaces includes biocompatible polymeric materials, such as cellulose, chitosan and PEEK, antibacterial or antimicrobial agents, anticoagulants, enzymes, catalysts, hormones, growth factors, lectin drugs, vitamins, antibodies, antigens, nucleic acids, dyes, DNA or RNA segments, proteins and peptides.

For example, the workpiece might be an angioplasty balloon made from polyethyleneteraphthalate. In this case the functional group might be an activated ester. The method would thus further comprise coating a solution of a nucleophilic PHPA, such as an amino-perhalophenyl azide, onto the balloon so as to cause the nucleophilic PHPA to couple with the activated ester. The balloon is then exposed to a biocompatible polymeric material, such as polyurethane The balloon and biocompatible material are then exposed to a reaction energy source so as to convert the azide into nitrenes that undergo insertion and/or addition reactions with the polymeric material.

Still another embodiment of the invention comprises providing a substrate and coating the substrate with a solution comprising a polymeric material having chemical moieties each capable of undergoing an insertion and/or addition reaction with a nitrene and a reagent comprising molecules each having two or more nitreneogenic groups. The polymeric material and reagent are then exposed to a reaction energy source so as to convert the nitreneogenic groups to nitrenes that undergo insertion and/or addition reactions with the chemical moieties each capable of undergoing insertion and/or addition reactions with nitrenes. For example, the substrate might be a silicon reservoir having an interior surface and an exterior surface. In this case, the step of coating generally comprises coating only the interior surface with a crosslinked polymeric material. A currently useful reagent for this purpose is 2,6-bis(4'-azido-2',3',5',6'-tetrafluorophenyl)-4-methyl cyclohexanone (bis-PFPA).

Still another embodiment of the present invention comprises coating at least a portion of a substrate with a coating material that, prior to the coating, satisfies a first formula

Y—R—Z wherein
(a) R is an aromatic group or an alkyl, alkenyl or an alkynyl chain having 1–20 carbon atoms;
(b) Y is H, —OH, —SH, or $NH_2$; and
(c) Z is —SH, $CO_2H$, or $Si(OR')_nX_{3-n}$ wherein n is 0–3 and R' is an alkyl chain having 1–10 carbon atoms, or a second formula $(Y—R—Z—)_2$ wherein
(d) R is an aromatic group or an alkyl, alkenyl or an alkynyl chain having 1–20 carbon atoms;
(e) Y is H, —OH, —SH, or $NH_2$; and
(f) Z is S or an anhydride. If the coating material is a thiol (RSH) or a disulfide (—S—S—), then the substrate might be a semiconductor, such as gallium arsenide and cadmium sulfide, or a metal substrate wherein the metal is selected from the group consisting of gold, aluminum, copper and platinum. If the substrate is made from aluminum, then the coating material generally is a carboxylic acid or an anhydride. As with the embodiments discussed above, the coating material may be applied only to preselected portions of the substrate, and may be applied to form arrays.

The present invention also provides coated workpieces, particularly medical workpieces having a surface for contacting tissue or blood. These workpieces comprise a first layer and a second layer. The first layer comprises a molecular tether covalently bonded to the surface that, prior to attachment to the article, satisfies the formula $Z—R_1—Y—R_2—Si(OR_3)_nX_{3-n}$ wherein n is 3 or less, $R_1$ is an aromatic group or an alkyl, alkenyl or an alkynyl chain having 1–20 carbon atoms, $R_2$ is an aromatic group or an alkyl, alkenyl or an alkynyl chain having 1–20 carbon atoms, $R_3$ is an alkyl chain having 1–10 carbon atoms, X is a halogen, Y is NH, COO—, CON— or COS—, and Z is a methyl group, $—N_3$, $—NH_2$, —OH or —SH. The second layer comprises a bioactive agent selected from the group consisting of biocompatible polymers, antibiotics, antimicrobials and anticoagulants. The second layer is bonded to the article by the first layer.

DETAILED DESCRIPTION OF THE PREFERRED EMBODIMENTS

Figure 1:
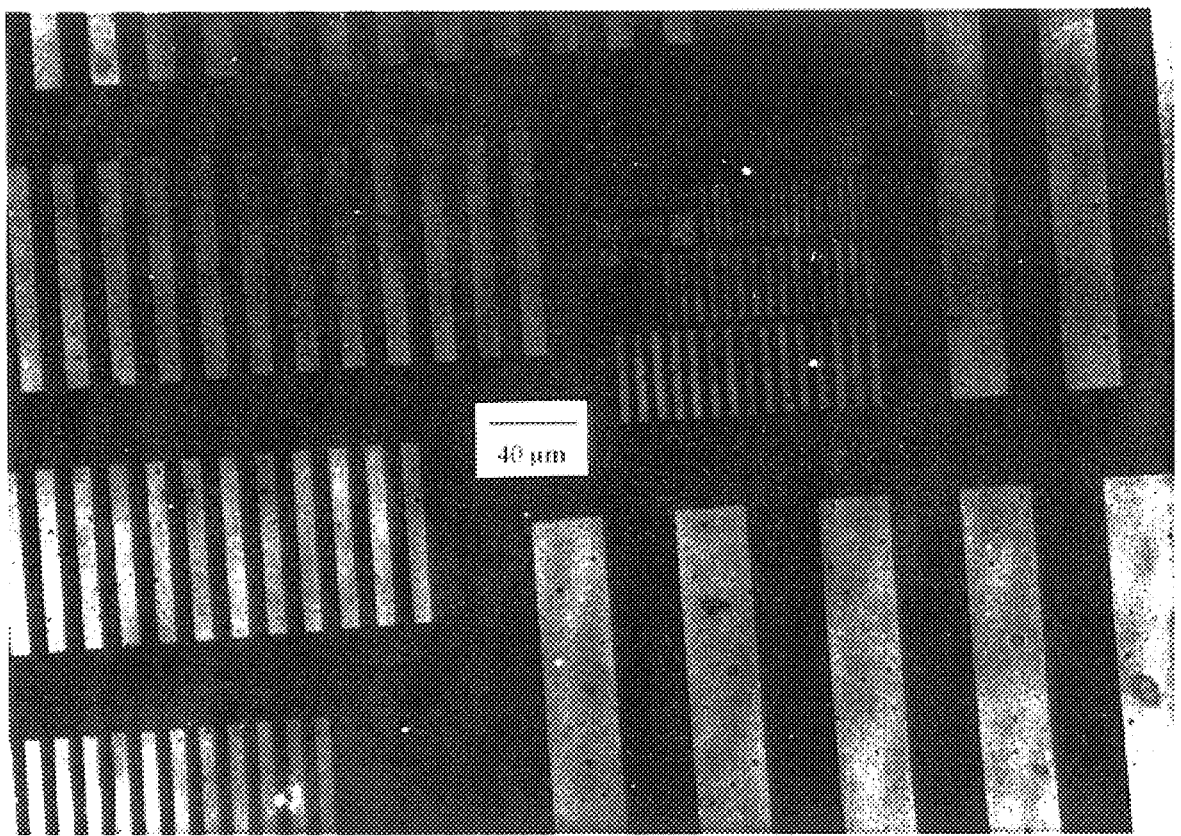
FIG. 1 is a photograph of micron-sized patterns as observed under a fluorescence microscope (450–490 nm excitation wavelength; >510 nm emission) showing the surface modification of a polystyrene film as described in Example 4.

The following terms are used herein:

A "substrate" is a non-fluid material providing a surface that can be functionalized according to the present invention. A substrate can comprise polymer molecules (e.g., thermoplastic polymer molecules), a thermoset molecular network (e.g., cross-linked polymer molecules), or other atomic or molecular associations such as found in certain glasses and crystals.

A "surface molecule" is a substrate molecule having at least a portion thereof present on the substrate surface.

A "polymeric material or substrate" is a substrate comprising polymer molecules or a network of polymer molecules.

A "polymer molecule" is a relatively large molecule formed by covalently linking smaller molecules termed "monomers." The monomers present in a polymer molecule can be the same or different. Polymer molecules can be natural, such as (but not limited to) cellulose, starch, proteins, and nucleic acids; or synthetic such as (but not limited to) nylon and polyethylene. In a polymeric material, polymer molecules can be associated with each other in any of several ways, including non-covalently (as a thermoplastic) or a covalently cross-linked network (as a thermoset).

A "functionalized substrate" is a substrate to which one or more functional groups are covalently bonded according to the methods of the present invention.

A "functional group" is a group of one or more atoms bonded together in an organized way so as to have a desired chemical property. Certain functional groups can, when covalently bonded to a substrate surface, participate in one or more additional bonding reactions with either a similar functional group or a different type of functional group. Such bonding reactions can result in: (a) attachment to the functional groups of any of a variety of additional functional groups; or (b) coupling together (cross-linking) of the functionalized substrate molecules. Many other functional groups attachable to polymer molecules according to the present invention can confer altered chemical properties to the polymer molecules such as, but not limited to, making them labeled or tagged with a fluorescent, radioactive, immunologic, diagnostic or therapeutic markers.

The term "functionalized polymer" can concern either a functionalized polymeric substrate or a functionalized polymer molecule. Functionalized polymer molecules comprise one or more functional groups covalently bonded to the polymer molecules according to the present invention.

A "functionalizing reagent" according to the present invention is a reagent adapted for functionalizing a substrate. Molecules of functionalizing agents have at least one nitrenogenic group (as a first functional group) coupled to a second functional group. The nitrenogenic group preferably is constrained by the molecular structure of the functionalizing-reagent between the nitrenogenic group and the functional group. The nitrenogenic groups are capable under reaction conditions of functionalizing a substrate surface.

A "nitrenogenic group" on a functionalizing reagent is a chemical moiety that, when exposed to a reaction-energy source, becomes a nitrene group.

The phrase "addition reaction" when used in the context of reactions of the nitrene group of the functionalizing reagents with surface molecules, generally refers to any of the various addition and insertion reactions that nitrenes can undergo with molecules on the substrate surface according to the present invention.

A "nitrene group" (also generally termed "nitrene" or "nitrene intermediate") is a particular form of nitrogen group that can be depicted as a singlet by the structure: R-$\underline{\text{N}}$, and as a triplet by the structure: R-$\overline{\text{N}}$·. Nitrenes are regarded by persons skilled in the art as the nitrogen analogs of carbenes. Like carbenes, nitrenes are generally regarded as intermediates that are highly reactive and generally cannot be isolated under ordinary conditions. However, certain chemical reactions, such as reactions according to the present invention, would not otherwise be explainable by known reaction mechanisms without the presumed existence of nitrenes. Important nitrene reactions can be summarized by the following:

(a) Nitrenes, including aryl nitrenes, can undergo addition reactions at —CH sites and at —NH sites; e.g.:

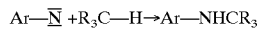

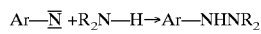

(b) Nitrenes can also undergo addition at —C—C— and —C=C— bonds; e.g.:

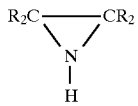

According to the present invention, a functionalizing reaction occurs when a functionalizing reagent comprising a nitrenogenic group is exposed to a reaction-energy source, which converts the nitrenogenic group to a nitrene intermediate. The functionalizing reaction proceeds by reaction of the nitrene intermediate with the substrate surface.

A "reaction-energy source" is an energy source that drives a functionalizing reaction according to the present invention by, in particular, converting nitrenogenic groups on functionalizing reagent molecules to nitrenes which react with the substrate surface. Suitable reaction-energy sources include (but are not limited to): photons (such as ultraviolet (UV) light, deep-UV light, laser light, X-rays, and heat in the form of infrared radiation or conductive heating), energized electrons (such as an electron beam), and energized ions (such as an ion beam). These reaction-energy sources are conventionally used for such tasks as lithography, scanning microscopy, and, in the case of UV and visible photons, effecting photochemical reactions and excitation of fluorescent molecules.

A "functionalizing reaction" is a reaction in which a substrate surface is functionalized according to the present invention. A functionalizing reaction can consist of one or more stages. At least one stage involves the reaction in the presence of a reaction-energy source of the substrate surface with molecules of a functionalizing reagent comprising nitrenogenic groups.

According to the present invention, a substrate is functionalized by a chemistry whereby functional groups on functionalizing reagent molecules become covalently bonded to the substrate or substrate surface. Such covalent bonding is achieved by conversion of nitrenogenic groups on the functionalizing reagent molecules (the functionalizing reagent molecules also each comprising a desired functional group as set forth below) to a nitrene intermediate highly reactive with the substrate surface by exposure of the functionalizing reagent molecules to a reaction-energy source.

The functionalizing reagent is preferably selected from a group consisting generally of: aryl azides, alkyl azides, alkenyl azides, alkynyl azides, acyl azides, and azidoacetyl derivatives, all capable of carrying a variety of substituents. Halogen atoms are present to the maximum extent possible in the positions on the functionalizing reagent molecule adjacent the azide group. Best results are achieved when fluorine and/or chlorine atoms are the halogen atoms.

Each of the foregoing azides may also contain within the same molecule any of the following functional groups, constrained structurally from reacting with the nitrene moiety after the nitrene moiety is generated:

(a) carboxyl groups and various derivatives thereof such as (but not necessarily limited to): N-hydroxysuccinimide esters; N-hydroxybenzotriazole esters; acid halides corresponding to the carboxyl group; acyl imidazoles; thioesters; p-nitrophenyl esters; alkyl, alkenyl, alkynyl and aromatic esters, including esters of biologically active (and optically active) alcohols such as cholesterol and glucose; various amide derivatives such as amides derived from ammonia, primary, and secondary amines and including biologically active (and optically active) amines such as epinephrine, dopa, enzymes, antibodies, and fluorescent molecules;

(b) alcohol groups, either free or esterified to a suitable carboxylic acid which could be, for example, a fatty acid, a steroid acid, or a drug such as naprosin or aspirin;

(c) haloalkyl groups wherein the halide can be later displaced with a nucleophilic group such as a carboxylate anion, thiol anion, carbanion, or alkoxide ion, thereby resulting in the covalent attachment of a new group at the site of the halogen atom;

(d) maleimido groups or other dienophilic groups such that the group may serve as a dienophile in a Diels-Alder cycloaddition reaction with a 1,3-diene-containing molecule such as, for example, an ergosterol;

(e) aldehyde or ketone groups such that subsequent derivatization is possible via formation of well-known carbonyl derivatives such as hydrazones, semicarbazones, or oximes, or via such mechanisms as Grignard addition or alkyllithium addition; and (f) sulfonyl halide groups for subsequent reactions with amines, for example, to form sulfonamides.

A general reaction by which a functionalizing reagent is converted to a nitrene intermediate is:

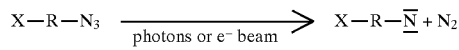

where X is the functional group and R is an aromatic ring, heteroaromatic ring, or other carbon-containing fragment.

A reaction-energy source comprising UV light can be supplied to the reaction by, for example, one of the following representative procedures: (a) A sample comprising functionalizing reagent molecules and a substrate is placed in a well of a Rayonet Photochemical Reactor fitted with lamps which emit light of a wavelength suitable for converting the nitrenogenic group into a nitrene, such as 350-nm, 300-nm, or 254-nm lamps. The substrates and reagent molecules are irradiated at ambient temperature for several minutes under air. The duration of the irradiation can be adjusted to change the exposure dose. (b) The sample is irradiated through a high-resolution photomask, for example, by (but not limited to) projection UV lithography. (c) Photolysis is carried out in a KSM Karl Suss deep-UV contact aligner using a contact high-resolution photomask. It will be readily appreciated by persons skilled in the art that such procedures can also be generally used to provide the functionalizing reaction with photons of wavelengths other than UV.

A reaction-energy source comprising electrons can be supplied to the reaction by the following representative procedure: A sample is irradiated under vacuum by an electron or particle beam with an energy selected within the range 1–40 kV. (A representative electron-beam source is a JEOL 840A electron microscope modified for electron-beam lithography.) The beam may be stepped across the surface of the treated substrate to expose certain areas and not others. A dwell time at each step can be adjusted to change the exposure dose.

Particularly effective functionalizing reagents are selected from the group consisting of perhalophenyl azides (PHPAs), particularly perfluorophenyl azides (PFPAs) derived from 4-azido-2,3,5,6-tetrafluorobenzoic acid in which the carbonyl group is further activated through reactive ester, amide, acid halide, or mixed anhydride formation. For example, and not intended to be limiting, representative functionalized perfluorophenyl azides have the general structure:

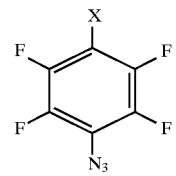

wherein X can be any of the following: CN, $CONH_2$, CHO, $CO_2Me$, COMe, $NO_2$, $CO_2H$, COCl, CO-Imidazole, CONHS, $CH_2OH$, $CH_2NH_2$, $COCH_2Br$, N-maleimido, NH-biotinyl, CONH—R (where R is a polypeptide moiety), CONH—X—S—S—Y—NH-biotinyl (where X and Y are spacer atoms and the S—S bond is reductively cleavable at a later stage), and CONHS—$SO_3Na$.

Representative activated PFPAs include (but are not limited to) the N-hydroxysuccinimide (NHS) ester A (also designated "NHS-PFPA", the p-nitrophenyl ester B, the 1-hydroxybenzotriazole ester C, the acyl imidazole D, the acid chloride E, the mixed anhydride F and the 2,2,2-trichloroethyl ester G:

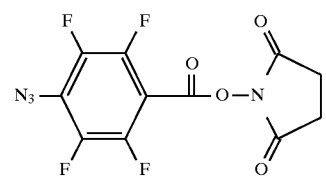

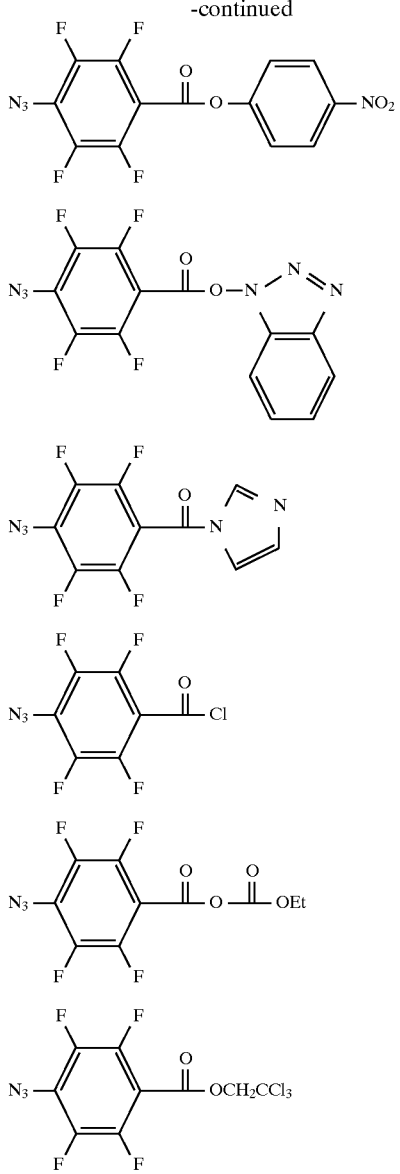

In addition to the foregoing candidate functionalizing reagents, it is possible to utilize other PFPAs having "spacers" situated between the reactive functional group and the PFPA moiety, such as:

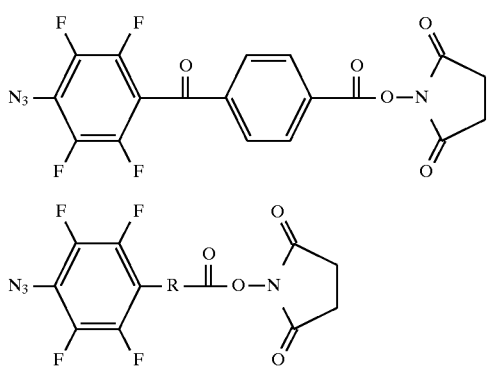

Other candidate aryl azides useful as functionalizing reagents are similar to the above examples except that another aryl moiety replaces the PFPA, such as:

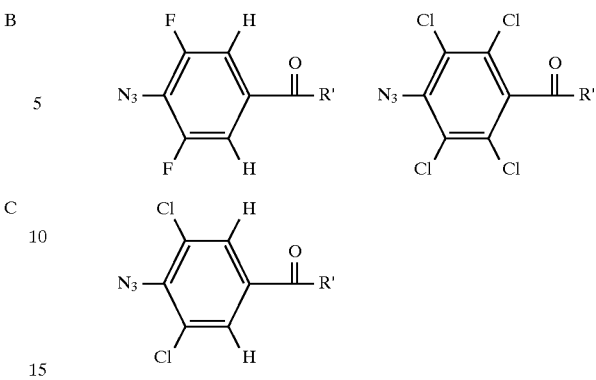

Candidate substrates that can be functionalized according to the present invention include, but are not limited to: polymeric substrates, graphite, metals, and siliceous materials; as well as silicon, gallium arsenide, and other semi-conducting materials.

In the case of siliceous substrates (e.g., glass, silica, mica, quartz) it is believed that the functionalizing reagents, when converted to corresponding nitrenes, react with SiO—H groups, Si—OH groups, or Si—OSi groups on the substrate surface.

In the case of graphite and other allotrophic forms of elemental carbon, it is believed that the functionalizing reagents, when converted to the corresponding nitrenes, react with carbon rings on the substrate surface.

Polymeric substrates that can be functionalized according to the present invention include virtually any polymeric material comprising polymer molecules possessing —CH groups, and/or —NH groups, and/or —OH groups and/or —C=C— sites. Such polymeric substrates include, but are not limited to:

(a) saturated polyolefins as exemplified by polyethylene, polyvinyl chloride, polytetrafluoroethylene, polypropylene, polybutenes, and copolymers thereof;

(b) acrylic resins such as polymers and copolymers of acrylic acid, methacrylic acid [eg., poly(methylmethacrylate), poly(hexylmethacrylate)], and acrylonitrile;

(c) polystyrene and its analogues such as poly(p-chlorostyrene) and poly(p-hydroxystyrene);

(d) unsaturated polyolefins such as poly(isoprene) and poly(butadiene);

(e) polyimides such as polyimide(benzophenone tetracarboxylic dianhydride/tetraethylmethylenedianiline);

(f) polyesters such as poly(trimethylene adipate) and poly(hexymethylene sebacate);

(g) conjugated and conducting polymers such as poly(3-alkylthiophene), poly(3-alkylpyrrole), and polyaniline;

(h) inorganic polymers such as poly(aryloxyphosphazene), poly[bis(trifluoroethoxy)phosphazene], polysilanes, and polycarbosilanes, siloxane polymers, and other silicon-containing polymers;

(i) organic metals (i.e., organic polymers with metallic properties) such as polycroconaines and polysquaraines, as described in *Chemical and Engineering News* (Aug. 31, 1992), p. 8.

(j) organometallic polymers such as palladium poly-yne and ferrocene-containing polyamides; and (k) polysaccharides such as cellulose fibers, chitin, and starch.

Functionalizing substrates according to the method of the present invention requires that molecules of the functionalizing reagent and the substrate be brought into "reactive proximity"; i.e., brought together sufficiently closely so as to undergo a functionalizing reaction when exposed to the reaction-energy source. One way materials, such as polymers, can be functionalized is to prepare a solution comprising the material and the functionalizing reagent. Another way is to prepare a suspension or mixture comprising the functionalizing reagent and substrate particles or substrate agglomerations. Yet another way is to apply the functionalizing reagent (such as a solution of the functionalizing reagent in a solvent capable of absorbing into the substrate) to a surface of the substrate, then allowing the functionalizing reagent to absorb into the substrate.

Functionalization of a substrate can occur in one or more stages, depending upon various factors such as the particular material to be functionalized; the form of the material (i.e., solution, particulate suspension, non-fluid mass); the functional group(s) to be attached to the polymer molecules; the necessity to protect the functional groups from undesired reactions during reaction of the functionalizing reagent with the polymer molecules; and on other matters.

For example, in a one-stage functionalization, substrate molecules and molecules of a functionalizing reagent each having a nitrenogenic group and a desired functional group are brought into reactive proximity. Upon exposure to a reaction-energy source, the nitrenogenic groups are converted to nitrenes which react with —CH, —NH, —OH, —C═C—, C—C, and other groups on the substrate molecules reactive with nitrenes, thereby covalently bonding the functional groups to the substrate molecules. The functional groups typically do not require additional chemistry performed on them to confer the desired useful property to the resulting functionalized substrate.

In a two-stage functionalization protocol, each stage involves a different functionalizing reagent. The first stage involves a first functionalizing reagent, such as, without limitation, an NHS-PFPA. The first functionalizing reagent is converted during the course of the first-stage reaction to a nitrene intermediate. During the first stage using, for example, a polymeric substrate, the NHS active-ester groups on the NHS-PFPA molecules become covalently attached to surface polymer molecules by a reaction that can be generally indicated as shown below in Scheme 1:

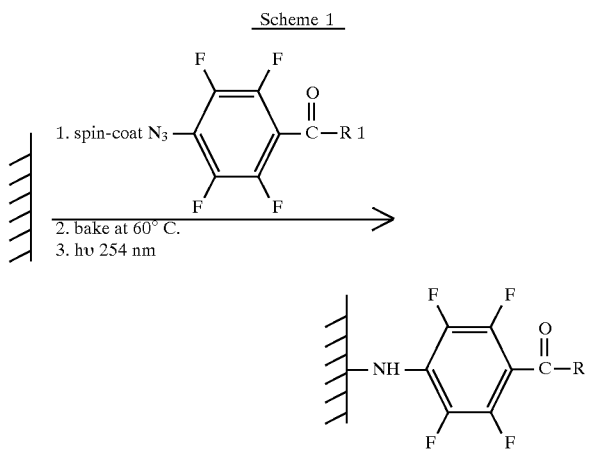

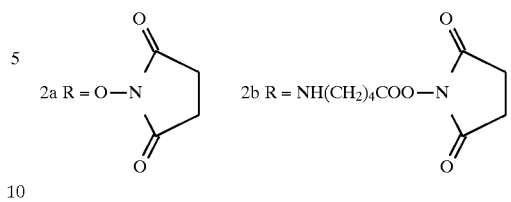

As another example of a two-stage functionalization reaction, the first stage may involve a first functionalizing reagent such as an NHS-PFPA compound. Upon exposure to a reaction-energy source, the azide group of the PFPA portion is converted to a nitrene intermediate that reacts with polymer molecules. Thus, the NHS active-ester groups on the NHS-PFPA molecules become covalently attached to the polymer molecules by a reaction that can be generally indicated as shown in Scheme 2 (wherein a polymer molecule is represented by a circumscribed P):

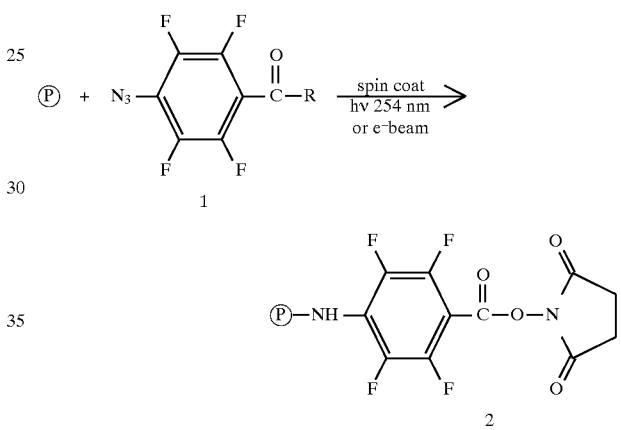

Thus, this first-stage reaction requires generation of a highly reactive nitrene intermediate derived from the NHS-PFPA 1 by exposure of the NHS-PFPA to a reaction-energy source.

As still another example of a two-stage reaction protocol, the first stage can be performed by interspersing molecules of a first functionalizing reagent depthwise into the substrate mass, such as by first forming a fluid solution or suspension comprising the polymer and the first functionalizing reagent; forming the fluid into a desired shape; then converting the fluid into a product having a rigid form. The reaction-energy source is then applied to the rigid product to covalently bond the first functionalizing reagent to the polymer molecules. Subsequently, during the second stage, the second functionalizing reagent is applied to a surface of the rigid product.

As can be seen by the preceding examples, the NHS-ester portions of the PFPAs do not participate in this first-stage chemistry. Rather, the NHS-esters, after being transferred to the surface molecules, are utilized in second-stage chemistry, discussed below.

In the second stage, the NHS esters readily react with molecules of a second functionalizing reagent. The second functionalizing reagent is selected from a group consisting of molecules possessing primary or secondary nucleophilic species, such as, but not limited to, amines, sulfhydryls, and/or hydroxyls. Reaction of NHS-esters with primary amines proceeds via amide formation as shown in Scheme 3:

Scheme 3

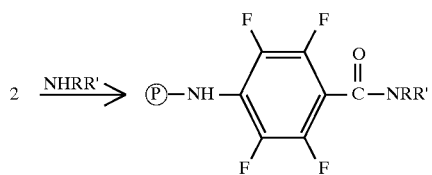

wherein compounds 2a and 2b are as shown in Scheme 1. Reaction of NHS-esters with hydroxyls proceeds via ester formation, as shown in Scheme 4:

Scheme 4

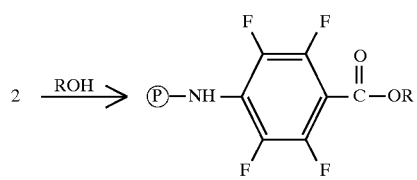

wherein compounds 2a and 2b are as shown in Scheme 1.

Since many types of biological molecules possess nucleophilic groups, such as amine and/or hydroxyl groups, these molecules can serve as functionalizing reagents adapted for reaction in a second-stage functionalization reaction with NHS-esters covalently bonded to the surface molecules in a first-stage functionalization reaction. Thus, it is possible to attach any of a wide variety of molecules, including macromolecules such as proteins, nucleic acids, carbohydrates, and various other molecules, to substrates and/or surfaces thereof using methods according to the present invention.

By practicing the methods of the present invention, it also is possible to first prepare nitrenogenic derivatives of molecules (such as biomolecules, drugs, analytes, catalysts [including transition metals], and diagnostic agents) to be attached to the substrate, bring the derivatives into reactive proximity or apply the derivatives to a surface of the substrate, then expose the derivatives or treated surface to a reaction-energy source to cause the nitrenogenic derivatives to covalently bond to the substrate and/or surface molecules via nitrene intermediates. It is necessary for the nitrenogenic moiety to be structurally constrained such that the nitrene cannot readily react with another part of the same molecule. For instance, with NHS-PFPA functionalizing reagents the 4-position of the phenyl ring is the preferred position for the azide group.

To convey the scope of the present invention without intending in any way to be limiting, the following representative functionalizations according to the present invention are provided:

(a) Carcinogenic or mutagenic polycyclic aromatic hydrocarbons can be attached to substrates and/or substrate surfaces to create a "carcinogenic" substrate and/or "carcinogenic" substrate surface. Candidate polycyclic hydrocarbons include, without limitation, ethidium compounds and various pyrene compounds (such as 1-pyrenemethylamine and 6-aminochrysene). It is also possible, when attaching such compounds to a substrate, to employ "spacer groups" serving to "lift" the hydrocarbon from the substrate surface. A representative spacer-containing hydrocarbon is the primary amine derived from 1-pyrenebutyric acid. Such reactions can be depicted generally as shown in Scheme 5:

Scheme 5

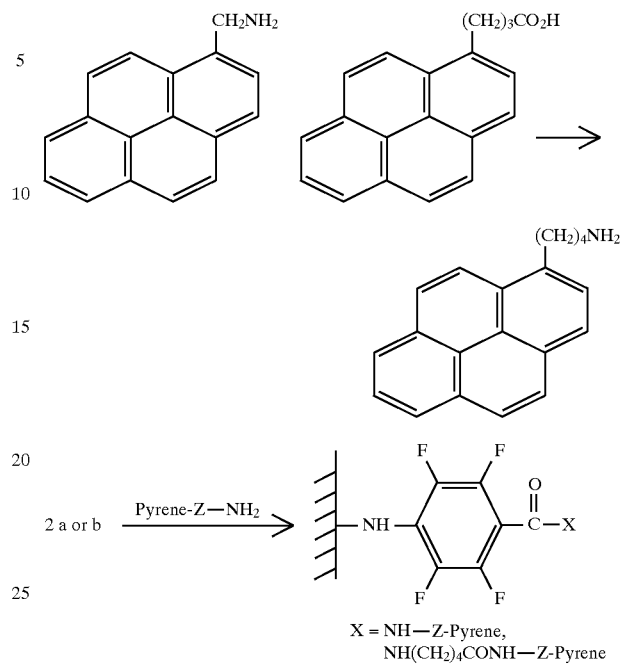

wherein 2a and 2b are as shown in Scheme 1 and Z represents a spacer group.

(b) The hydrophobicity of a substrate and/or substrate surface can be altered, after attachment of NHS-ester groups to the substrate surface in a first-stage reaction (via a nitrene intermediate). Subsequent reaction of the NHS-ester groups with relatively non-polar compounds, such as long-chain aliphatic amines, including, but not limited to, 1-aminohexadecane, occurs in a second-stage reaction. Such a reaction can be generally depicted as shown in Scheme 6:

Scheme 6

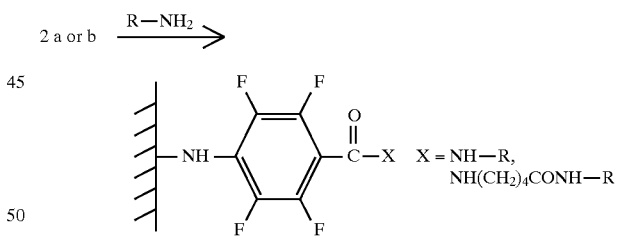

wherein R is a chain of hydrophobic atoms such as, for example, $C_{12}H_{25}-$, oleyl, octadecyl, 3-β-aminocholestane, or hexyldimethylsilyl; and 2a and 2b are as shown in Scheme 1.

(c) The hydrophilicity of the substrate and/or substrate surface can be altered, after attachment of NHS-ester groups to the substrate and/or substrate surface in a first-stage reaction (via a nitrene intermediate), by reaction of the NHS-ester groups with highly polar molecules, such as hydroxyl- or amine-possessing molecules, in a second-stage reaction. Examples of amine-possessing polar molecules include (but are not necessarily limited to): glucosamine, ethanolamine, polyethyleneimine (protonated at pH 7), polylysine (also protonated at pH 7), glycerol, and other polyhydroxy compounds. Such reactions can be generally depicted as shown in Scheme 6 but wherein R is $HOCH_2CH_2$—, or $NH_2(CH_2CH_2NH—)_n—CH_2CH_2$—; and 2a and 2b are as shown in Scheme 1. For polyalcohols, such reactions can be generally depicted as shown in Scheme 7:

Scheme 7

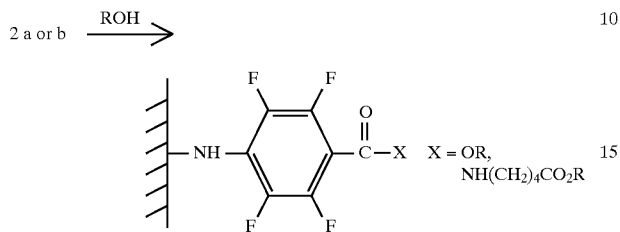

wherein R is, for example, CH—CHOH—$CH_2OH$; and 2a and 2b are as shown in Scheme 1.

(d) The substrate can be made surface-active in regions where NHS-ester groups have already been attached to the substrate surface in a first-stage reaction. The reaction to make the substrate surface-active proceeds by a second-stage reaction employing any of various aminated or hydroxylated "detergent" molecules such as, for example, 1-amino-dodecanoic acid. At pH 7 and after attachment of this compound to the substrate, the carboxyl group is ionized and the compound extends away from the substrate surface as a long hydrophobic tail terminating in a polar carboxylate anion. Such reactions can be generally depicted as shown in Scheme 8:

Scheme 8

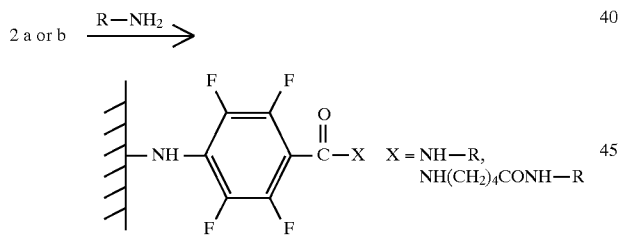

wherein R is —$(CH_2)_n$—$CO_2H$; and 2a and 2b are as shown in Scheme 1.

(e) Enzymes can be attached to a substrate and/or substrate surface previously functionalized in a first-stage reaction with, for example, an NHS active ester. The subsequent second-stage reaction proceeds by a second-stage reaction of with, for example, a lysine amino group present on polypeptide molecules with the NHS active ester. A representative reaction is depicted as shown in Scheme 9:

Scheme 9

-continued
Scheme 9

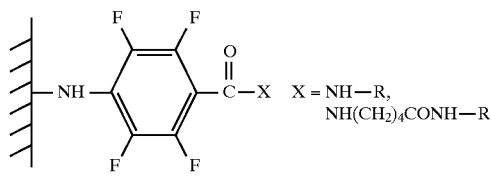

wherein R—$NH_2$ represents a lysine residue on a polypeptide such as an enzyme (e.g., horseradish peroxidase), lectin, or antibody; and 2a and 2b are as shown in Scheme 1.

(f) Antibodies, lectins, and other proteins can also be attached to substrates by functionalizing reactions similar to such reactions for attaching enzymes. Such attached molecules can then be used, for example, as highly selective sensing agents in biosensors.

(g) Specialized molecules can be attached to a substrate surface(s) to potentiate the biocompatibility of substrates, control the wettability of the substrate surface(s), or to alter the ability of living cells to adhere to the substrate surface(s).

(h) Substrates or substrate surfaces can be biotinylated in a one or two-stage reaction, followed by treatment of the biotinylated surface with, for example, a derivatized avidin or streptavidin. The avidin or streptavidin are thus used as bridging units for subsequent attachment of other biomolecules to the surface. Representative reactions are as follows:

TWO STAGE REACTION
Scheme 10

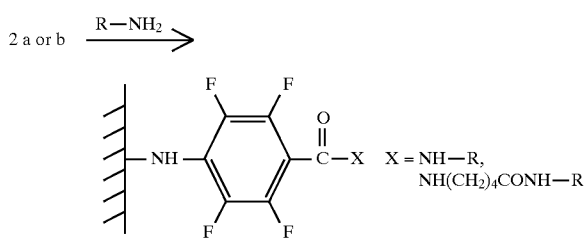

wherein 2a and 2b are as shown in Scheme 1 and $RNH_2$ represents the amino group of N-biotinylhexylenediamine:

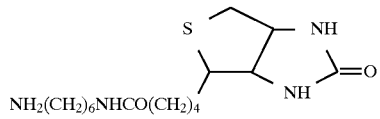

A one-stage reaction is exemplified by coating the substrate with the PFPA derivatives of biotin (see Scheme 13, compound 5), followed by exposure to photolysis or an electron beam.

To further illustrate and describe the present invention, the following examples are provided. These examples are intended to exemplary only, and should not be construed to limit the invention to the particular aspects described therein.

EXAMPLE 1

In this Example, we modified the surface of a representative polymer (polystyrene) using N-hydroxysuccinimidefunctionalized (NHS-functionalized) perfluorophenyl azides (PFPAs) 1a and 1b (Scheme 11).

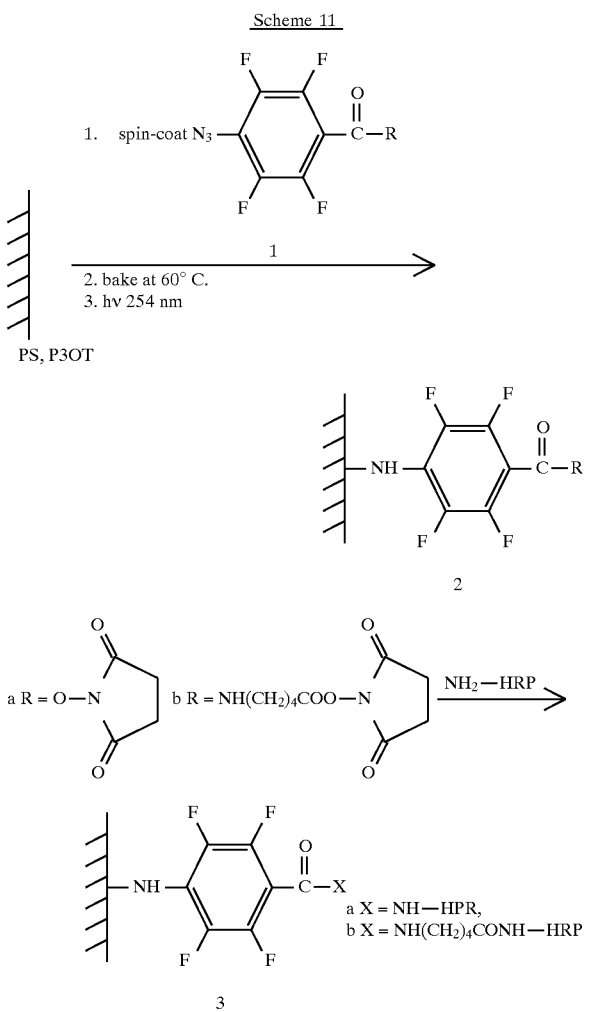

PFPA 1a is described in Keana et al., *J. Org. Chem.* 55:3640–3647 (1990).

PFPA 1b was prepared by N-acylation of 5-aminopentanoic acid with 4-azido-2,3,5,6-tetrafluorobenzamido) pentanoic acid (melting point (mp): 160°–161° C.; High-resolution mass spectrometry (HRMS) calculated for $C_{12}H_{10}F_4N_4O_3$: 334.0687; found m/z: 334.0710) which was then coupled with NHS in the presence of dicyclohexylcarbodiimide to yield N-succinimidyl 5-(4-azido-2,3,5,6-tetrafluorobenzamido)pentanoate 1b (mp: 93°–95° C.; HRMS calculated for $C_{16}H_{13}F_4N_5O_5$: 431.0850; found m/z: 431.0866).

A glass disc was spin-coated with a solution of 5 wt % polystyrene (PS) in xylene to form a film on the disk about 0.5 μm thick, as described in Cai et al., *Chem. Mater.* 4:879–884 (1992). The PS film was then spin-coated with a solution of 0.5 wt % of 1a or 1b in nitromethane and baked at 60° C. for 20 minutes. The baking step removed residual solvent and likely facilitated the diffusion of surface-deposited PFPAs into the PS films.

Subsequent photolysis of the film resulted in complete decomposition of the azido groups as indicated by FTIR (Fourier-Transform Infrared) spectroscopy. Photolysis was carried out in a Rayonet photoreactor with 254-nm lamps for 5 minutes at ambient temperature under air. FTIR was performed with a control sample using a NaCl disc as the support. Covalent attachment of the NHS PFPA esters to the PS surface yielded 2a and 2b (Scheme 11), respectively. We believe that the reaction occurred via C—H bond insertion of the highly reactive nitrene intermediate derived from 1a or 1b. See, Keana et al., *J. Org. Chem.* 55:3640–3647 (1990); Leyva et al., *J. Org. Chem.* 54:5938–5945 (1989); and Poe et al., *J. Am. Chem. Soc.* 114:5054–5067 (1992).

Since NHS active esters react readily with primary and secondary amines to form amides, Anderson et al., *J. Am. Chem. Soc.* 86:1839–1842 (1964), a variety of primary and secondary amine-containing reagents including biomolecules can be attached to the polymer surface by this method.

EXAMPLE 2

In this Example, we immobilized horseradish peroxidase (HRP, Sigma) on PS films modified by PFPA-NHS as described in Example 1. Compounds are shown in Scheme 11.

The films 2a and 2b were incubated in a 50-μM solution of HRP in $NaHCO_3$ buffer (pH 8.2) at 25° C. for 3 hours, Brinkley, *Bioconjugate Chem.* 3:2–13 (1992), followed by a thorough rinsing with phosphate buffer (pH 7.0). The enzyme activity of the resulting immobilized HRP films 3a and 3b was determined spectrophotometrically at 420 nm and 25° C. in phosphate buffer according using 2,2'-azino—bis(3-ethylbenzthiazoline-6-sulfonic acid) diammonium salt (ABTS) and hydrogen peroxide (1.8 mM ABTS/0.8 mM $H_2O_2$). Groome, *J. Clin. Chem. Clin. Biochem.* 18:345–349 (1980). Making the reasonable assumption that the immobilized HRP has the same activity as the native HRP, Nakane et al., *J. Histochem. Cytochem.* 22:1084–1091 (1974), the extent of immobilization of HRP was calculated to be 0.5±0.1 ng/mm² for 3a and 1.0±0.2 ng/mm² for the spacer-containing analogue 3b, indicating reasonable immobilization efficiencies.

An HRP molecule has a molecular weight around 40,000 daltons and a radius of 2.67 nm in the hydrated state. Steiner et al., *Eur. J. Biochem.* 82:543–549 (1978). Assuming a flat polymer surface, the surface coverage of a monolayer of HRP is 2.7 ng HRP per mm².

In control experiments, polymer films not spincoated with PFPA were similarly baked, irradiated, and incubated with HRP solution. The resulting films showed no HRP activity.

EXAMPLE 3

In this Example, we performed surface modification of the conducting polymer, poly(3-octylthiophene) (P3OT), Cai et al, *J. Mol. Electron.* 7:63–68 (1991), in a manner similar to the methodology described in Examples 1 and 2. The extent of immobilization of HRP on PFPA-NHS-modified P3OT films was 0.2±0.1 ng/mm² with film 3a (Scheme 11) and 0.3±0.1 ng/mm² with film 3b.

EXAMPLE 4

In this Example, we performed surface modification of a PS surface using PFPAs in combination with photolithography to generate micron-size patterns on the surface of the polymer. Compounds are as shown in Scheme 11.

A PS film was spin-coated with a nitromethane solution of 1a, baked as described above, and irradiated through a high-resolution photomask having a minimum feature size of 0.5 μm. Photolysis was carried out in a KSM Karl Suss deep-UV contact aligner. The film was then dipped in nitromethane for 20 seconds, air dried, and allowed to react with a solution of 5-(aminoacetamido)fluorescein (Molecular Probes, Inc., Eugene, Oregon) in ethanol (4 mg/mL) at 25° C. for 1 hour followed by thorough rinsing with ethanol.

FIG. 1 shows the resulting micron-size patterns as observed under a fluorescence microscope, further demonstrating this new surface modification strategy. The smallest features (0.5 µm) are resolved but are slightly broadened, probably owing to diffraction effects.

As a control, a PS film without spin-coating NHS active ester 1a was photolyzed, developed and treated with 5-(aminoacetamino)fluorescein. No fluorescent patterns were observed under the fluorescence microscope (data not shown).

EXAMPLE 5

In this Example we modified the surface of a preformed polymer microstructure. Compounds are as shown in Scheme 11.

A micron-scale pattern of PS, which had previously been fabricated on a silicon wafer using deep-UV lithography, was dipped in a nitromethane solution of 1a for 10 seconds, baked, and photolyzed as described above. The sample was then immersed in a solution of N-(5-aminopentyl) biotinamide (Molecular Probes, Inc., Eugene, Oreg.) in DMF (1 mg/0.2 mL) for 4 h, and washed with DMF followed by ethanol. Taking advantage of the strong affinity of avidin for biotin (Green, *Adv. Protein Chem.* 29:85–133 (1975); Heitzmann et al., *Proc. Nat. Acad. Sci. USA* 71:3537–3541 (1974)), fluorescein-avidin (Molecular Probes, Inc., Eugene, Oreg.) was attached to the surface by incubating the wafer in a solution of the fluorescent protein in pH 8.2 buffer (3.2 mg/0.5 mL) for 4 h.

Figure 2A:
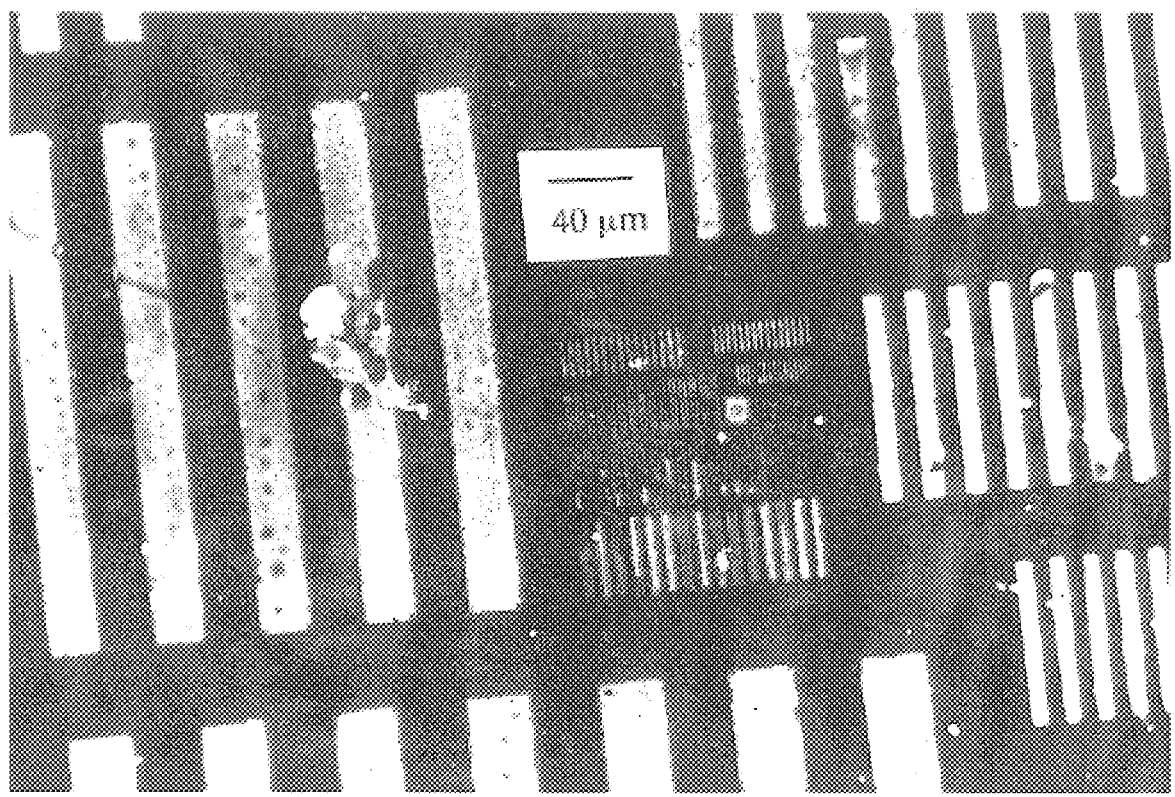
FIG. 2A is a photomicrograph of fluorescent protein formed by treating preformed polystyrene patterns with a PFPA compound (compound 1a in Scheme 1) followed by photolysis, then treating with N-(5-aminopentyl) biotinamide followed by fluorescein-avidin, as described in Example 5.
Figure 2B:
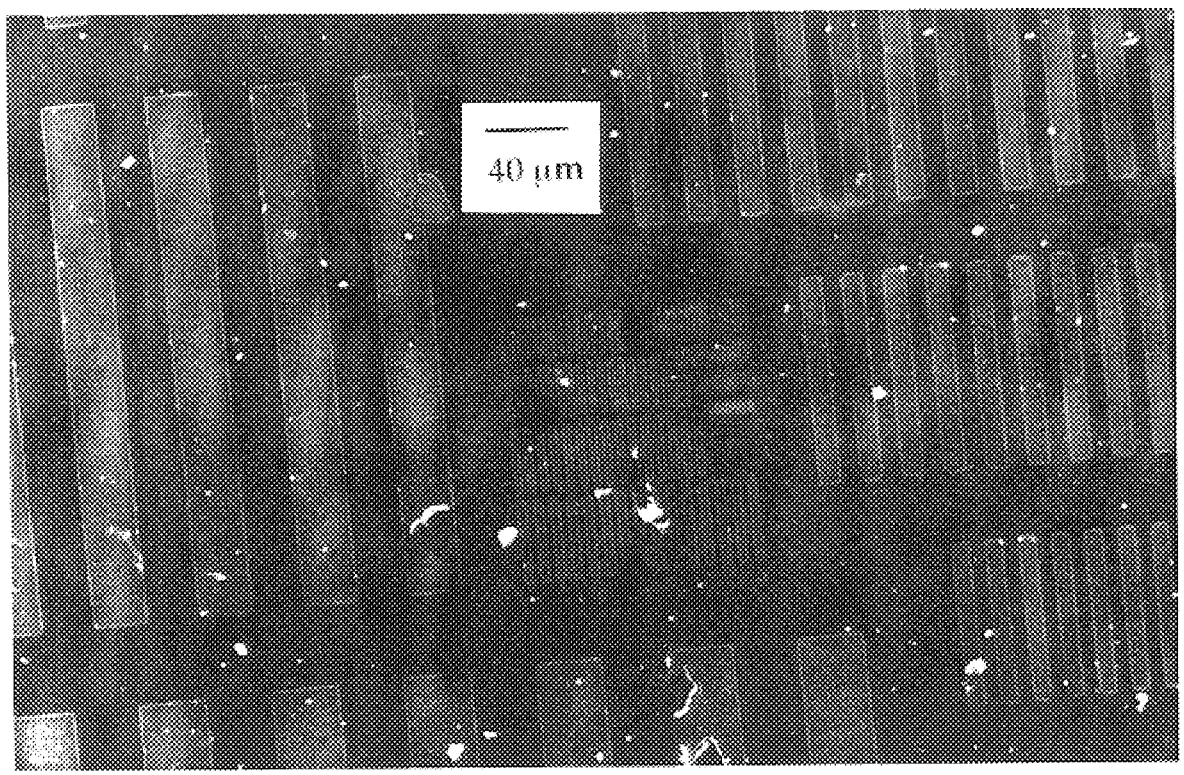
FIG. 2B is a photomicrograph of an experimental control wherein polystyrene patterns were treated with fluorescein-avidin only, as described in Example 5.

The resulting micron-size patterns are shown in FIG. 2A and the experimental control is shown in FIG. 2B. These results indicate that the biotin-avidin-fluorescein assembly became covalently attached to the preformed PS microstructure.

EXAMPLE 6

In this Example, we functionalized the surface of graphite. A piece of pyrolytic graphite was freshly cleaved using transparent adhesive tape and coated with a solution of 0.5% w/w N-hydroxysuccinimidyl 4-azidotetrafluorobenzoate (NHS-PFPA) in dry nitromethane by spinning at a speed of 1000 rpm. The coated graphite was baked at 60° C. for 20 minutes and irradiated for 5 minutes using 254-nm lamps at ambient temperature under air. The graphite was then incubated in a 50-µM solution of horseradish peroxidase (HRP) in NaHCO₃ buffer (pH 8.2) at 25° C. for 3 hours and rinsed thoroughly with phosphate buffer (pH 7.0).

The enzymatic activity of the functionalized graphite was determined spectroscopically at 420 nm and 25° C. in phosphate buffer using 2,2'-azino-bis(3-ethylbenzthiazoline-6-sulfonic acid) diammonium salt (ABTS) and hydrogen peroxide (1.8 mM ABTS/0.8 mM H₂O₂). Assuming that the immobilized HRP had the same activity as the native HRP, the extent of immobilization of HRP was 2.1 ng/mm².

A control experiment was performed as follows: A piece of freshly cleaved graphite was similarly baked, irradiated, and incubated with HRP solution. The enzyme-activity of the control was determined to be 0.4 ng HRP/mm². Thus, the control was not treated with NHS-PFPA.

Samples and controls were examined using atomic-force microscopy (AFM). The atomic-force microscope was operated in air at ambient temperature.

Figure 3A:
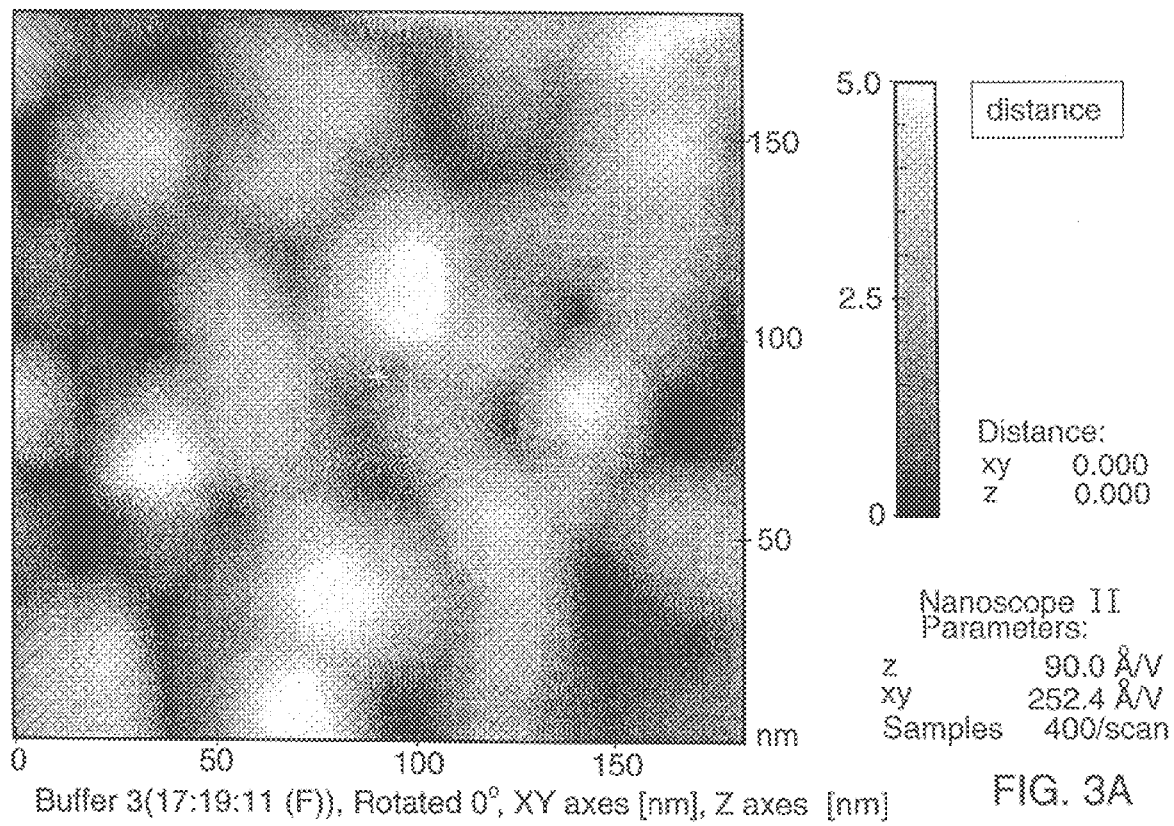
FIG. 3A is an image obtained with an atomic-force microscope of a freshly cleaved graphite surface functionalized first with NHS-PFPA, then with horseradish peroxidase, as described in Example 6.
Figure 3B:
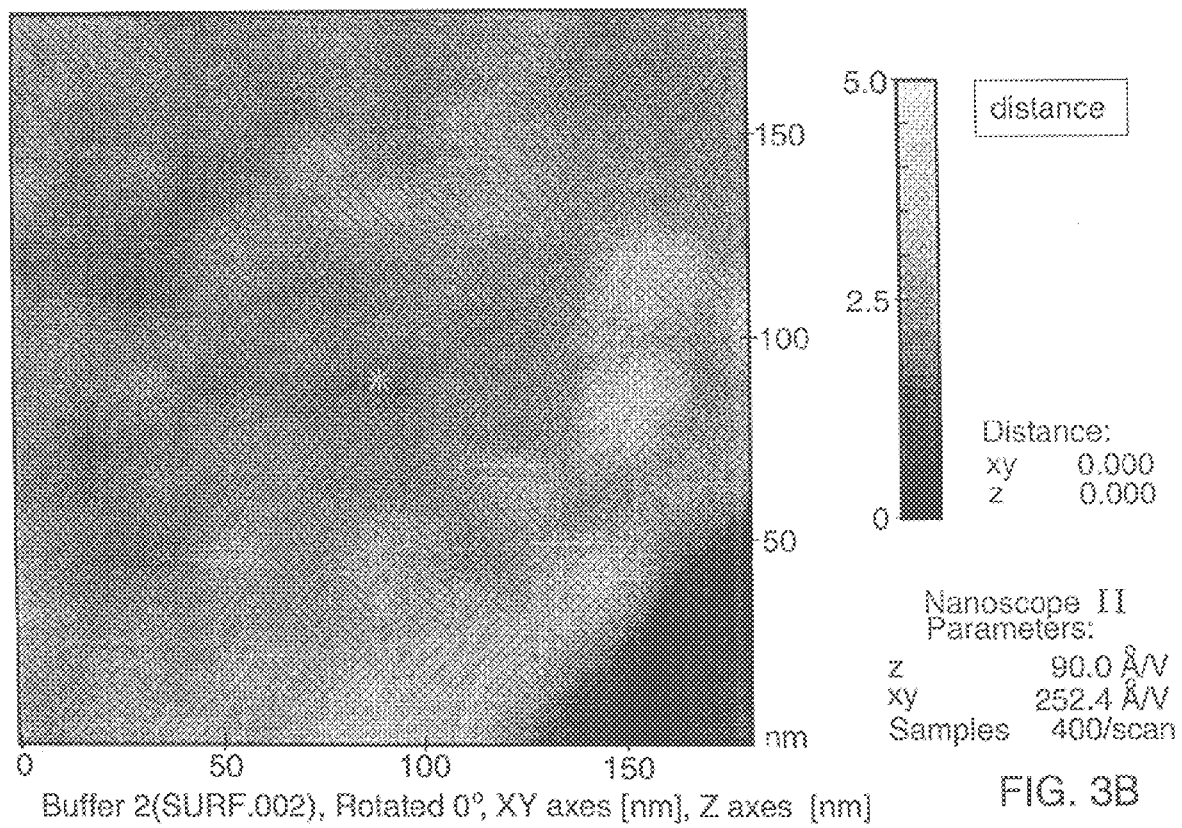
FIG. 3B is an atomic-force microscope image of an experimental control wherein a freshly cleaved graphite surface was treated with horseradish peroxidase but not with NHS-PFPA, as described in Example 6.

A representative AFM image of the sample is shown in FIG. 3A and of the control in FIG. 3B. In FIG. 3A, bright spheres correspond to immobilized HRP molecules. In FIG. 3B, only a few faint spheres were seen, indicating much less immobilization of the HRP molecules to the control surface.

Therefore, the NHS-PFPA is necessary to achieve substantial covalent attachment of HRP to the graphite surface.

EXAMPLE 7

The chemistry of this Example is illustrated in Scheme 12, wherein two photoactive biotins, PFPA-biotins 3 and 5 were prepared. These photoactive biotins could be used to functionalize a polymer surface with biotin groups. Such biotinylated surfaces can be further reacted so as to attach biomolecules to the substrate through biotin-binding proteins such as avidin.

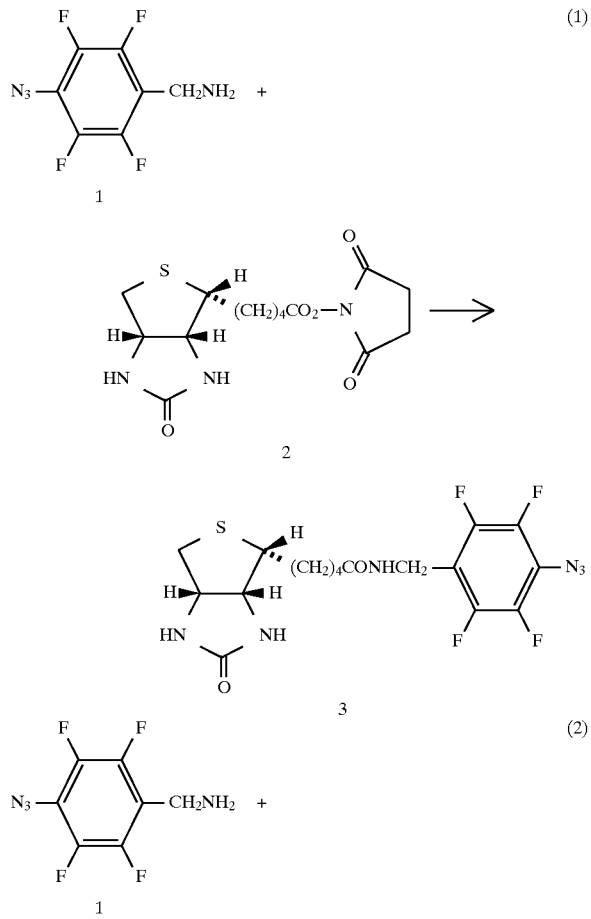

Scheme 12

-continued
Scheme 12

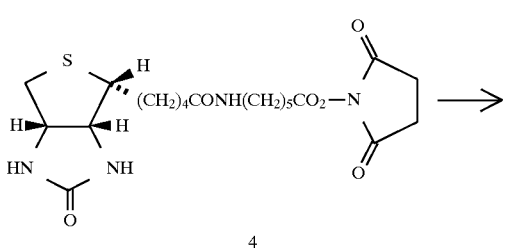

4

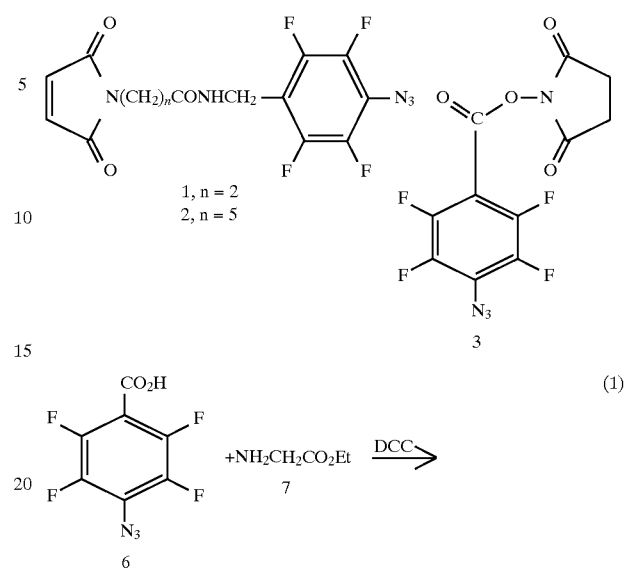

Scheme 13

Synthesis of N-4-azido-2,3,5,6-tetrafluorobenzyl biotinamide (3) was performed as follows: To a solution of 33 mg (0.097 mmol) N-succinimidyl-D-biotin in 0.5 mL of DMSO-$d_6$ was added 27 mg (0.12 mmol) of 4-azido-2,3,5,6-tetrafluorobenzylamine. The resulting solution was maintained at room temperature for 0.5 hours, after which NMR revealed completion of the reaction. The solution was added dropwise into 10 mL water to form a precipitate. The precipitate was filtered, washed with water, and dried to yield 36.8 mg (85%) of 3 as an almost colorless solid having a mp=164°–165° C. $^1$H-NMR (CDCl$_3$+DMSO)–$d_6$): 1.157 (q,2), 1.40 (m,4), 1.950 (t,2), 2.87 (m,2), 4.01 (m,1), 4,20 (m,3), 5.41 (m,2), 7.53 (m,1). IR (KBr): 3454, 3290, 2931, 2161, 2125, 1704, 1654, 1549, 1493, 1420, 1239, 1054 cm$^{-1}$.

Synthesis of N-4-azido-2,3,5,6-tetrafluorobenzyl-6-(biotinamido)hexanamide (5) was performed as follows: To a solution of 49.2 mg (0.108 mmol) of N-succinimidyl-6-(biotinamido)hexanoate in 0.6 mL of dry DMF was added 32 mg (0.14 mmol) of 4-azido-2,3,5,6-tetrafluorobenzylamine. The solution was stirred at room temperature for one hour, then added dropwise into 10 mL water. The resulting precipitate was filtered, washed by water, and dried to yield 60.1 mg (99%) of 5 as a colorless solid with mp=160°–161° C. $^1$H-NMR (CDCl$_3$+DMSO–$d_6$): 0.98 (m,2), 1.14 (m,4), 1.31 (m,6), 1.85 (m,4), 2.4–2.5 (m,2), 2.8 (m,3), 3.92 (m,1), 4.10 (m,3), 5.52 (s,1), 5.56 (s,1), 6.76 (m,1), 7.56 (m,1). IR (KBr): 3438, 3301, 2935, 2162, 2177, 1700, 1652, 1547, 1499, 1416, 1239, 1054 cm$^{-1}$.

EXAMPLE 8

This Example concerns the synthesis of several PFPA-based cross-linkers capable of functionalizing polymers. In particular, a group of NHS-ester functionalized PFPAs with different linker lengths between the NHS ester group and the PFPA group were synthesized. These functionalized PFPAs were particularly adapted for photo-cross-linking amino groups in biopolymers to proximally located chemical groups and for functionalization of polymers in general. The overall chemistry is diagrammed in Scheme 13.

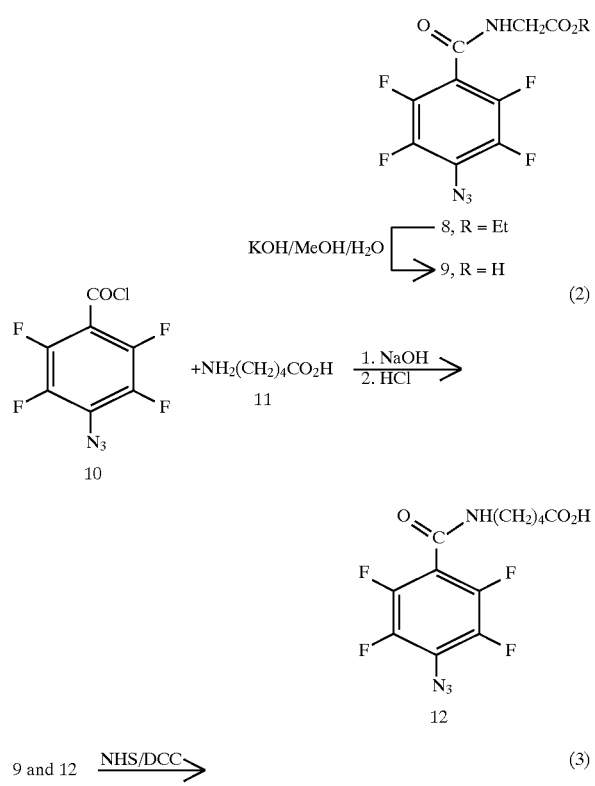

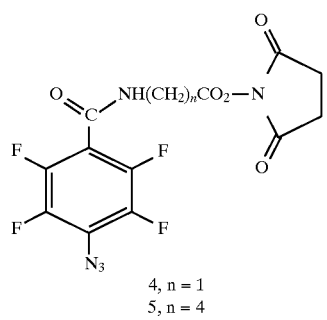

The chemistry utilizes maleimide-containing PFPAs 1 and 2 which were previously used to map cysteine residues introduced into ATPase by mutation, yielding a photo-cross-linking yield as high as 50 percent. Aggeler et al., *Biochemistry* 31:2956–2961 (1992).

The NHS-containing PFPAs 4 and 5 are particularly adapted for cross-linking of an amino group in a polypeptide chain to a proximally located chemical group by means of a photochemical —CH or —NH insertion reaction. These PFPAs can also be used to modify polymers with the NHS groups which can then be reacted with amino-containing reagents for introducing other functional groups into the polymers.

In Scheme 13, reaction of acid 6 and the glycine ethyl ester 7 with dicyclohexylcarbodiimide (DCC) as coupling reagent produced the amide 8 as follows: A mixture of 217 mg (1.55 mmol) of glycine ethyl ester hydrochloride and 158 mg (1.56 mmol) of triethylamine in tetrahydrofuran (7 mL) was stirred for 20 minutes. Afterward, 369 mg (1.57 mmol) of 4-azido-2,3,5,6 tetrafluorobenzoyl acid 6 and 324 mg DCC was added. The mixture was stirred overnight and filtered. The filtrate was evaporated and the residue dissolved in 20 mL of ethyl acetate. The solution was then dried and filtered. The filtrate was washed with 0.1N HCl (2×10 mL), 5% NaHCO$_3$ (2×10 mL), and water (2×10 mL). The solution was dried and evaporated to yield a solid that was purified by preparative TLC to yield 160 mg (32% yield) of 8 as a colorless solid with a mp=85°–86° C. $^1$H NMR: 1.321 (t,3, J=7.13), 4.239 (d,2, J=4.82), 4,273 (q,2, J=7.13), 6.540 (mb,1). IR: 2128, 1744, 1686, 1649, 1523, 1488, 1225, 1001 cm$^{-1}$. Anal. calcd for C$_{11}$H$_8$F$_4$N$_4$O$_3$: C, 41.26; H, 2.52; N, 17.50. Found: C, 41.46; H, 2.37; N, 17.66.

Subsequent hydrolysis produced the acid 9 as a solid in 31% overall yield, as follows: To a solution of 60 mg of 8 in 0.5 mL methanol was added 0.4 mL of a solution of 2.5% aqueous NaOH. The resulting solution was stirred for one hour. The solution was then acidified to pH<1 using 2N HCl. The precipitate was filtered and dried to yield 23 mg of 9 as a white solid. The filtrate was extracted by THF/CHCl$_3$ (1:1, 3×3 mL) and the extract was dried and evaporated to yield a further amount (32 mg) of 9 as a white solid (combined yield 55 mg, 99%) with a melting point of 147°–148° C. $^1$H-NMR (CDCl$_3$+DMSO-d$_6$): 4.339 (d,2, J=4.80), 6.527 (m,1). MS: 292 (2, M$^+$), 264 (20, M$^+$-N$_2$), 190 (20, NC$_6$F$_4$CO), 162 (100, NC$_6$F$_4$).

Reaction of the acyl chloride 10 with 5-aminopentanoic acid 11 under basic conditions followed by acidification produced the acid 12, as follows: To a solution of 238 mg (2.03 mmol) of 5-aminopentanoic acid 11 in 50% aqueous NaOH (0.4 mL) and 2.6 mL water was added 239 mg (0.942 mmol) of 4-azido-2,3,5,6-tetrafluorobenzoyl chloride 10. A precipitate was observed immediately. The mixture was stirred for 5 min and diluted with 3 mL water. The mixture was then stirred for another 15 minutes and acidified to pH<1 using 2-N HCl. The precipitate was filtered and washed with 0.1N HCl (1 mL) and 2 mL water, and dried to yield 231 mg of solid. The solid was washed using 1 mL ether and crystallized in a mixture of tetrahydrofuran and ether to yield 171 mg (54% yield) of 12 as a colorless solid with mp=160°–161° C. $^1$H-NMR (CDCl$_3$+DMSO-d$_6$): 1.753 (m,4), 2.540 (t,2, J=6.73), 3.504 (q,2, J=5.90), 6.1 (m,1). MS: 334 (5, M$^+$), 317 (4, M$^+$—OH), 306 (40, M$^+$—N$_2$), 190 (15, NC$_6$F$_4$CO), 162 (100, NC$_6$F$_4$). High-resolution MS calc'd for C$_{12}$H$_{10}$F$_4$N$_4$O$_3$: 334.0687; found: 334.0710.

The NHS-active esters 4 and 5 were prepared by reaction of acids 9 and 12 with N-hydroxysuccinimide in the presence of DCC, respectively. In particular, to prepare 4, a solution of 39.3 mg (0.134 mmol) of 9, 29.3 mg (0.142 mmol) of DCC, and 16.6 mg of NHS in 0.5 mL THF was stirred at 25° C. overnight. The resulting mixture was filtered. The filtrate was evaporated to yield a solid that was redissolved in 1 mL CH$_2$Cl$_2$. The resulting mixture was filtered. The filtrate was evaporated to yield 42 mg (80% yield) of 4 as a colorless solid. The analytical sample was obtained via recrystallization in acetone/hexane as a colorless solid having a mp=145°–146° C. $^1$H-NMR: 2.883 (s,4), 4,637 (d,2, J=5.40), 6.548 (mb,1). IR: 2129, 1792, 1748, 1718, 1699, 1649, 1520, 1489, 1204 cm$^{-1}$. MS: 389 (8, M$^+$), 275 (60, M$^+$—NHS), 247 (27, M$^+$—NHS—N$_2$), 218 (65, M$^+$—CONHS—N$_2$—H), 190 (45, NC$_6$F$_4$CO), 162 (100, NC$_6$F$_4$). High-resolution MS calculated for C$_{13}$H$_7$F$_4$N$_5$O$_5$: 389.0382; found: 389.0405.

NHS ester 5 was prepared from acid 12 in a manner similar to ester 4 and was isolated as a colorless solid at 91% yield having a mp=93°–95° C. $^1$H-NMR: 1.77 (m,2), 1.85 (m,2), 2.691 (t,2, J=6.65), 2.841 (s,4) 3.512 (q,2, J=6.24), 6.22 (m,1). IR: 2127, 1817, 1786, 1742, 1681, 1649, 1602, 1526, 1487, 1260, 1209, 1069 cm$^{-1}$. MS: 431 (5, M$^+$). 403 (3, M$^+$—N$_2$), 317 (22, M$^+$—NHS), 289 (8, M$^+$—NHS—N$_2$), 162 (100, NC$_6$F$_4$). High-resolution MS calcd for C$_{16}$H$_{13}$F$_4$N$_5$O$_5$: 431.0850; found: 431.0866.

The two NHS-active esters 4 and 5, together with NHS-active ester 3, formed a group of NHS-containing PFPAs having linkers of different lengths between the PFPA and the NHS groups. Thus, compounds 3, 4, and 5 are useful for functionalizing amino groups in biopolymers such as polypeptide chains via the NHS group and subsequent cross-linking to a proximally located biopolymer by photo-generated nitrene intermediates. The compounds can also be used for functionalizing substrates, including polymeric substrates.

EXAMPLE 9

This Example is similar to Example 8, except that two heterobifunctional and cleavable PFPA-based crosslinkers were synthesized, as shown generally by the formula:

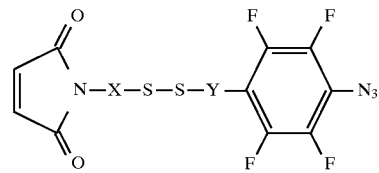

For example, the following compound was synthesized:

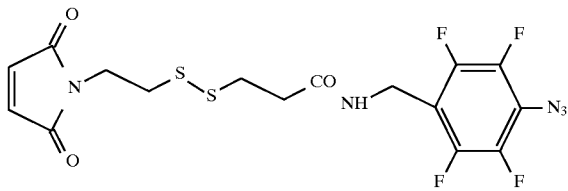

In general, the PFPA portion of the molecule can be used to functionalize a substrate, allowing the maleimide portion to be used for attaching another functional group (via reaction with an SH- containing molecule or a 1,3-diene-containing molecule in a Diels-Alder type reaction.) Then, at a later time, the maleimide side can be cleaved from the surface under mild conditions. Another cleavable group can be a 1,2-diol linkage cleavable using periodic acid.

EXAMPLE 10

This Example concerns the functionalization of polystyrene. A 1-cm² piece of silicon wafer was coated with a solution of 5% w/w polystyrene by spinning at 1000 rpm. The wafer was then spin-coated with a solution of 0.5% w/w of N-hydroxysuccinimidyl-4-azido-2,3,5,6-tetrafluorobenzoate in nitromethane at a speed of 1000 rpm, baked at 60° C. for 20 minutes, and subjected to electron-beam lithography. The coated wafer was dipped in nitromethane for 20 seconds to remove any unattached PFPA, air dried, and allowed to react with a solution of 2 mg/mL 5-(aminoacetamido)fluorescein in ethanol at 25° C. for 1 hour. The wafer was then immersed in ethanol overnight to remove the non-covalently attached fluorescein residues.

Figure 4A:
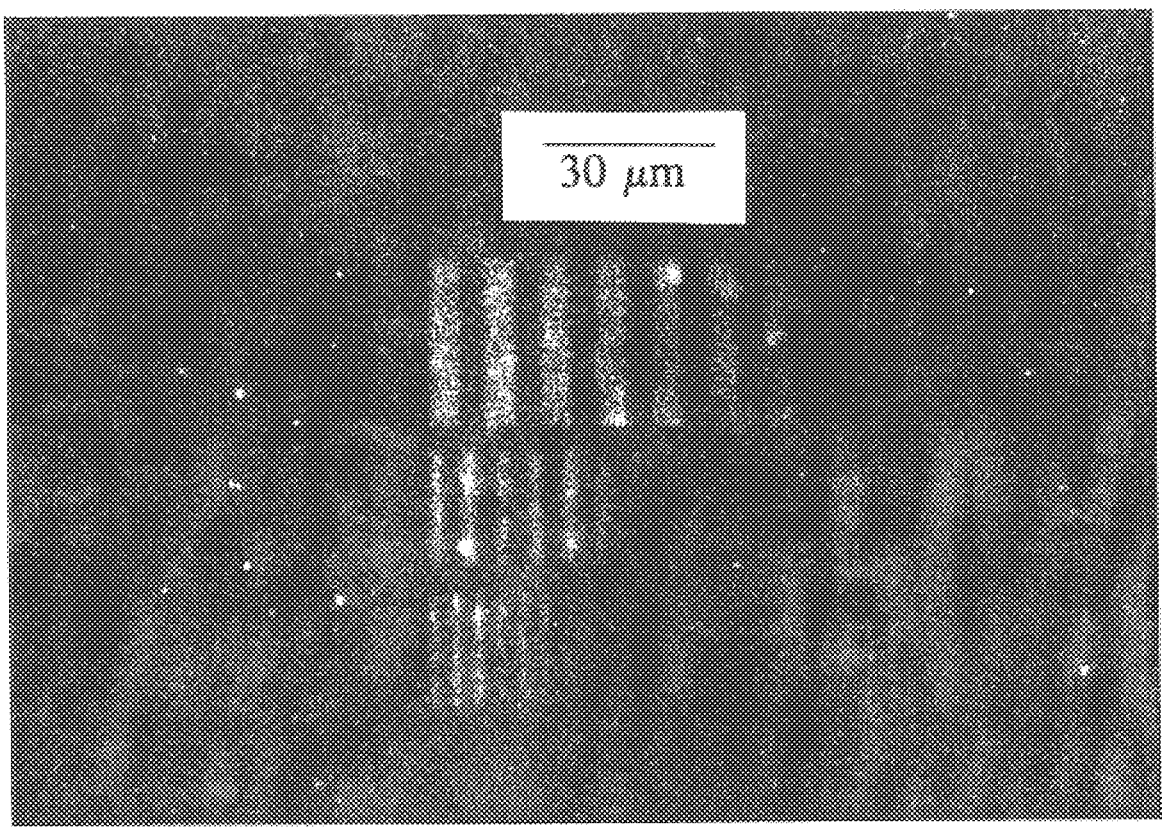
FIG. 4A is a photomicrograph obtained using a fluorescence microscope (450–490 nm excitation wavelength; >510 nm emission wavelength) of a polystyrene surface functionalized with NHS-PFPA using an electron beam as a reaction-energy source, as described in Example 10.
Figure 4B:
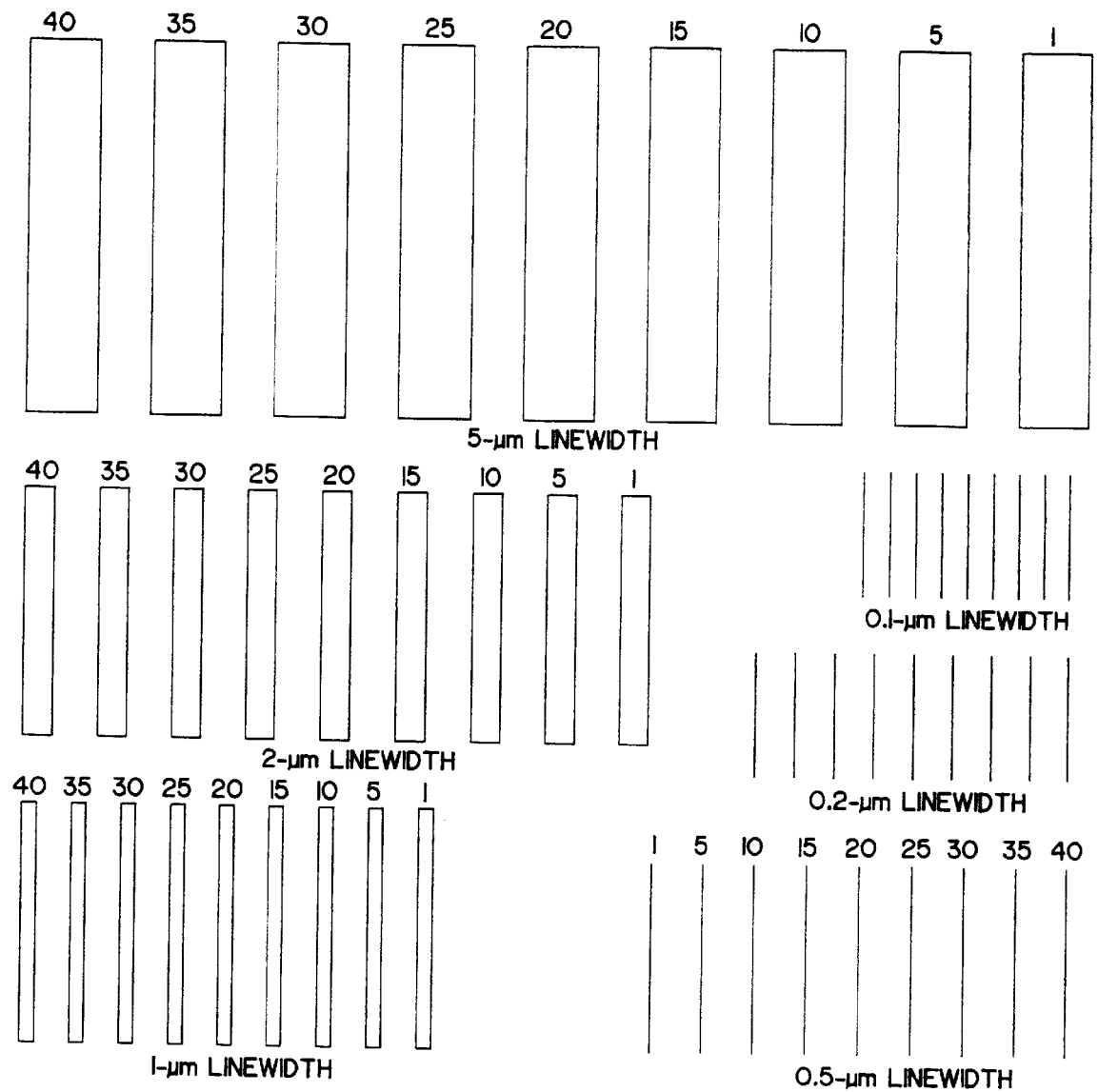
FIG. 4B is a legend for FIG. 4A showing beam dosages and linewidths.

The results are shown in FIG. 4A (legend in FIG. 42), depicting patterns observed under a fluorescence microscope (450–490 nm excitation, >510 nm emission). The patterns were delineated by electron-beam lithography with the line widths of (from thickest to thinnest): 5 μm, 2 μm, 1 μm, 0.5 μm, 0.2 μm, and 0.1 μm (FIG. 4B). As shown in FIG. 4B, the dosages are 40, 35, 30, 25, 20, 15, 10, 5, and 1 μC/cm² from left to right for the 5, 2, and 1 μm widths and from right to left for the 0.5, 0.2, and 0.1 μm widths.

In FIG. 4A, features of 0.2 μm were resolved. The smallest features (0.1 μm) were not resolved in this unoptimized experiment. The sensitivity is about 10 to about 30 μC/cm².

EXAMPLE 11

In this Example, we functionalized the hydrocarbon polymer polystyrene (PS) by —CH insertion of photochemically generated nitrene intermediates.

Referring to Scheme 14, the active-ester azide 1 was formed by esterification of N-hydroxysuccinimide (NHS) with 4-azido-2,3,5,6-tetrafluorobenzoic acid. The active-ester azide 1 was selected for study as a representative functionalizing agent because NHS esters react readily with amine-containing reagents to form amides (R1—NH—COR).

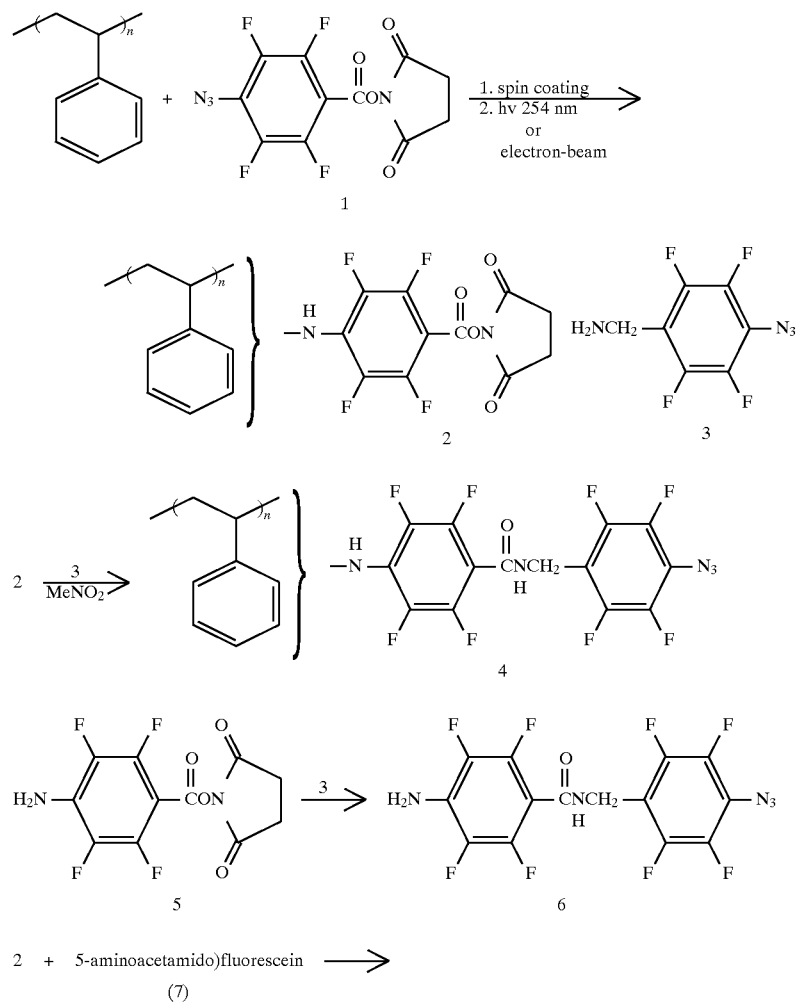

-continued
Scheme 14

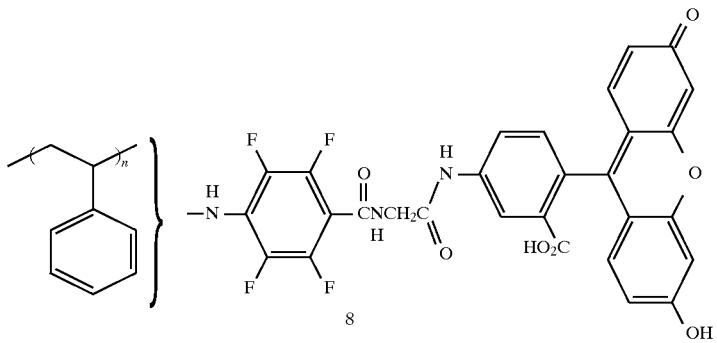

A solution containing 50.2 mg PS (mean molecular weight 125,000 to 250,000 daltons) and 4.0 mg NHS ester 1 in 1.0 mL xylene was prepared, yielding an 8% w/w solution of 1. The solution was spin-coated on a NaCl disc using a photoresist spinner (Headway Research, Inc., Garland, Tex.) set at 1000 rpm. After drying the disc at 50° C. for one hour, the film remaining on the disc had a thickness of about 0.7 μm, as measured using an ellipsometer (Rudolph Research, Inc., Flanders, N.J.). The film was photolyzed for 1.5 minutes using a Rayonet photoreactor (Southern New England Ultraviolet Co., Branford, Conn.) employing 254-nm lamps as photon sources.

Figure 5:
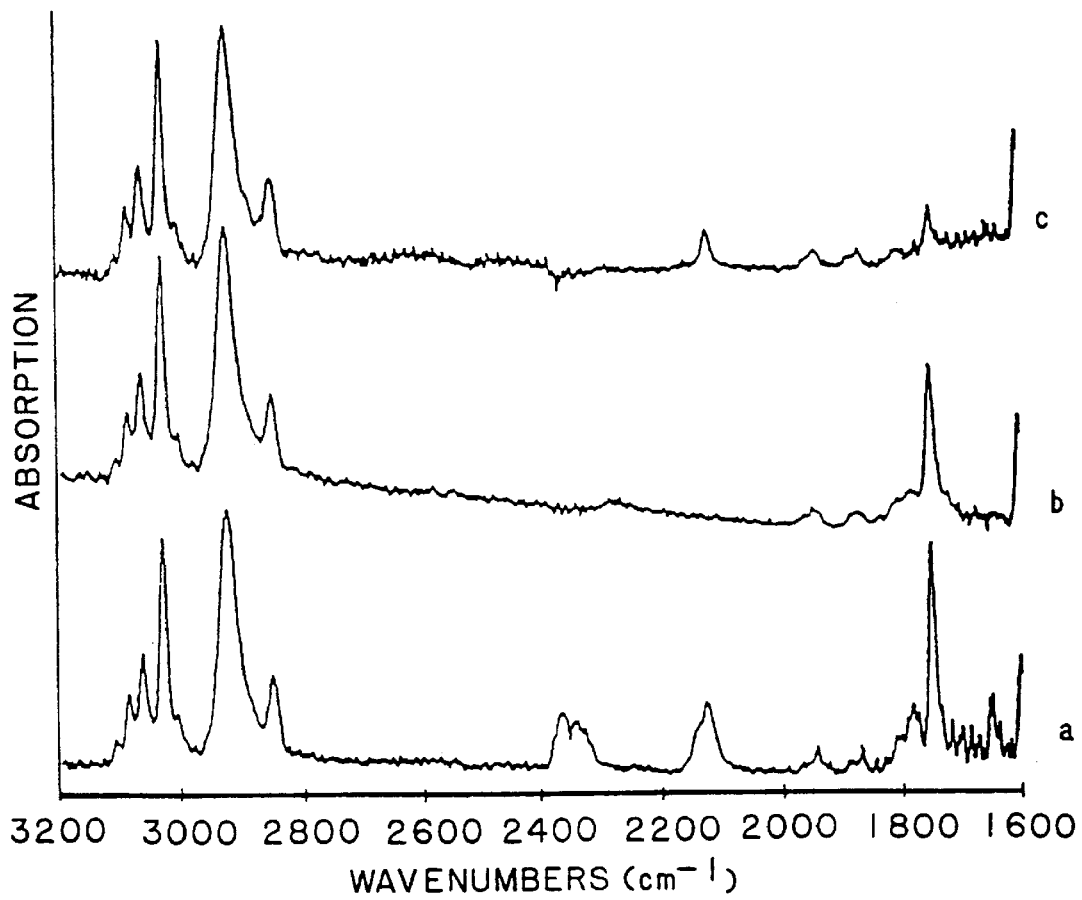
FIG. 5 shows IR spectra of polystyrene including 8 wt-% NHS-PFPA (compound 1 in Scheme 11), wherein plot "a" was obtained before photolysis; plot "b" was obtained after photolysis; plot "c" was obtained after treatment with the amine 3 (Scheme 11); and the peaks at 2300 $cm^{-1}$ are from $CO_2$.
Figure 6:
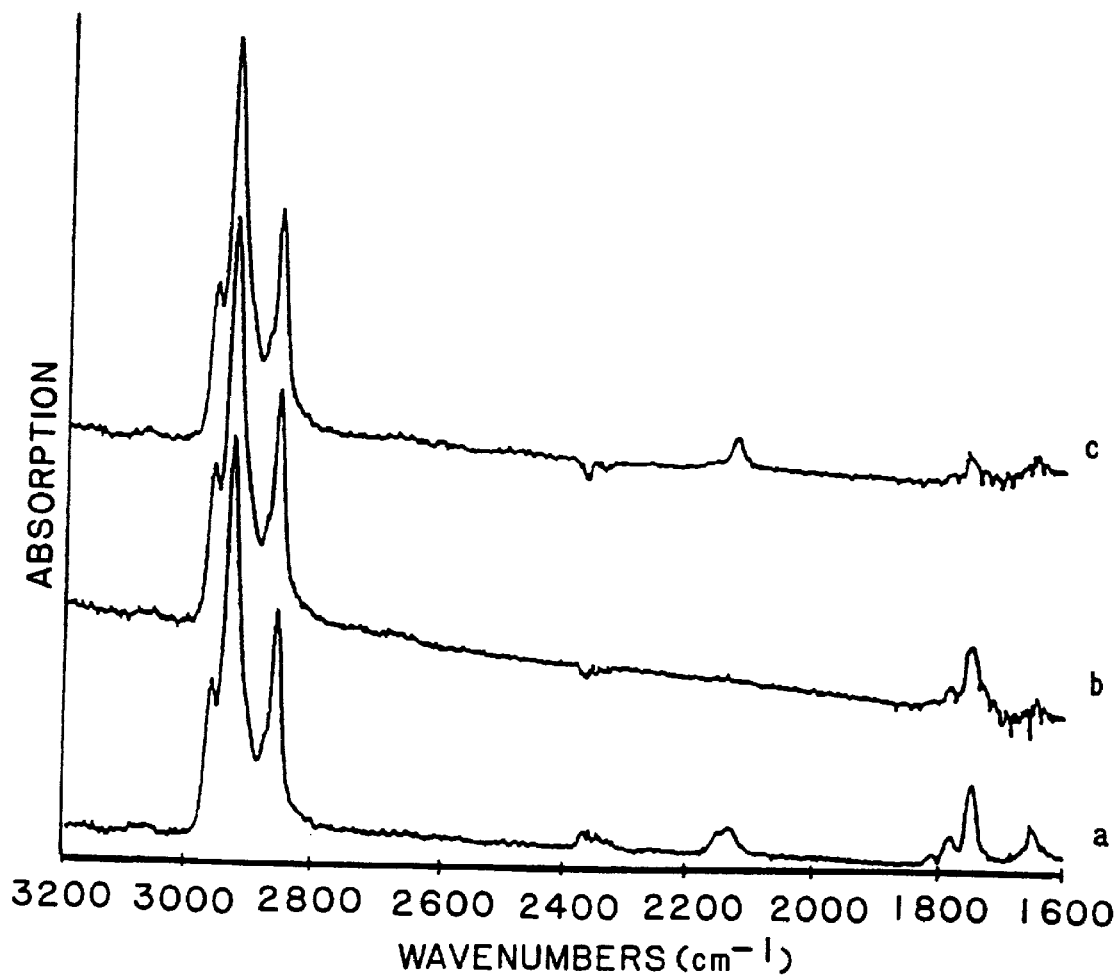
FIG. 6 shows IR spectra of poly(3-octylthiophene) including 10 wt-% NHS-PFPA (compound 1 in Scheme 11), wherein plot "a" was obtained before photolysis; plot "b" was obtained after photolysis; and plot "c" (shown offset from plot "b") was obtained after treatment with the amine 3 (Scheme 11).

The photolysis resulted in the smooth decomposition of the azide group with concomitant formation of the functionalized PS 2 derived from a CH-insertion reaction. The photolysis was monitored by the disappearance of the azide absorption at 2124 cm$^{-1}$, as indicated in FIG. 5 by comparing curves "a" (before photolysis) and "b" (after photolysis). The active ester carbonyl absorption around 1750 cm$^{-1}$ was not affected by the photolysis reaction.

Next, the functionalized PS film 2 was further functionalized by immersion at room temperature for over two hours in a solution of 5.4 mg 4-azido-2,3,5,6-tetrafluorobenzylamine (3) (i.e., the hydrochloride salt of 3) and 10 mg Et$_3$N in nitromethane. (Nitromethane is a solvent that does not dissolve PS.) The film was then removed from the solution and immersed in 40 mL nitromethane for 10 minutes, rinsed using nitromethane, then air dried. The coupling reaction that occurred during said immersion of the functionalized PS film 2 in the solution of 3 was monitored by IR spectroscopy using a Nicolet Model 5DXB FTIR spectrometer (Madison, Wis.).

As the coupling reaction proceeded, an azide-absorption peak at 2121 cm$^{-1}$ reappeared because, as the amine 3 attached to the functionalized PS 2, the azide group of 3 remained attached and unreacted. A corresponding decrease in absorption at 1750 cm$^{-1}$ was attributed to loss of the carbonyl groups (>C=O) of the active ester, as also seen in FIG. 1 by comparing curve "c" with curve "b". The IR spectra confirmed that amine 3 reacted with the NHS active esters of the film 2, resulting in the further modification of the PS by incorporation of the perfluorophenylazide groups along the PS polymer chain to yield a functionalized PS polymer 4.

IR intensity comparison of the azide absorptions (comparison of curve "c" with curve "a" of FIG. 1) indicated that about 40 percent of the original number of azide groups became incorporated into the PS chain of polymer 4 as a result of treatment of 2 with 3. This was probably due to the fact that photolysis of azide 1 in the presence of PS resulted in less than a 100-percent yield of CH insertion. It is also possible that some of the NHS groups may have been cleaved by adventitious hydrolysis during the treatment with the solution of amine 3 in nitromethane.

EXAMPLES 12 AND 13

These Examples comprise control experiments for Example 11. Compounds are as shown in Scheme 14.

In Example 12, a solution of PS was prepared as in Example 11 but without NHS active ester 1. The PS solution was formed into a film and photolyzed as in Example 11, then treated with a solution of the amine 3 in nitromethane. Afterward, no azide absorption was observed in the IR spectrum of the film.

In Example 13, a film of PS containing active ester 1 was prepared as in Example 11. The Example-13 film was not photolyzed but rather treated directly with a solution of the amine 3 in nitromethane. IR spectrophotometry revealed the disappearance of absorptions at 2124 and 1750 cm$^{-1}$, showing that the nitromethane had extracted essentially all of the active ester 1 or the corresponding amide out of the polymer.

Examples 12 and 13 showed that both the NHS active ester 1 and photolysis are needed for the modification of the PS film with NHS active ester groups.

EXAMPLE 14

In this Example, referring further to Scheme 14, N-succinimidyl 4-amino-tetrafluorobenzoate (5) was used as a model for the polymer 2. To prepare 5, a mixture of 214 mg (1.00 mmol) 4-amino-tetrafluorobenzoic acid, 119 mg (1.00 mmol) N-hydroxysuccinimide and 211 mg (1.00 mmol) dicyclohexylcarbodiimide in 10 mL CH$_2$Cl$_2$ was stirred for 24 hours. The mixture was filtered and the solid was dried. The solid was then stirred with 6 mL acetone and the mixture was filtered. The filtrate was evaporated to leave 262 mg (83 percent yield) of 5 as a white solid having a melting point of 200°–201° C. $^1$HNMR: δ 62.899 (s, 4), 4.665 (s, 2). IR: 3522, 3418, 1779, 1749, 1683, 1530, 1507, 1317 cm$^{-1}$. MS: 306 (M$^+$, 2), 192 (100), 164 (30).

A mixture of 11 mg (0.036 mmol) of the active ester 5 and 6.9 mg (0.031 mmol) of amine 3 in CDCl$_3$ was prepared and allowed to react (not all the yield of 5, prepared above, dissolved in CDCl$_3$). Progress of the reaction was monitored by $^1$H NMR spectroscopy at room temperature. As the reaction progressed, new signals at δ4.7 (d) were observed. After 24 hours, a clear solution was obtained. When the reaction mixture was assayed by $^1$H NMR spectrometry, no greater amount of signal was seen at δ3.941 for 3 and δ2.899 for 5. The mixture was separated by preparative thin-layer chromatography (hexane-THF 1:1) to give 12 mg (94 percent yield) of the amide 6 as a white solid having a melting point of 155°156° C. (actually a decomposition temperature). $^1$H NMR: δ4.286 (s, 2), 4.701 (d, 2), 6.402 (m, 1). IR: 3411, 2122, 1686, 1668, 1497, 1314, 1239 cm$^{-1}$. MS: 411 (M$^+$, 1), 383 (20), 192 (100), 164 (18). The IR spectrum of the amide 6 showed an azide absorption peak at 2124 cm$^{-1}$, which was also observed in the polymer film of Example 11 after photolysis and reaction with amine 3.

EXAMPLE 15

In this Example, shown generally in Scheme 15, we investigated the functionalization of the conductive polymer poly(3-octylthiophene) (abbreviated P3OT). P3OT can be photochemically cross-linked by bis-PFPA and can be used for the direct production of conductive structures via cross-linking under electron-beam lithographic conditions. Cai et al., *J. Mol. Electron.* 7:63 (1991).

For this Example, the P3OT was prepared from 3-octylthiophene as reported in Cai et al., id.

Referring to Scheme 15, a solution of 25.8 mg P3OT and 2.6 mg (10% w/w) of the NHS ester 1 in 0.8 mL xylene was spin-coated on a NaCl disc, dried, photolyzed, and developed as described in Example 1. The photolysis reaction yielded a functionalized polymeric film 9. The film 9 was treated with the amino azide 3 (structure shown in Scheme 11) in nitromethane under conditions as described in Example 1 for treating PS. A functionalized polymeric film 10 formed which involved an amide-formation reaction between 3 and the NHS active esters with concomitant covalent attachment of a new set of azide groups to the P3OT polymer. (In FIG. 2, compare curve "b" with curve "c".) The IR spectrum of the film 10 showed a moderately strong absorption at 2121 cm$^{-1}$ for the azide group (FIG. 2).

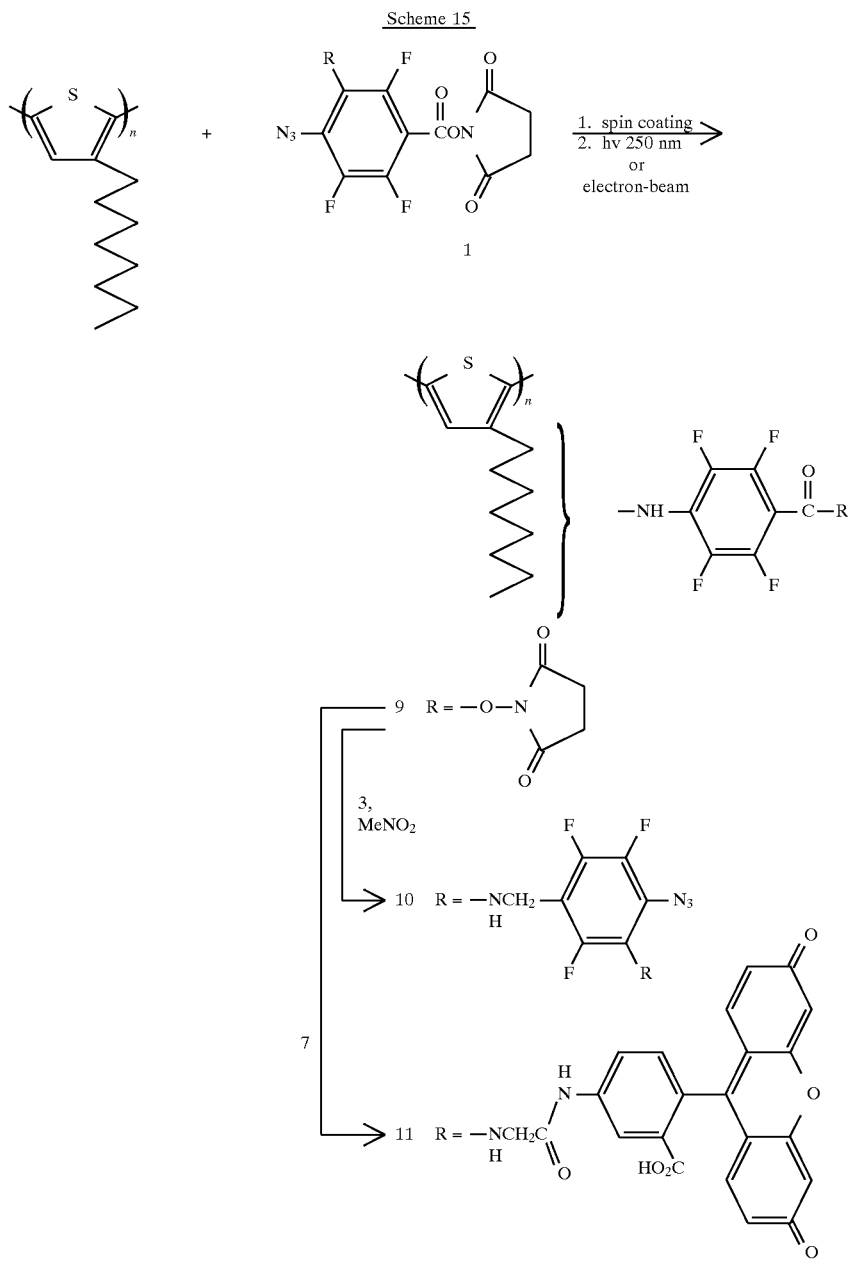

It is believed that the C—H insertion reaction yielding the functionalized polymer 9 occurred along the octyl side chains without involvement of the thiophene ring. This is based upon the observation that photolysis of the simple PFPA ester methyl 4-azidotetrafluorobenzoate in cyclohexane/thiophene yielded methyl (N-cyclohexyl-4-amino)-tetrafluorobenzoate as the only CH-insertion product that could be isolated.

EXAMPLE 16

This Example is a control experiment for Example 15.

A solution of 23.2 mg P3OT in 0.8 mL xylene (in the absence of 1) was treated with the amine 3 as described in Example 15. No azide absorption was observed in the IR spectrum of the resulting film, indicating that no incorporation of the amine 3 occurred.

Therefore, a first functionalization of P3OT with a compound such as 1 is necessary in order to perform a second functionalization with the amine 3.

EXAMPLE 17

In this Example, we investigate the use of electron-beam lithography to accomplish both cross-linking of a polymer (i.e., PS) and the introduction of NHS active ester groups in the polymer in a single step. General reactions are illustrated in Scheme 14.

A solution of 50.2 mg of PS and 4.0 mg of NHS ester 1 (8% w/w) in 1.0 mL xylene was spin-coated on a silicon wafer as described generally in Example 11. The film was dried for 35 minutes at 90° C. and exposed to an electron beam using a scanning electron microscope (SEM) (manufactured by JOEL-SEM, Peabody, Md.), modified for electron-beam lithography. Nabity et al., *Rev. Sci. Instrum.* 60:27 (1989). The electron beam was used to "draw" micron-sized patterns (in the form of eight five-line patterns and a pattern of five circles of different diameters) on the film. The exposed film was "developed" by dipping in xylene for 35 seconds, rinsing in isopropyl alcohol for 10 seconds, then drying with a stream of nitrogen, thereby yielding a "developed" film 2. The film 2 was photographed using an optical microscope, yielding results shown in FIG. 3A.

In FIG. 3A, the widths of the lines in each five-line set were 0.1, 0.2, 0.5, 1.0, and 2.0 $\mu$m. Each successive five-line set was obtained with an increased electron-beam intensity relative to the preceding set. In the top row of sets, the electron-beam intensities were 50, 60, 70, and 80 $\mu$C/cm$^2$. In the bottom row of sets, the electron-beam intensities were 90, 100, 110, and 120 $\mu$C/cm$^2$. The line width of each of the circles was the same: 0.5 $\mu$m. The electron-beam intensity used to "draw" the circles was 60 $\mu$C/cm$^2$. The lines and circles shown in FIG. 3A are composed of functionalized polystyrene 2 (i.e., polystyrene molecules having active esters covalently bonded thereto).

Figure 7A:
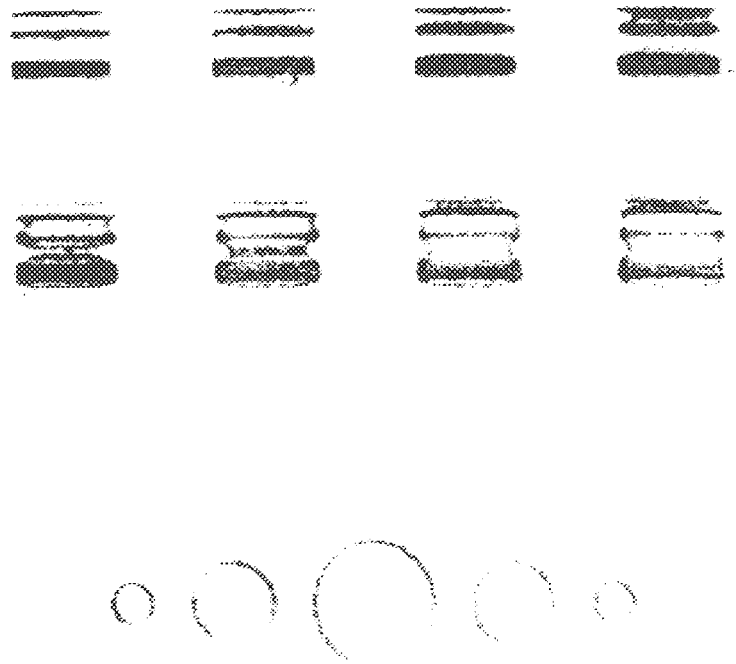
FIG. 7A is a photomicrograph obtained using an optical microscope, depicting linear and circular functionalized patterns produced on a film of polystyrene and 8 wt-% NHS-PFPA by electron-beam lithography.

Referring now to Scheme 14, the film 2 (after obtaining the photographs shown in FIG. 7A was immersed in a solution of 2.5 mg of amino-fluorescein (compound 7) and 8.3 mg of Et$_3$N in 1.5 mL of EtOH for 4 hours so as to introduce an easily visible fluorescent marker at the active-ester sites on the film. Afterward, the film was washed with EtOH, immersed in EtOH for 2 hours, rinsed with EtOH, then air-dried to yield the film 8. The film 8 was observed under a fluorescence microscope (Carl Zeiss, Germany) equipped with epifluorescence optics. The microscope was fitted with a fluorescein filter set (excitation wavelength 450–490 nm, emission wavelength 515–565 nm). The fluorescence patterns shown in FIG. 7B were observed.

Since the fluorescent patterns exhibited by film 8 (FIG. 3B) were coincidental to the patterns observed of the functionalized polystyrene 2 shown in FIG. 3A, we concluded that coupling of the fluorescence marker in film 8 occurred only at sites (film 2) on the polymer to which active esters had been previously coupled.

Figure 7B:
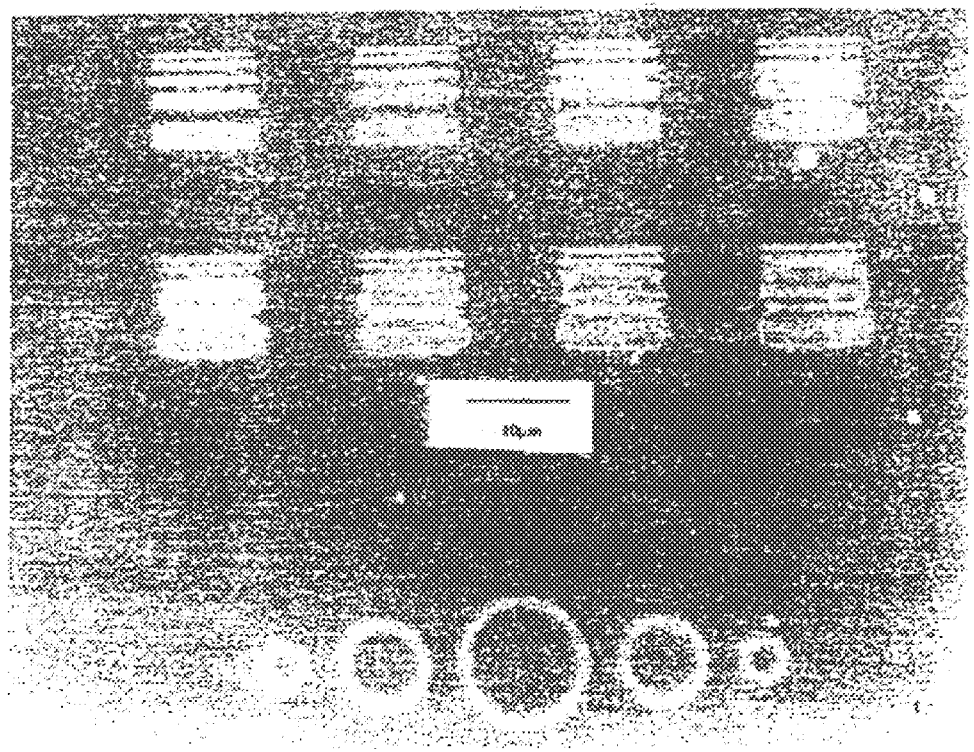
FIG. 7B is a photomicrograph obtained using a fluorescence microscope fitted with a fluorescein filter set, depicting the functionalized patterns of FIG. 3A after treatment with amino-fluorescein.

In FIG. 7B functionalization of PS had occurred at a dosage of about 50 $\mu$C/cm$^2$ in the film. We also found that crosslinking of PS alone required about 90 $\mu$C/cm$^2$.

EXAMPLE 18

This Example is an experimental control for Example 17. Compounds are as shown in Scheme 14.

A PS film was prepared without the NHS ester 1 but otherwise treated as described in Example 17. The film was exposed to an electron beam and developed as described in Example 17 and photographed using an optical microscope. The PS film was then treated with amino-fluorescein 7 and observed under a fluorescence microscope. No fluorescence pattern was observed. Therefore, prior attachment of the NHS active ester 1 to the PS molecules was required for the subsequent attachment of the amino-fluorescein label 7 to the polymer.

EXAMPLE 19

This Example is similar to Example 13 except that, in this Example, we "drew" micron-sized patterns on a P3OT film containing NHS active ester using an electron beam. The general reactions are shown in Scheme 15.

A solution of 25.7 mg of P3OT and 1.8 mg of NHS ester 1 (7% w/w) in 0.6 mL of xylene was spin-coated on a silicon disc and dried at 60° C. for 30 minutes. The resulting film was exposed to an electron beam as described in Example 13 so as to "draw" micron-sized patterns on the film (line width 0.5 $\mu$m; beam intensity 20 $\mu$C/cm$^2$). The film was then "developed" by dipping in xylene for 10 seconds, rinsing in isopropyl alcohol for 10 seconds and drying under a stream of nitrogen gas to yield the film 9. The film was then immersed in a solution of 1.5 mg of amino-fluorescein 7 and 6 mg of Et$_3$N in 1 mL of EtOH for 4 hours. The film was then washed with EtOH, immersed in EtOH for 1 hour, washed again with EtOH, then air-dried to produce the sample film 11.

Figure 8A:
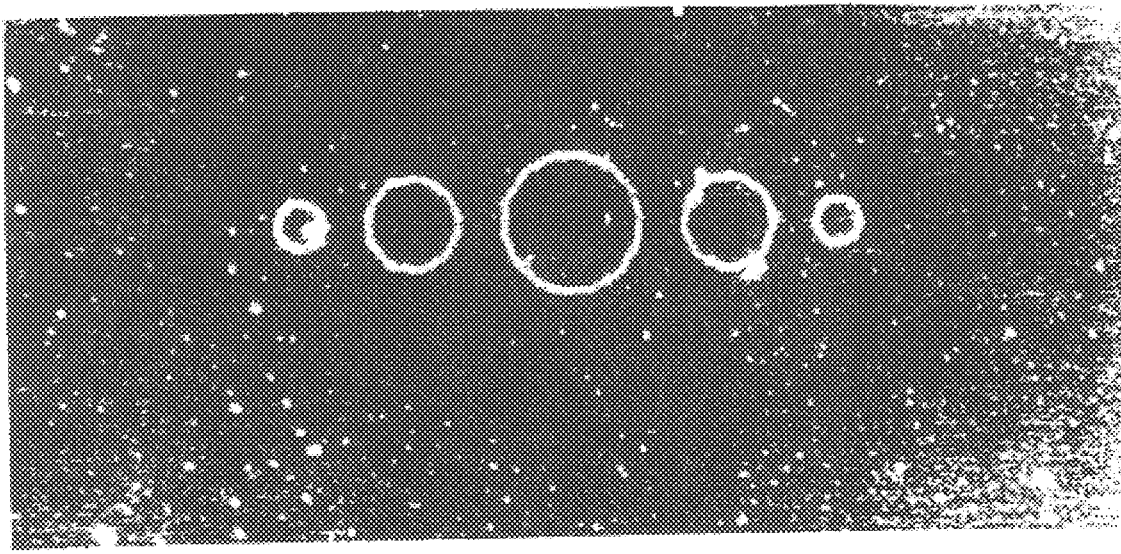
FIG. 8A is a photomicrograph obtained using a fluorescence microscope of circular patterns produced on a film of poly(3-octylthiophene) and 7 wt-% of NHS-PFPA by exposing the film to electron-beam lithography conditions and subsequently treating the film with amino-fluorescein, wherein the microscope was fitted with a rhodamine filter set.
Figure 8B:
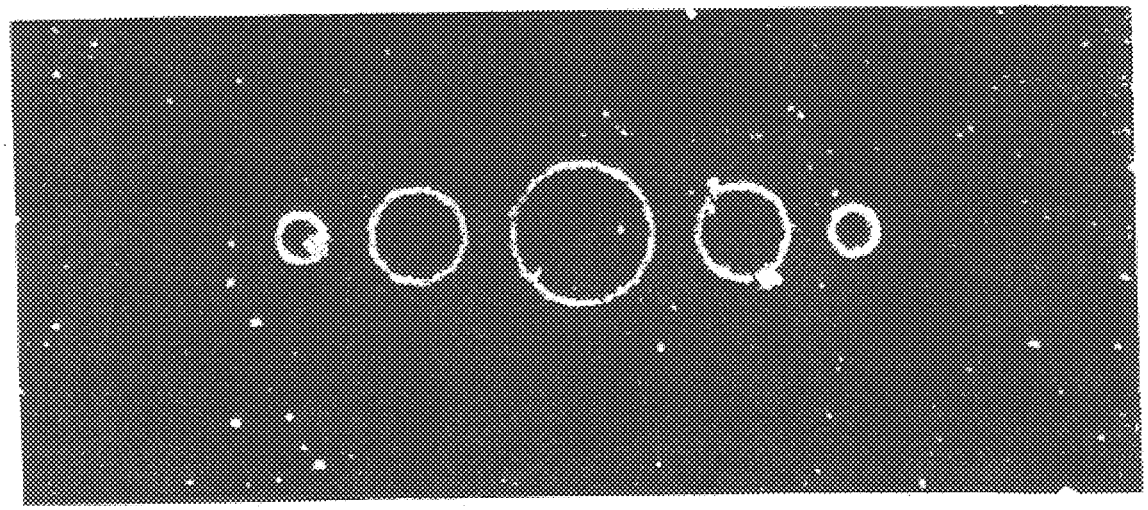
FIG. 8B is a photomicrograph obtained using a fluorescence microscope of circular patterns produced on a film of poly(3-octylthiophene) and 7 wt-% of NHS-PFPA by exposing the film to electron-beam lithography conditions and subsequently treating the film with amino-fluorescein, wherein the microscope was fitted with a fluorescein filter set.

The sample film 11 was observed and photographed using a fluorescence microscope equipped with a rhodamine filter set (excitation wavelength 510–560 nm, emission wavelength >590 nm), yielding the results shown in FIG. 8A. The same sample film was observed and photographed using the fluorescence microscope equipped with a fluorescein filter set (excitation wavelength 450–490 nm, emission wavelength 515–565 nm) yielding the results shown in FIG. 8B. As can be seen, substantially identical patterns were observed having strong fluorescence at both the rhodamine excitation wavelength (FIG. 8A) and the fluorescein excitation wavelength (FIG. 8B).

P3OT alone is strongly fluorescent at the rhodamine excitation wavelength but only weakly fluorescent at the fluorescein excitation wavelength. (This is why the films in this Example were observed using a rhodamine filter set and a fluorescein filter set; strong fluorescence observed at the fluorescein excitation wavelength would necessarily be due to the presence of other molecules than just P3OT.) In FIGS. 4A and 4B, the observed strong fluorescence at both the rhodamine and fluorescein excitation wavelengths indicates that fluorescein became attached to the regions exposed to the electron beam (FIGS. 8A and 8B).

EXAMPLE 20

This Example is a control for Example 19.

Figure 8C:
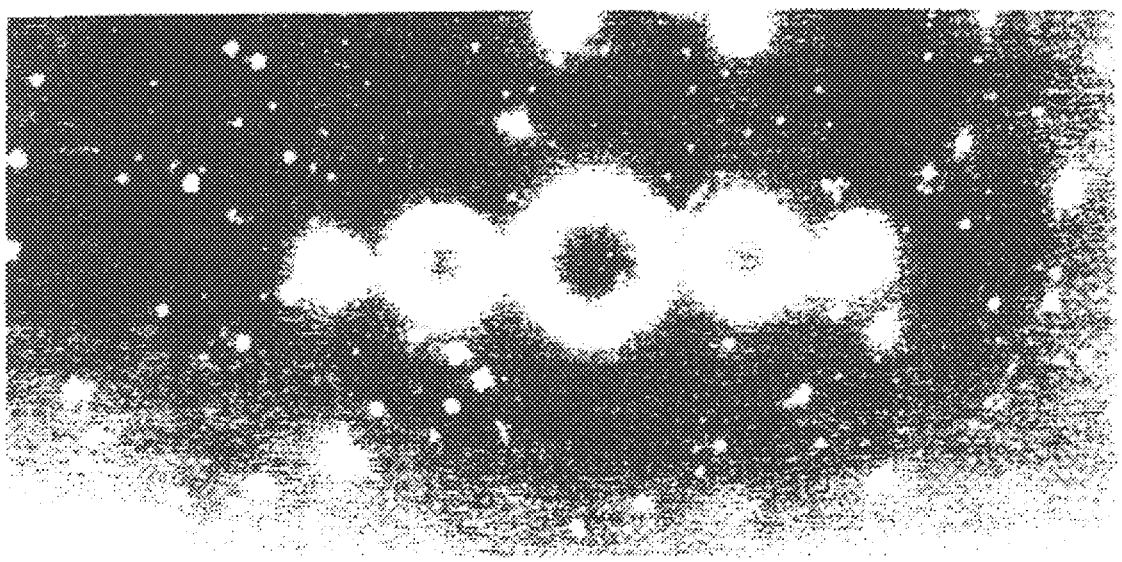
FIG. 8C is a photomicrograph obtained using a fluorescence microscope of circular patterns produced on a film of poly(3-octylthiophene) by exposing the film to electron-beam lithography conditions and subsequently treating the film with amino-fluorescein, wherein the microscope was fitted with a rhodamine filter set.
Figure 8D:
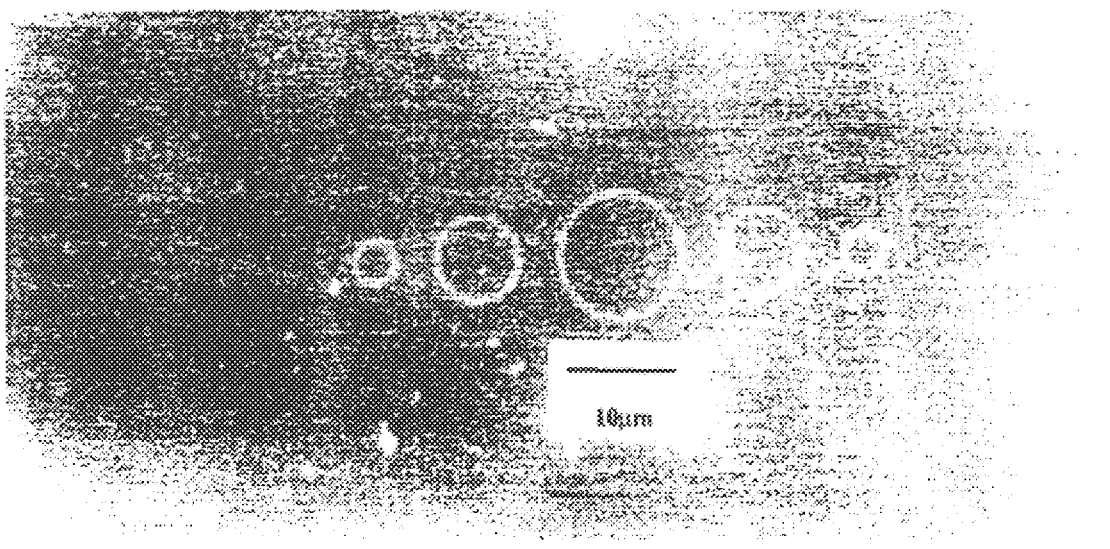
FIG. 8D is a photomicrograph obtained using a fluorescence microscope of circular patterns produced on a film of poly(3-octylthiophene) by exposing the film to electron-beam lithography conditions and subsequently treating the film with amino-fluorescein, wherein the microscope was fitted with a fluorescein filter set.

A P3OT film (without the active ester 1) was exposed to an electron beam (intensity 30 $\mu$C/cm$^2$, line width 0.5 $\mu$m), developed, then treated with aminofluorescein 7 as described in Example 19. The micron-sized patterns "drawn" on the control P3OT film were identical to the patterns in Example 19. When the control film was examined using a fluorescence microscope, strong fluorescence was observed at the rhodamine excitation wavelength (FIG. 8C), but only weak fluorescence was observed at the fluorescein excitation wavelength (FIG. 8D).

The results indicate that substantially no fluorescein 7 became attached to P3OT in the absence of activated ester groups. Therefore, the presence of NHS active ester is required in order to obtain any substantial covalent coupling of the fluorescein 7 to P3OT.

EXAMPLE 21

In this Example, we functionalized poly(3-octylthiophene) (P3OT) as shown in Scheme 16.

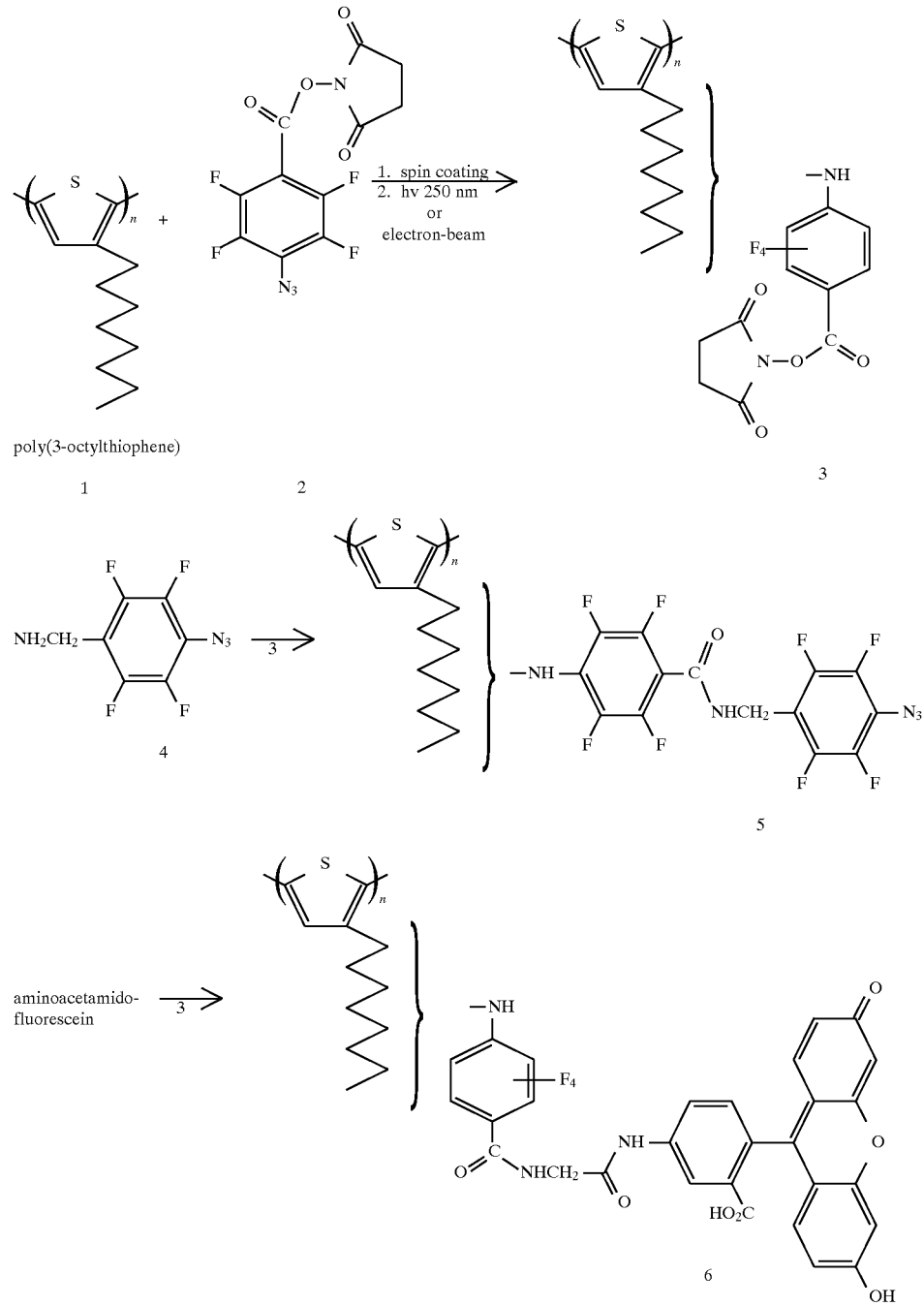

In this scheme, a solution of NHS-PFPA (2) and P3OT (1) was spin-coated onto the surface of a silicon substrate in a manner as generally discussed above, then exposed to a reaction-energy source such as 254-nm photons or an electron beam to yield the functionalized P3OT (3). Subsequent reaction of the functionalized P3OT 3 with the PFPA compound 4 produced 5. Reaction of 5 with aminoacetamidofluorescein yielded fluoroescein-labeled P3OT (6).

Additional methods for attaching materials to substrates are illustrated below in Schemes 17–19. One embodiment involves using silanes as molecular tethers for attaching functionalizing reagents or coating materials, such as biocompatible polymers, to substrates. In general, the method comprises coupling a silane reagent, such as an alkoxy silane [Si(OR')$_3$R], a halosilane [Si(X)$_3$R, wherein X is halogen] or an alkoxyhalosilane [Si(OR')$_2$XR], to a substrate capable of reacting with the silane reagent. The method is particularly, but not exclusively, useful with substrates comprising Si or SiO$_2$, such as silicon wafers, glass and quartz. The silane reagent provides a tether with which additional compounds can be reacted to attach such additional compounds to a substrate.

The silane reagent generally satisfies the following formula:

$$Si(OR')_nX_{3-n}R$$

wherein n is 0–3, R is an aromatic compound, such as toluoyl, or an alkyl, an alkenyl or an alkynyl chain having from about 1 to 25 carbon atoms, R$^1$ is an alkyl group having from about 1 to 10, generally 1–5 carbon atoms, and X is a halogen, such as chlorine. If R provides a terminal C—H bond, such as might be provided by a methyl or toluoyl group, then the silane reagent generally is subsequently reacted with a nitrene.

Alternatively, R can provide a terminal nucleophophilic group, such as an amino- or hydroxyl-bearing aromatic compound, an alkyl amine, an alcohol or a thiol, or a terminal electrophilic group such as an activated ester. Scheme 17 illustrates the formation of a substrate coated with a silane reagent having a terminal amine, which generally reacts as a nucleophilic group.

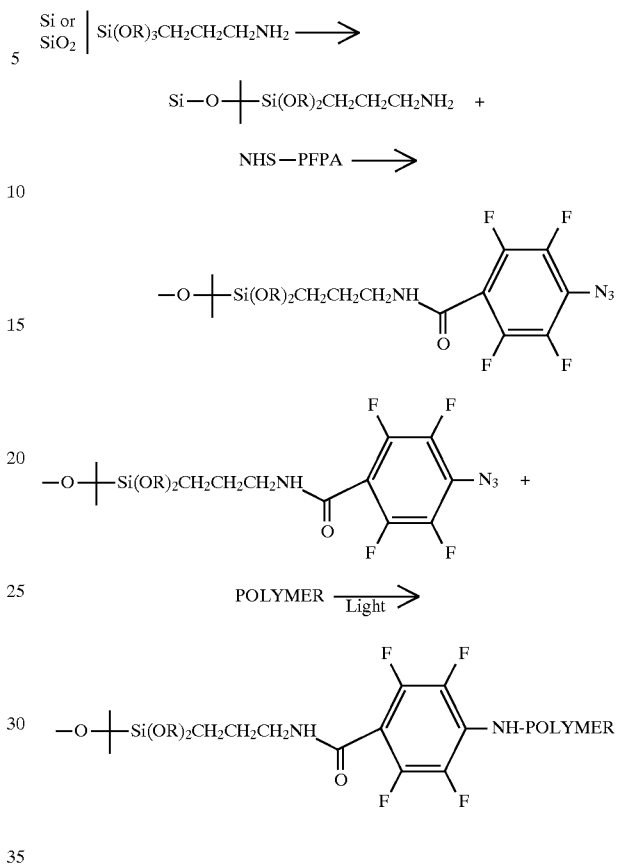

The selection of R in the silane reagent is best decided by considering the functional group or coating material to be used. If the material includes chemical moieties capable of insertion and/or addition reactions with nitrenes, then the R group of the silane reagent should provide a functional group to couple a perhalophenyl azide to the substrate. This positions the azide as the terminal functional group for reaction with the material that includes moieties capable of addition reactions with nitrenes. See Scheme 18.

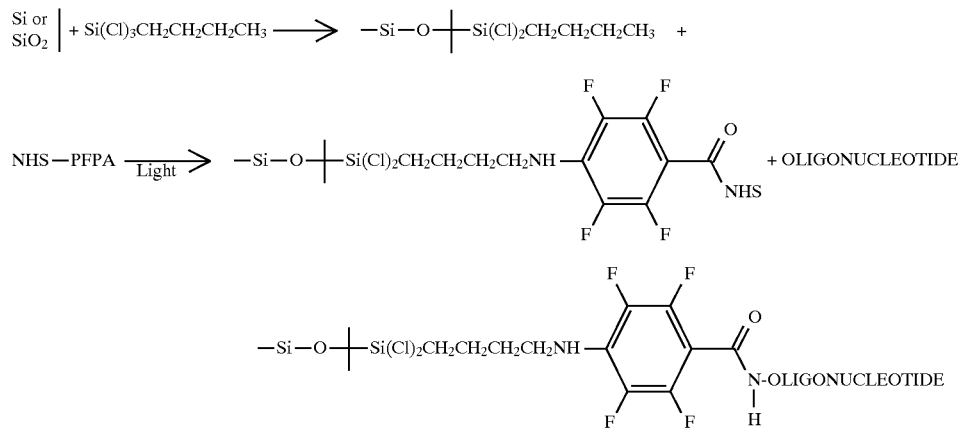

Alternatively, if the functional reagent or coating material has nucleophilic functional groups, such as amines or hydroxyl groups, these functional groups can be used to couple to a PHPA, particularly a PHPA that includes an activated ester, such as NHS-PFPA. As used herein, the phrase "activated ester" refers to esters to which are coupled leaving groups or groups which enhance the reactivity of the ester to nucleophilic attack. One example of an activated ester is NHS-PFPA. This approach is illustrated in Scheme 19.

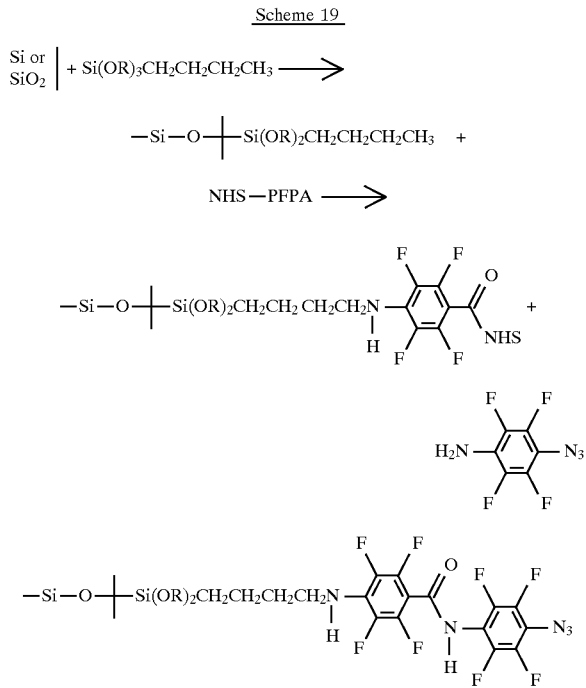

The following examples concern particular processes for coating or functionalizing materials. These examples are illustrative of the scope of the invention only, and should not be construed to limit the invention to the particular aspects described.

Examples 22–23 concern the formation of crosslinked films on substrates. Coating substrates with a crosslinked film generally comprises reacting a polymeric material having functional groups capable of undergoing insertion and/or addition reactions with nitrenes with a reagent that includes at least two nitrenogenic groups. In the presence of the polymeric material, the plural nitrenogenic groups of the reagent react to crosslink the film, thereby providing a crosslinked film mechanically disposed upon the substrate surface.

EXAMPLE 22

A solution was formed comprising 10 milligrams of polypropylene (chromatographic grade from PolySciences, Inc.) and 1 milligram of bis-PFPA in about 1 milliliter of toluene. The solution was heated to a temperature of about 100° C., and then spincoated onto a silicon wafer. The wafer was then photolyzed at 254 nm for about 5 minutes to crosslink the polypropylene.

A solution comprising about 5 percent polystyrene in xylene and about 5 weight percent bis-PFPA based on polystyrene also was spincoated onto a silicon wafer to form a film-coated silicon wafer. The film-coated silicon wafer was then photolyzed at 254 nm for about 6 minutes to crosslink the polystyrene.

The films on the wafers were not covalently attached thereto. The wafers were immersed in 100 mM Tris buffer at a pH of about 7.6 for twenty four hours to determine whether the films would be retained on the surface of the wafers during operation. The crosslinked polystyrene and polypropylene films remained on the surface of the silicon wafer even after treatment with the Tris buffer.

EXAMPLE 23

A solution was formed comprising 10 milligrams of polypropylene (chromatographic grade from PolySciences, Inc.) and 1 milligram of bis-PFPA in about 1.0 milliliter of toluene. The solution was heated to a temperature of about 100° C. The hot solution was then spincoated onto a small piece of aluminum to form a film-coated aluminum substrate. The film-coated aluminum substrate was then photolyzed at 254 nm for about 6 minutes. This produced an aluminum substrate having a film coating comprising crosslinked polypropylene.

The aluminum substrates were then immersed in 100 mM Tris buffer at a pH of about 7.6 for twenty four hours. The crosslinked polypropylene film remained on the surface of the aluminum substrate even after treatment with the Tris buffer.

Examples 24–27 concern nucleophilic silane reagents that are reacted in a first step with a substrate capable of reacting with silane reagents, particularly silica or silicon substrates. This first step provides a substrate having a silane tether coupled thereto, wherein the silane tether includes a terminal nucleophilic group that can be reacted in a subsequent step, as illustrated above in Scheme 17.

EXAMPLE 24

Several silica wafers were cleaned with concentrated $H_2SO_4$, followed by water and acetone, and then dried. A solution was formed comprising 2 milliliters of 3-aminopropyltrimethoxysilane (Aldrich) in about 20 milliliters of toluene. The pieces of silica were added to the solution and the resulting composition was then refluxed overnight. The silica wafers were then washed thoroughly with toluene and air-dried to obtain silica wafers modified with 3-aminopropylalkoxy silanes.

Four pieces of the modified silica wafers were then immersed for three hours in a room-temperature solution comprising about 2 milligrams of NHS-PFPA in 2 milliliters of dichloromethane. The amino group of the aminopropylalkoxy silane reacted with the NHS-PFPA to attach the PFPA to the silica wafer. The silica wafers were then rinsed thoroughly with dichloromethane and air dried.

A solution was then formed comprising about 20 milligrams of polypropylene in about 2 milliliters of toluene. The solution was heated to reflux and then spincoated onto two of the treated silica pieces while the solution was still hot. The films were baked at 60° C. for 20 minutes and then photolyzed at 254 nm for about 6 minutes. The photolysis resulted in the formation of an azide, which undergoes an insertion reaction with the polypropylene to attach the polypropylene to the silica substrates.

EXAMPLE 25

Several pieces of glass were cleaned with concentrated $H_2SO_4$, water and acetone and then dried. A solution was then formed comprising 2 milliliters of 3-aminopropyltrimethoxysilane (Aldrich) in about 20 milliliters of toluene. The glass pieces were added to the solution and the resulting composition was then refluxed overnight. The glass pieces were then washed thoroughly with toluene and air-dried to obtain glass substrates modified with 3-aminopropylalkoxy silanes.

The glass substrates were then immersed for three hours in a room-temperature solution comprising about 2 milligrams of NHS-PFPA in 2 milliliters of dichloromethane. The amino group of the aminopropylalkoxy silane reacted with the NHS-PFPA to attach the PFPA to the glass substrates. The glass substrates were then rinsed thoroughly with dichloromethane and air dried.

A solution was then formed comprising about 20 milligrams of polypropylene in about 2 milliliters of toluene. The solution was heated to reflux and then spincoated onto the glass substrates to form while the solution was still hot, thereby forming a film on the glass substrate. The substrates with film coatings were baked at 60° C. for 20 minutes and then photolyzed at 254 nm for about 6 minutes. The photolysis resulted in the formation of an azide, which undergoes an insertion reaction with the polypropylene to attach the polypropylene to the glass substrates.

EXAMPLE 26

Several silica wafers were cleaned with concentrated $H_2SO_4$, water and acetone and then dried. A solution was then formed comprising 2 milliliters of 3-aminopropyltrimethoxysilane (Aldrich) in about 20 milliliters of toluene. The pieces of silica were added to the solution and the resulting composition was then refluxed overnight. The silica wafers were then washed thoroughly with toluene and air-dried to obtain silica wafers modified with 3-aminopropylalkoxy silanes.

A solution was then formed comprising about 13 milligrams of p-toluoyl chloride in 2 milliliters of dichloromethane. Silica wafers were then immersed in the solution of p-toluoyl chloride for about 20 minutes, then thoroughly washed with dichloromethane and air dried. The p-toluoyl chloride reacted with the amino group of the aminopropylsilane to attach the p-toluoyl moiety to the wafers.

The wafers were then spincoated with 0.5 percent NHS-PFPA in nitromethane at 1000 rpm, baked at 60° C. for 25 minutes and then photolyzed at 254 nms for about 6 minutes. The photolysis resulted in the formation of an azide, which then underwent a C—H insertion reaction at the benzyl carbon of the p-toluoyl moiety, thereby attaching the NHS-PFPA to the wafer.

The wafers were then immersed in a solution comprising about 0.5 milligram of aminoacetamidofluorescein in about 0.5 milliliter of methanol containing 5 μl triethylamine for 1 hour. The aminoacetamidofluorescein reacted with the NHS-PFPA to attach this fluorescent label to the wafer. The wafers were then thoroughly rinsed with methanol and dried. Fluorescent analysis of the resulting product demonstrated that aminoacetamidofluorescein was attached to the wafer as expected.

Examples 27 and 28 concern silane reagents that are reacted in a first step with a substrate capable of reacting with silane reagents, particularly silica or silicon substrates. This first step provides a substrate having a silane tether coupled thereto, wherein the silane tether includes a terminal C—H bond, such as is provided by a terminal methyl group. The terminal C—H bond can undergo an insertion and/or addition reaction in a subsequent step with a nitrenogenic group. This process is illustrated above in Schemes 18 and 19.

EXAMPLE 27

Several silica wafers were cleaned with concentrated $H_2SO_4$, water and acetone and then dried. A solution was then formed comprising 2 milliliters of propyltrimethoxysilane (Aldrich) in about 20 milliliters of toluene. The pieces of silica were added to the solution and the resulting composition was then refluxed overnight. The silica wafers were then washed thoroughly with toluene and air-dried to obtain silica wafers modified with the propyltrimethoxysilane.

The wafers were then spincoated with 0.5 percent NHS-PFPA in nitromethane at 1000 rpm, baked at 60° C. for 25 minutes and then photolyzed at 254 nms for about 6 minutes. The photolysis resulted in the formation of an azide, which then underwent a C—H insertion reaction at the pendent methyl group of the propyltrimethoxysilane, thereby attaching the NHS-PFPA to the wafer.

EXAMPLE 28

Several silica wafers were cleaned with concentrated $H_2SO_4$, water and acetone and then dried. A solution was then formed comprising 2 milliliters of propyltrimethoxysilane (Aldrich) in about 20 milliliters of toluene. The pieces of silica were added to the solution and the resulting composition was then refluxed overnight. The silica wafers were then washed thoroughly with toluene and air-dried to obtain silica wafers modified with the propyltrimethoxysilane.

The wafers were then spincoated with 0.5 percent NHS-PFPA in nitromethane at 1000 rpm, baked at 60° C. for 25 minutes and then photolyzed at 254 nms for about 6 minutes. The photolysis resulted in the formation of an azide, which then underwent a C—H insertion reaction at the pendent methyl group of the propyltrimethoxysilane, thereby attaching the NHS-PFPA to the wafer.

The examples provided above concern the reaction of alkoxy silanes with substrates. However, the alkoxy silanes are not the only reagents useful for practicing the present invention. For instance, the halosilanes and haloalkoxysilanes also can be used. Thus, silane reagents useful for practicing the present invention generally satisfy the formula Y—R—Si(OR')$_n$X$_{3-n}$ wherein n is 0–3, R is an aromatic group or an alkyl chain having 1–20 carbon atoms, R' is an alkyl chain having 1–10 carbon atoms, X is a halogen, and Y is selected from the group consisting of H, —OH, —NH$_2$ and —SH. The use of chlorosilanes is exemplified in Example 29.

EXAMPLE 29

Several silica wafers were cleaned with concentrated $H_2SO_4$, water and acetone and then dried. A solution was then formed comprising 2 octadecyltrichlorosilane (Aldrich) in about 20 milliliters of toluene. The pieces of silica were added to the solution and the resulting composition was then refluxed overnight. The silica wafers were then washed thoroughly with toluene and air-dried to obtain silica wafers modified with the octadecyldichlorosilane.

The wafers were then spincoated with 0.5 percent NHS-PFPA in nitromethane at 1000 rpm, baked at 60° C. for 25 minutes and then photolyzed at 254 nms for about 6 minutes. The photolysis resulted in the formation of an azide, which then underwent a C—H insertion reaction at the pendent methyl group of the octadecyldichlorosilane, thereby attaching the NHS-PFPA to the wafer.

After the silane reagent is attached to a substrate, it can then be reacted in a second stage with a desired reagent. One class of such reagents are the aromatic compounds, such as benzyl and toluoyl compounds. Toluoyl compounds can be coupled to the silane reagent. Thereafter, the benzyl carbon of the toluoyl group provides a site reactive to insertion and/or addition reactions with nitrenes. This approach is exemplified in Examples 30–33.

EXAMPLE 30

Several glass samples were cleaned with concentrated $H_2SO_4$, water and acetone and then dried. A solution was then formed comprising 2 milliliters of 3-aminopropyltrimethoxysilane (Aldrich) in about 20 milliliters of toluene. The glass samples were added to the solution and the resulting composition was then refluxed overnight. The glass samples were then washed thoroughly with toluene and air-dried to obtain glass samples modified with 3-aminopropylalkoxy silanes.

A solution was then formed comprising about 13 milligrams of p-toluoyl chloride in 2 milliliters of dichloromethane. Glass samples were then immersed in the solution of p-toluoyl chloride for about 20 minutes. The p-toluoyl chloride reacted with the amino group of the aminopropylsilane to attach the p-toluoyl moiety to the wafers. The samples were then thoroughly washed with dichloromethane and air dried.

Glass samples were then spincoated with 0.5 percent NHS-PFPA in nitromethane at 1000 rpm. The glass substrates were baked at 60° C. for 25 minutes and then photolyzed at 254 nm for about 6 minutes. The photolysis resulted in the formation of an azide from the NHS-PFPA, which then underwent a C—H insertion reaction at the benzyl carbon of the p-toluoyl moiety. This reaction attached the NHS-PFPA to the substrate.

The glass substrates were then immersed in a solution comprising about 0.5 milligram of aminoacetamidofluorescein in about 0.5 milliliters of methanol containing 5 µl triethylamine for 1 hour. The silicon wafer was then thoroughly rinsed with methanol and dried. The aminoacetamidofluorescein reacted with the NHS-PFPA to attach this fluorescent label to the wafer. Analysis of the resulting product using fluorescence microscopy demonstrated that aminoacetamidofluorescein was attached to the wafer as expected.

The methods of the present invention are useful for coating or functionalizing substrates so as to provide only preselected coated or functionalized regions, or substrates that are coated or functionalized in arrays. This approach is exemplified in Example 31.

EXAMPLE 31

This example describes the formation of chemical arrays, such as 3×3 arrays, on substrates. Several silica wafers samples were cleaned with concentrated $H_2SO_4$, water and acetone and then dried. A solution was then formed comprising 2 milliliters of 3-aminopropyltrimethoxysilane (Aldrich) in about 20 milliliters of toluene. The silica wafers were added to the solution and the resulting composition was then refluxed overnight. The wagers were then washed thoroughly with toluene and air-dried to obtain glass samples modified with 3-aminopropylalkoxy silanes.

A solution was then formed comprising about 13 milligrams of p-toluoyl chloride in 2 milliliters of dichloromethane. The wafers were then immersed in the solution of p-toluoyl chloride for about 20 minutes. The p-toluoyl chloride reacted with the amino group of the aminopropyl-silane to attach the p-toluoyl moiety to the wafers. The samples were then thoroughly washed with dichloromethane and air dried.

The wafers were then spincoated with 0.5 percent NHS-PFPA in nitromethane at 1000 rpm. The wafers were baked at 60° C. for 25 minutes and then photolyzed at 254 nm for about 6 minutes. The photolysis resulted in the formation of an azide from the NHS-PFPA, which then underwent a C—H insertion reaction at the benzyl carbon of the p-toluoyl moiety. This reaction attached the NHS-PFPA to the substrate.

The wafers were then spotted with a solution comprising about 0.5 milligram of aminoacetamidofluorescein in pH 9 NaOH in 3×3 arrays using a pipette. The solution comprising aminoacetamidofluorescein was left on the wafer for about 2 hours. The wafers were then rinsed with pH 9 NaOH, then distilled water, followed by air drying. Analysis of the resulting product using fluorescence microscopy demonstrated that aminoacetamidofluorescein was attached to the wafer as expected.

The wafer was then soaked in pH 9 NaOH overnight. Fluorescence microscopy again demonstrated that the aminoacetamidofluorescein remained attached to the wafer.

EXAMPLE 32

Silica wafers were cleaned with concentrated $H_2SO_4$, water and acetone and then dried. A solution was then formed comprising 2 milliliters of 3-aminopropyltrimethoxysilane (Aldrich) in about 20 milliliters of toluene. The pieces of silica were added to the solution and the resulting composition was then refluxed overnight. The silica wafers were then washed thoroughly with toluene and air-dried to obtain silica wafers modified with 3-aminopropylalkoxy silanes.

A solution was then formed comprising about 13 milligrams of p-toluoyl chloride in 2 milliliters of dichloromethane. Silica wafers were then immersed in the solution of p-toluoyl chloride for about 20 minutes, then thoroughly washed with dichloromethane and air dried. The p-toluoyl chloride reacted with the amino group of the aminopropyl-silane to attach the p-toluoyl moiety to the wafers.

The wafers were then spincoated with 0.5 percent NHS-PFPA in nitromethane at 1000 rpm, baked at 60° C. for 25 minutes and then photolyzed at 254 nm for about 5 minutes. The resulting products were then exposed to nitromethane to remove unattached reaction products. The photolysis resulted in the formation of an azide, which then underwent an insertion reaction at the benzyl carbon of the p-toluoyl moiety, thereby attaching the NHS-PFPA to the wafer.

50 µmolar concentrations of two proprietary 24-mer oligonucleotides in pH 8.3 Tris EDTA buffer were then pipetted onto the surface in about 1.2 microliter amounts onto the silica wafer in a two-by-two array. The proprietary oligonucleotides have an amino group at the 5' end, followed by an 18 carbon-chain spacer that was attached to the 24-mers. Also, fluorescent dyes were attached to the 24-mers at the 3' end. The solutions were left on the wafers for about 2.5 hours. The wafers were then rinsed with pH 8.3 Tris EDTA buffer, and thereafter soaked in the pH 9 Tris buffer for about 2 hours. The wafers were then rinsed with distilled water, and air dried. Apparently, the 5' amino group reacted with the NHS-PFPA ester to attach the proprietary oligonucleotides to the silica wafer. The attachment of the oligonucleotides to the wafer in the two-by-two array was confirmed by fluorescence microscopy.

The technique outline in Example 32 can be used to attach various oligonucleotides, DNA, oligopeptides or peptides to substrates. Moreover, these materials can be attached to the wafer in preselected patterns or arrays. This allows for the production of sensor devices that use nucleic acids, such as oligonucleotides and DNA, peptides, enzymes, oligopeptides, cells, or antibodies as the sensing moiety.

EXAMPLE 33

Quartz substrates are cleaned, rinsed with water and acetone, and then dried. A solution is then formed comprising 2 milliliters of 3-aminopropyltrimethoxysilane (Aldrich) in about 20 milliliters of toluene. The pieces of quartz are added to the solution and the resulting composition is then refluxed overnight. The quartz substrates are then washed thoroughly with toluene and air-dried to obtain quartz substrates modified with 3-aminopropylalkoxy silanes.

A solution is then formed comprising about 13 milligrams of p-toluoyl chloride in 2 milliliters of dichloromethane. The quartz substrates are then immersed in the solution of p-toluoyl chloride for about 20 minutes, then thoroughly washed with dichloromethane and air dried. The p-toluoyl chloride reacts with the amino group of the aminopropylsilane to attach the p-toluoyl moiety to the quartz substrates.

The quartz substrates are then spincoated with 0.5 percent NHS-PFPA in nitromethane at 1000 rpm, baked at 60° C. for 25 minutes and then photolyzed at 254 nm for about 5 minutes. The resulting products are then exposed to nitromethane to remove unattached reaction products. The photolysis results in the formation of an azide, which undergoes an insertion reaction at the benzyl carbon of the p-toluoyl moiety to attach the NHS-PFPA to the quartz substrates.

50 μmolar concentrations of oligonucleotides in pH 8.3 Tris EDTA buffer are then pipetted onto the surface in about 1.2 microliter amounts onto the quartz substrates in two-by-two arrays. The oligonucleotides have an amino group at the 5' end. Also, fluorescent dyes are attached to the oligonucleotides at the 3' end. The solutions are left on the quartz substrates for about 2.5 hours. The quartz substrates are then rinsed with pH 8.3 Tris EDTA buffer, and thereafter soaked in the pH 9 Tris buffer for about 2 hours. The quartz substrates are then rinsed with distilled water, and air dried. Apparently, the 5' amino group reacted with the NHS-PFPA ester to attach the oligonucleotides to the quartz substrate. The attachment of the oligonucleotides to the quartz substrates in two-by-two arrays could be confirmed by fluorescence microscopy.

EXAMPLE 34

This example describes the coating of silicon wells that are used for reactions, such as the PCR reaction. The silicon wells are primarily silicon materials with a layer of silicon dioxide on the surface thereof. Only the inside of the well need to be coated, as this is the portion of the surface of the silicon wells that contacts solutions when in use.

First, a commercial photoresist material (Hoescht) was coated onto the well. A photomask was placed on top of the well, and the well was exposed with a UV mask aligner. The photomask was designed so that only the outside edges of the well were exposed to the UV irradiation. The resist was developed, removing the exposed materials on the edges of the well. A layer of aluminum, about 200 nm thick, was then evaporated on top of the well. The well was then immersed in acetone to lift off the photoresist in the well and the aluminum deposited on top. This leaves a layer of aluminum only on the outside edges of the well.

A solution comprising 1% polypropylene in toluene and various amounts of bis-PFPA (0%, 2% and 6% based on polypropylene) was then spincoated onto the interior surface of the well to form a film. The well with the film coating were then photolyzed at 254 nm to crosslink the polypropylene, to produce a crosslinked polypropylene on the surface of the well. The well were soaked in 2% NaOH solution to remove the aluminium film and the polypropylene film on the outside edges of the well.

The crosslinked polypropylene films were annealed at 300° C. in nitrogen for up to one hour. The films survived the heating and became smoother. Plain polypropylene films evaporate at 300° C. Annealing the crosslinked polypropylene films at 300° C. in air decomposed the films. The residues evaporated at this temperature.

A particular process of the present invention concerns potentiating the biocompatability of a device that is intended for use as a medical implant, or which otherwise comes into contact with tissue or bodily fluids. The process generally comprises forming a substrate having a first coating thereon, such as the silane reagents of the present invention. In a second stage, the first coating is coupled to a second coating comprising a biocompatible material. This approach is exemplified in Example 35. A partial list of biocompatible materials includes polyetherurethaneurea (PEUU), 2-methacryloyloxyethyl phosphorylcholine (MPC), polytetrafluoroethylene (PTFE), heparin, polyethylene oxide, polyurethanes, polyesters, cellulose, chitosan, PEEK, antibacterial or antimicrobial agents and anti-coagulants. There are numerous additional examples of potentially biocompatible materials that can be coupled to substrates to potentiate their biocompatability. The present invention is intended to cover any biocompatible material now known or hereafter discovered that can be coupled to a substrate according to the procedures described herein.

EXAMPLE 35

This example describes modifying an angioplasty balloon surface with polyurethane, wherein the balloon is made from polyethyeleneteraphthalate (PET). A solution of NHS-PFPA ester in nitromethane was formed, and an angioplasty balloon, either flaccid or inflated with air or a liquid, made from PET was dipcoated with the solution. The product was then photolyzed at 254 nm for about 5 minutes. This produces an azide from the NHS-PFPA, which then undergoes an insertion reaction with the PET to place the NHS-PFPA ester on the surface of the balloon.

The balloon was then soaked in a solution comprising an amino-functionalized PFPA (various PFPAs with different spacers or linkers can be used for this process). The amino group of the amino-PFPA reacts with the NHS-PFPA ester. This attaches the amino-PFPA moiety to the balloon.

Polyurethane is then coated onto the balloon, such as by immersing the balloon into a solution of the polyurethane. The balloon with the surface coating of polyurethane is then photolyzed at about 254 nm for a period of about 5 minutes. This should attach the polyurethane to the surface of the PET balloon through an insertion reaction with an azide produced by the photolysis.

The following examples described procedures for modifying metal substrates. In general, the methods comprise selecting a reagent that is capable of reacting with a metal. For instance, thiols (RSH) can be used to react with a number of metals including, but not limited to, gold, copper, silver and platinum. Other metals can be reacted with reagents that are more suitable for reacting with a particular metal. One example is aluminum, which preferably is reacted with a carboxylic acid. These reactions with metals can proceed in a one stage reaction by forming a desired compound having a functional group capable of reacting with the metal in question. The coating or functionalization of metals also can proceed by a two-stage reaction. The two-stage approach comprises first coupling a reagent capable of reacting with metals to the metal substrate, followed by reacting this reagent with a subsequent material, such as, without limitation, a biocompatible polymer.

EXAMPLE 36

A substrate made from gold is reacted with 10-thiodecylamine to form a gold substrate modified with a decylamine. A solution of NHS-PFPA ester is then spincoated onto the gold substrate in a manner allowing for the NHS-PFPA ester to react with the amino group of the decylamine. The gold substrate is spincoated with polypropylene, and photolyzed for about 5 minutes. This causes the formation of a nitrene from the azide, which then undergoes an insertion reaction with the polypropylene. This results in the modification of the gold substrate with polypropylene.

EXAMPLE 37

A substrate made from gold is reacted with 1-decanethiol to form a gold substrate having a pendent C-10 carbon chain. A solution of NHS-PFPA ester is then spincoated onto the gold substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the gold surface. The gold substrate is then immersed in a solution of an oligonucleotide having a 5' amino group. The amino group reacts with the NHS-PFPA ester to form a gold substrate having an oligonucleotide attached thereto.

EXAMPLE 38

This example describes the formation of preselected patterns of materials on the surface of a gold substrate. A substrate made from gold is reacted with 1-decanethiol to form a gold substrate having a pendent C-10 carbon chain. A solution of NHS-PFPA ester is then spincoated onto the gold substrate, followed by photolysis at 254 nm for about 5 minutes using a UV mask aligner. This results in the formation of a nitrene from the azide group of the NHS-PFPA ester, which undergoes an insertion reaction with the pendent methyl group of the 1-decanthiol. This attaches the NHS-PFPA ester to the gold surface in preselected patterns. The gold substrate is then immersed in a solution of an oligonucleotide having a 5' amino group. The amino group reacts with the NHS-PFPA ester to form a gold substrate having oligonucleotides attached thereto in preselected patterns.

EXAMPLE 39

This example describes the formation of arrays on the surface of a gold substrate. A gold substrate is reacted with 1-decanethiol to form a gold substrate having a pendent C-10 carbon chain. A solution of NHSPFPA ester is then spincoated onto the gold substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the gold surface. The gold substrate is then spotted with a solution of an oligonucleotide having a 5' amino group using a pipette or a mechanical spotting device. The amino group reacts with the NHS-PFPA ester to form a gold substrate having an oligonucleotide attached thereto.

EXAMPLE 40

A substrate made from copper is reacted with 1-decanethiol to form a copper substrate having a pendent C-10 carbon chain. A solution of NHS-PFPA ester is then spincoated onto the copper substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the copper surface. The copper substrate is then immersed in a solution of an oligonucleotide having a 5' amino group. The amino group reacts with the NHS-PFPA ester to form a copper substrate having an oligonucleotide attached thereto.

EXAMPLE 41

This example describes the formation of preselected patterns of materials on the surface of a copper substrate. A copper substrate is reacted with 1-decanethiol to form a copper substrate having a pendent C-10 carbon chain. A solution of NHS-PFPA ester is then spincoated onto the copper substrate, followed by photolysis at 254 nm for about 5 minutes using a UV mask aligner. This results in the formation of a nitrene from the azide group of the NHS-PFPA ester, which undergoes an insertion reaction with the pendent methyl group of the 1-decanthiol. This attaches the NHS-PFPA ester to the copper surface in preselected patterns. The copper substrate is then immersed in a solution of an oligonucleotide having a 5' amino group. The amino group reacts with the NHS-PFPA ester to form a copper substrate having oligonucleotides attached thereto in preselected patterns.

EXAMPLE 42

This example describes the formation of arrays on the surface of a copper substrate. A copper substrate is reacted with 1-decanethiol to form a copper substrate having a pendent C-10 carbon chain. A solution of NHS-PFPA ester is then spincoated onto the copper substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the copper surface. The copper substrate is then spotted with a solution of an oligonucleotide having a 5' amino group using a pipette or a mechanical spotting device. The amino group reacts with the NHS-PFPA ester to form a copper substrate having an oligonucleotide attached thereto.

EXAMPLE 43

A substrate made from silver is reacted with 1-decanethiol to form a silver substrate having a pendent C-10 carbon chain. A solution of NHS-PFPA ester is then spincoated onto the silver substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the silver surface. The silver substrate is then immersed in a solution of an oligonucleotide having a 5' amino group. The amino group reacts with the NHS-PFPA ester to form a silver substrate having an oligonucleotide attached thereto.

EXAMPLE 44

This example describes the formation of preselected patterns of materials on the surface of a silver substrate. A silver substrate is reacted with 1-decanethiol to form a silver substrate having a pendent C-10 carbon chain. A solution of NHS-PFPA ester is then spincoated onto the copper substrate, followed by photolysis at 254 nm for about 5 minutes using a UV mask aligner. This results in the formation of a nitrene from the azide group of the NHS-PFPA ester, which undergoes an insertion reaction with the pendent methyl group of the 1-decanthiol. This attaches the NHS-PFPA ester to the silver surface in preselected patterns. The silver substrate is then immersed in a solution of an oligonucleotide having a 5' amino group. The amino group reacts with the NHS-PFPA ester to form a silver substrate having oligonucleotides attached thereto in preselected patterns.

EXAMPLE 45

This example describes the formation of arrays on the surface of a silver substrate. A silver substrate is reacted with 1-decanethiol to form a silver substrate having a pendent C-10 carbon chain. A solution of NHSPFPA ester is then spincoated onto the silver substrate, followed by photolysis at 254 nm for about 5 minutes. This results in the formation of a *nitrene from the azide group of the NHS-PFPA ester, which undergoes an insertion reaction with the pendent methyl group of the 1-decanthiol. This attaches the NHS-PFPA ester to the silver surface. The silver substrate is then spotted with a solution of an oligonucleotide having a 5' amino group using a pipette or a mechanical spotting device. The amino group reacts with the NHS-PFPA ester to form a silver substrate having an oligonucleotide attached thereto.

EXAMPLE 46

A substrate made from platinum is reacted with 1-decanethiol to form a platinum substrate having a pendent C-10 carbon chain. A solution of NHS-PFPA ester is then spincoated onto the platinum substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the platinum surface. The platinum substrate is then immersed in a solution of an oligonucleotide having a 5' amino group. The amino group reacts with the NHS-PFPA ester to form a platinum substrate having an oligonucleotide attached thereto.

EXAMPLE 47

This example describes the formation of preselected patterns of materials on the surface of a platinum substrate. A platinum substrate is reacted with 1-decanethiol to form a platinum substrate having a pendent C-10 carbon chain. A solution of NHS-PFPA ester is then spincoated onto the platinum substrate, followed by photolysis at 254 nm for about 5 minutes using a UV mask aligner. This results in the formation of a nitrene from the azide group of the NHS-PFPA ester, which undergoes an insertion reaction with the pendent methyl group of the 1-decanthiol. This attaches the NHS-PFPA ester to the platinum surface in preselected patterns. The platinum substrate is then immersed in a solution of an oligonucleotide having a 5' amino group. The amino group reacts with the NHS-PFPA ester to form a platinum substrate having oligonucleotides attached thereto in preselected patterns.

EXAMPLE 48

This example describes the formation of arrays on the surface of a platinum substrate. A platinum substrate is reacted with 1-decanethiol to form a platinum substrate having a pendent C-10 carbon chain. A solution of NHS-PFPA ester is then spincoated onto the platinum substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the platinum surface. The platinum substrate is then spotted with a solution of an oligonucleotide having a 5' amino group using a pipette or a mechanical spotting device. The amino group reacts with the NHS-PFPA ester to form a platinum substrate having an oligonucleotide attached thereto.

EXAMPLE 49

A substrate made from aluminum is reacted with an decanoic acid in a manner that allows the carboxylic acid moiety to react with the aluminum. This produces an aluminum substrate having a surface modified with a carbon chain. A solution of an NHS-PFPA ester is then spincoated onto the aluminum substrate, followed by photolysis at 254 nm for about 5 minutes. A nitrene is formed from the azide group of the NHS-PFPA ester, which undergoes a C—H insertion reaction with the pendent alkyl group of the carbon chain. This attaches the NHSPFPA ester to the aluminum surface. The aluminum substrate is then immersed in a solution of an oligonucleotide having a 5' amino group in Tris buffer. The amino group reacts with the NHS-PFPA ester to form an aluminum substrate having an oligonucleotide attached thereto.

EXAMPLE 50

This example describes the formation of preselected patterns of materials on the surface of an aluminum substrate. An aluminum substrate is reacted with an decanoic acid in a manner that allows the carboxylic acid moiety to react with the aluminum. This produces an aluminum substrate having a surface modified with a carbon chain. A solution of an NHS-PFPA ester is then spincoated onto the aluminum substrate, followed by photolysis at 254 nm for about 5 minutes using a UV mask aligner. A nitrene is formed from the azide group of the NHS-PFPA ester, which undergoes a C—H insertion reaction with the pendent alkyl group of the carbon chain. This attaches the NHS-PFPA ester to the aluminum surface in preselected patterns. The aluminum substrate is then immersed into a solution of an oligonucleotide having a 5' amino group in Tris buffer. The amino group reacts with the NHS-PFPA ester to form an aluminum substrate having an oligonucleotides attached thereto in preselected patterns.

EXAMPLE 51

This example described the formation of arrays on the surfaces of aluminum substrates. An aluminum substrate is reacted with an decanoic acid in a manner that allows the carboxylic acid moiety to react with the aluminum. This produces an aluminum substrate having a surface modified with a carbon chain. A solution of an NHS-PFPA ester is then spincoated onto the aluminum substrate, followed by photolysis at 254 nm for about 5 minutes. A nitrene is formed from the azide group of the NHS-PFPA ester, which undergoes a C—H insertion reaction with the pendent alkyl group of the carbon chain. This attaches the NHS-PFPA ester to the aluminum surface. The aluminum substrate is then spotted with an oligonucleotide having a 5' amino group using a pipette or a mechanical spotting device. The amino group reacts with the NHS-PFPA ester to form an aluminum substrate having an oligonucleotide attached thereto in arrays.

Semiconductor materials also can be coated and/or functionalized using the procedures of the present invention. Examples 52–57 concern coating and/or functionalizing semiconductor substrates.

EXAMPLE 52

A substrate made from gallium arsenide (GaAs) is reacted with 1-decanethiol to form a GaAs substrate having a pendent C-10 carbon chain. A solution of NHS-PFPA ester is then spincoated onto the GaAs substrate, followed by photolysis at 254 nm for about 5 minutes. This results in the formation of a nitrene from the azide group of the NHS-PFPA ester, which undergoes an insertion reaction with the pendent methyl group of the 1-decanethiol. This attaches the NHS-PFPA ester to the GaAs surface. The GaAs substrate is then immersed in a solution of an oligonucleotide having a 5' amino group. The amino group reacts with the NHS-PFPA ester to form a GaAs substrate having an oligonucleotide attached thereto.

EXAMPLE 53

This example describes the formation of preselected patterns of materials on the surface of a GaAs substrate. A GaAs substrate is reacted with 1-decanethiol to form a GaAs substrate having a pendent C-10 carbon chain. A solution of NHS-PFPA ester is then spincoated onto the GaAs substrate, followed by photolysis at 254 nm for about 5 minutes using a UV mask aligner. This results in the formation of a nitrene from the azide group of the NHS-PFPA ester, which undergoes an insertion reaction with the pendent methyl group of the 1-decanethiol. This attaches the NHS-PFPA ester to the GaAs surface in preselected patterns. The GaAs substrate is then immersed in a solution of an oligonucleotide having a 5' amino group. The amino group reacts with the NHS-PFPA ester to form a GaAs substrate having oligonucleotides attached thereto in preselected patterns.

EXAMPLE 54

This example describes the formation of arrays on the surface of a GaAs substrate. A GaAs substrate is reacted with 1-decanethiol to form a GaAs substrate having a pendent C-10 carbon chain. A solution of NHS-PFPA ester is then spincoated onto the GaAs substrate, followed by photolysis at 254 nm for about 5 minutes. This results in the formation of a nitrene from the azide group of the NHS-PFPA ester, which undergoes an insertion reaction with the pendent methyl group of the 1-decanethiol. This attaches the NHS-PFPA ester to the GaAs surface. The GaAs substrate is then spotted with a solution of an oligonucleotide having a 5' amino group using a pipette or a mechanical spotting device. The amino group reacts with the NHS-PFPA ester to form a GaAs substrate having an oligonucleotide attached thereto.

EXAMPLE 55

A substrate made from cadmium sulfide (CdS) is reacted with 1-decanethiol to form a CdS substrate having a pendent C-10 carbon chain. A solution of NHS-PFPA ester is then spincoated onto the CdS substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the CdS surface. The CdS substrate is then immersed in a solution of an oligonucleotide having a 5' amino group. The amino group reacts with the NHS-PFPA ester to form a CdS substrate having an oligonucleotide attached thereto.

EXAMPLE 56

This example describes the formation of preselected patterns of materials on the surface of a CdS substrate. A CdS substrate is reacted with 1-decanethiol to form a CdS substrate having a pendent C-10 carbon chain. A solution of NHS-PFPA ester is then spincoated onto the CdS substrate, followed by photolysis at 254 nm for about 5 minutes using a UV mask aligner. This results in the formation of a nitrene from the azide group of the NHS-PFPA ester, which undergoes an insertion reaction with the pendent methyl group of the 1-decanthiol. This attaches the NHS-PFPA ester to the CdS surface in preselected patterns. The CdS substrate is then immersed in a solution of an oligonucleotide having a 5' amino group. The amino group reacts with the NHS-PFPA ester to form a CdS substrate having oligonucleotides attached thereto in preselected patterns.

EXAMPLE 57

This example describes the formation of arrays on the surface of a CdS substrate. A CdS substrate is reacted with 1-decanethiol to form a CdS substrate having a pendent C-10 carbon chain. A solution of NHS-PFPA ester is then spincoated onto the CdS substrate, followed by photolysis at 254 nm for about 5 minutes. This results in the formation of a nitrene from the azide group of the NHS-PFPA ester, which undergoes an insertion reaction with the pendent methyl group of the 1-decanthiol. This attaches the NHS-PFPA ester to the CdS surface. The CdS substrate is then spotted with a solution of an oligonucleotide having a 5' amino group using a pipette or a mechanical spotting device. The amino group reacts with the NHS-PFPA ester to form a CdS substrate having an oligonucleotide attached thereto.

Several of the examples provided above concern reacting certain substrates, particularly metals, with thiols. Disulfide reagents also can be used for such purposes. Example 58 illustrates the use of disulfides for coating a gold substrate.

EXAMPLE 58

A substrate made from gold is reacted with octyl sulfide (Aldrich) to form a gold substrate having a pendent C-8 carbon chain. A solution of NHS-PFPA ester is then spincoated onto the gold substrate, followed by photolysis at 254 nm for about 5 minutes. This results in the formation of a nitrene from the azide group of the NHS-PFPA ester, which undergoes an insertion and/or addition reaction with the pendent methyl group of the 1-octylthiol. This attaches the NHS-PFPA ester to the gold surface. The gold substrate is then immersed in a solution of an oligonucleotide having a 5' amino group. The amino group reacts with the NHS-PFPA ester to form a gold substrate having an oligonucleotide attached thereto.

While the invention has been described in connection with preferred embodiments and multiple examples, it will be understood that it is not limited to those embodiments. On the contrary, it is intended to cover all alternatives, modifications, and equivalents as may be included within the spirit and scope of the invention as defined by the appended claims.

We claim:

1. A method for coating a substrate, comprising:
   providing a substrate; and
   coating at least a portion of the substrate with a monolayer of a coating material to provide a substrate coated with a monolayer of the coating material wherein, prior to the coating, the coating material satisfies the formula $$Y\text{—}R\text{—}Si(OR')_n X_{3-n}$$

wherein n is 0–3, R is an aromatic group or an alkyl chain having 1–20 carbon atoms, R' is an alkyl chain having 1–10 carbon atoms, X is a halogen, Y is selected from the group consisting of H, —OH, —NH$_2$ and —SH, so that if Y is H the method further comprises bringing the coated substrate into reactive proximity with a perhalophenyl azide (PHPA), and exposing the substrate and the PHPA to a reaction energy source to couple the PHPA to the substrate, and if Y is selected from the group consisting of OH, —SH and —NH$_2$ the method further comprises reacting the coated substrate with a PHPA to produce a substrate having a PHPA attached thereto.

2. The method according to claim 1 wherein the step of exposing comprises exposing only preselected portions of the substrate to the reaction energy source.

3. The method according to claim 1 wherein the PHPA is an N-hydroxysuccinimide active ester-functionalized perfluorophenyl azide (NHS-PFPA).

4. The method according to claim 3 and further comprising reacting the NHS-PFPA with a nucleophile to couple the nucleophile to the substrate.

5. The method according to claim 4 wherein the nucleophile is selected from the group consisting of peptides, nucleotides, cells and antibodies.

6. The method according to claim 1 and further comprising:
   bringing the substrate with attached PHPA into reactive proximity with a material having chemical moieties each capable of undergoing an insertion and/or addition reaction with a nitrene; and
   exposing the substrate to a reaction energy source to form nitrenes that undergo insertion and/or addition reactions with the chemical moieties capable of undergoing insertion and/or addition reactions with nitrenes.

7. The method according to claim 6 wherein the step of exposing comprises exposing only preselected portions of the substrate to the reaction energy source.

8. The method according to claim 6 wherein the material having chemical moieties each capable of undergoing an insertion and/or addition reaction with a nitrene is a polymeric material.

9. The method according to claim 8 wherein the polymeric material is a biocompatible polymer.

10. A method for coating a substrate, comprising coating at least a portion of the substrate with a monolayer of a material that, prior to the coating, satisfies the formula $$Z\text{—}R_1\text{—}Y\text{—}R_2\text{—}Si(OR_3)_n X_{3-n}$$

wherein n is 3 or less, R$_1$ is a perhalophenyl azide (PHPA) or is selected from the group consisting of aromatic groups or alkyl, alkenyl or an alkynyl chains having 1–20 carbon atoms, R$_2$ is an aromatic group or an alkyl, alkenyl or an alkynyl chain having 1–20 carbon atoms, R$_3$ is an alkyl chain having 1–10 carbon atoms, X is a halogen, Y is NH, COO—, CON— or COS—, and Z is a methyl group, —N$_3$, —NH$_2$, —OH or —SH and wherein if R$_1$ is other than a PHPA and Z is selected from the group consisting of —NH$_2$, —OH and —SH the method further comprises reacting Z with a PHPA, and if Z is N$_3$ the method further comprises bringing the substrate into reactive proximity with a material having chemical moieties each capable of undergoing an insertion and/or addition reaction with a nitrene and exposing the substrate to a reaction energy source to form nitrenes that undergo an insertion and/or addition reactions with the chemical moieties capable of undergoing insertion and/or addition reactions with nitrenes.

11. The method according to claim 10 wherein the PHPA is an NHS-PFPA.

12. The method according to claim 11 and further comprising reacting a nucleophile with the NHS-PFPA to attach the nucleophile to the substrate.

13. The method according to claim 12 wherein the nucleophile is selected from the group consisting of a peptide, a nucleotide, cells and antibodies.

14. The method according to claim 10 wherein the material having chemical moieties each capable of undergoing an insertion and/or addition reaction with a nitrene is a polymeric material.

15. The method according to claim 14 wherein the polymeric material is a biocompatible material.

16. The method according to claim 15 wherein the substrate is an implantable medical device or comes into contact with blood or tissue.

17. A method for coating a material, comprising:
    providing a metal or metal alloy workpiece comprising surface molecules capable of reacting with Si atoms without the addition of a free-radical generator;
    exposing at least a portion of the surface molecules to a monolayer of a coating material that, prior to the exposing step, satisfies the formula $$Y\text{—}R\text{—}Si\text{—}(OR')_n(X)_{3-n}$$

wherein n is 0–3, R is selected from the group consisting of aromatic organic compounds and alkyl chains having from about 1–20 carbon atoms, R' is a carbon chain having from about 1 to about 10 carbon atoms, X is a halogen and Y is selected from the group consisting of H, —OH, —SH and NH$_2$; and
    bringing the substrate and the coating material into reactive proximity to form a substrate having a coating material covalently attached thereto.

18. The method according to claim 17 wherein Y is —OH, —SH or NH$_2$, and further comprising:
    providing an electrophile capable of reacting with Y; and
    bringing the substrate and electrophile into reactive proximity to covalently bond the electrophile to the substrate.

19. The method according to claim 18 wherein the electrophile is an electrophilic PHPA.

20. The method according to claim 19 wherein the electrophilic PHPA is an NHS-PFPA.

21. The method according to claim 17 and further comprising:
    providing a nucleophilic coating material; and
    bringing the substrate and nucleophilic coating material into reactive proximity to covalently bond the nucleophilic coating material to the substrate.

22. The method according to claim 21 wherein the nucleophilic coating material is selected from the group consisting of peptides, nucleotides, cells and antibodies.

23. The method according to claim 17 wherein Y is H, and further comprising:
providing a reagent comprising molecules each including a nitrenogenic group;
bringing the substrate with its coating material into reactive proximity with the reagent; and
while the substrate with its coating material and the reagent are in reactive proximity, exposing the reagent to a reaction energy source to convert the nitrenogenic groups to nitrenes that undergo insertion and/or addition reactions with the coating material.

24. The method according to claim 23 wherein the reagent is a functionalized PHPA.

25. The method according to claim 24 wherein the functionalized PHPA is an electrophilic PHPA.

26. The method according to claim 25 wherein the electrophilic PHPA is an NHS-PFPA.

27. A method for coating a metal or alloy substrate, comprising coating at least a portion of a metal or alloy substrate with a monolayer of a coating material that, prior to the coating, satisfies a first formula

Y—R—Z wherein
(a) R is an aromatic group or an alkyl, alkenyl or an alkynyl chain having 1–20 carbon atoms;
(b) Y is H, —OH, —SH, or NH$_2$; and
(c) Z is —SH, CO$_2$H, or Si(OR')$_n$X$_{3-n}$ wherein n is 0–3 and R' is an alkyl chain having 1–10 carbon atoms, or a second formula (Y—R—Z—)$_2$ wherein
(d) R is an aromatic group or an alkyl, alkenyl or an alkynyl chain having 1–20 carbon atoms;
(e) Y is H, —OH, —SH, or NH$_2$; and
(f) Z is S or an anhydride.

28. The method according to claim 27 wherein the coating material is a carboxylic acid or an anhydride and the substrate is an aluminum substrate.

29. The method according to claim 27 wherein the coating material is applied only to preselected portions of the substrate.

30. The method according to claim 29 wherein the preselected portions are arrays.

31. The method according to claim 27 wherein Y is —OH, —SH —NH$_2$ and further comprising reacting the coated substrate with a PHPA to produce a substrate having an PHPA attached thereto.

32. The method according to claim 27 wherein Y is H, and further comprising:
providing a reagent comprising molecules each including a nitrenogenic group;
bringing the substrate with its coating material into reactive proximity with the reagent; and
while the substrate with its coating material and the reagent are in reactive proximity, exposing the reagent to a reaction energy source to convert the nitrenogenic groups to nitrenes that undergo insertion and/or addition reactions with the coating material.

* * * * *